US 6,544,701 B2

(12) United States Patent
Tadokoro et al.

(10) Patent No.: US 6,544,701 B2
(45) Date of Patent: Apr. 8, 2003

(54) REACTION PRODUCT, PROCESS FOR THE PRODUCTION THEREOF, ELECTROPHOTOGRAPHIC PHOTOCONDUCTOR USING THE REACTION PRODUCT, ELECTROPHOTOGRAPHIC APPARATUS USING THE PHOTOCONDUCTOR, AND PROCESS CARTRIDGE FOR ELECTROPHOTOGRAPHIC APPARATUS

(75) Inventors: Kaoru Tadokoro, Yamatoshi (JP);
Masayuki Shoshi, Suntoh-gun (JP);
Michihiko Namba, Yokohama (JP);
Tomoyuki Shimada, Suntoh-gun (JP);
Chiaki Tanaka, Tagata-gun (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 10/062,428

(22) Filed: Feb. 5, 2002

(65) Prior Publication Data

US 2003/0013028 A1 Jan. 16, 2003

Related U.S. Application Data

(62) Division of application No. 09/602,186, filed on Jun. 22, 2000, now Pat. No. 6,465,648.

(30) Foreign Application Priority Data

| Sep. 14, 1999 | (JP) | ............................................. | 11-260632 |
| Sep. 14, 1999 | (JP) | ............................................. | 11-260633 |
| Sep. 14, 1999 | (JP) | ............................................. | 11-260634 |
| Jun. 22, 1999 | (JP) | ............................................. | 11-175213 |
| Jun. 22, 1999 | (JP) | ............................................. | 11-175240 |
| Mar. 14, 2000 | (JP) | ........................................ | 2000-070353 |

(51) Int. Cl.[7] ...................... G03G 15/02; C07D 401/10
(52) U.S. Cl. .................. 430/58.25; 430/59.5; 544/225; 544/357
(58) Field of Search .................. 430/58.25, 59.5; 544/225, 357

(56) References Cited

U.S. PATENT DOCUMENTS

| 5,457,232 A | 10/1995 | Tanaka et al. |
| 5,459,275 A | 10/1995 | Tanaka et al. |
| 5,492,784 A | 2/1996 | Yoshikawa et al. |
| 5,576,132 A | 11/1996 | Tanaka et al. |
| 5,578,405 A | 11/1996 | Ikegami et al. |
| 5,587,516 A | 12/1996 | Tanaka et al. |
| 5,599,995 A | 2/1997 | Tanaka et al. |
| 5,604,065 A | 2/1997 | Shimada et al. |
| 5,616,805 A | 4/1997 | Tanaka et al. |
| 5,672,728 A | 9/1997 | Tanaka et al. |
| 5,672,756 A | 9/1997 | Shimada et al. |
| 5,700,614 A | 12/1997 | Kawahara et al. |
| 5,750,762 A | 5/1998 | Kawahara et al. |
| 5,853,935 A | 12/1998 | Suzuki et al. |
| 5,942,362 A | 8/1999 | Tadokoro et al. |
| 5,942,363 A | 8/1999 | Tanaka et al. |
| 5,981,124 A | 11/1999 | Shimada et al. |
| 6,068,956 A | 5/2000 | Namba et al. |
| 6,074,792 A | 6/2000 | Namba et al. |

FOREIGN PATENT DOCUMENTS

| GB | 471418 | 8/1997 |
| JP | 2-39160 | 2/1990 |
| JP | 02 232268 | 9/1990 |
| JP | 4-113361 | 4/1992 |
| JP | 4-283581 | 10/1992 |
| JP | 2000-144005 | 5/2000 |
| WO | WO 99/23096 | 5/1999 |

OTHER PUBLICATIONS

V.B. Jigajinni, et al., High Perform. Polym, vol. 5, No. 3, pp. 239–257, "Structure–Property Relationships in PMR–15–Type Polyimide Resins:III. New Polyimides Incorporating Triazoles, Quinoxalines, Pyridopyrazines and Pyrazinopyridazines", 1993.

Abd El–Ghaffar, et al., Chemical Abstracts, vol. 110 No. 9, AN156087J, p. 91, May 1, 1989, "New Class of Metal Pyridino–Porphyrazine Pigments", vol. 17, No. 5, 1988.

Jae–Yun Jaung, et al., Dyes and Pitments, vol. 40, No.. 1, pp. 73–81, "Dicyanopyrazine Studies. Part VI: Absorption Spectra and Aggregation Behaviour of Tetrapyrazinopopphyrazines with Long Alkyl Groups", 1998.

*Primary Examiner*—Mark A. Chapman
(74) *Attorney, Agent, or Firm*—Oblon, Spivak, McClelland, Maier & Neustadt, P.C.

(57) ABSTRACT

To provide a novel reaction product useful as an organic photoconductive material for electrophotographic photoconductors.

A product obtainable by reacting (i) a nitrile derivative, (ii) a phthalonitrile derivative or a 1,3-diiminoisoindoline derivative and, if necessary, (iii) a metal or a metal-containing compound.

40 Claims, 35 Drawing Sheets

REACTION PRODUCT, PROCESS FOR THE PRODUCTION THEREOF, ELECTROPHOTOGRAPHIC PHOTOCONDUCTOR USING THE REACTION PRODUCT, ELECTROPHOTOGRAPHIC APPARATUS USING THE PHOTOCONDUCTOR, AND PROCESS CARTRIDGE FOR ELECTROPHOTOGRAPHIC APPARATUS

This application is a Division of application Ser. No. 09/602,186 filed on Jun. 22, 2000, now U.S. Pat. No. 6,465,648.

BACKGROUND OF THE INVENTION

The present invention relates to a novel reaction product, to a pigment comprising the reaction product, to a process of producing same, to an electrophotographic photoconductor using such a reaction product, to an electrophotographic apparatus having such an electrophotographic photoconductor, and to a process cartridge for such an electrophotographic apparatus.

Conventionally, the photoconductive material for use in the electrophotographic process is roughly divided into two groups, that is, an inorganic photoconductive material and an organic photoconductive material. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electric charge of the exposed area, so that a latent electrostatic image is formed on the photoconductor. The thus formed latent electrostatic image is developed into a visible image by use of a toner comprising a coloring agent such as a dye or pigment, and a polymeric material. Such an electrophotographic process is called "Carlson process".

The photoconductor employing the organic photoconductive material is advantageous over that employing the inorganic photoconductive material with respect to the degree of freedom in the wave range of the light to be employed, and the film-forming properties, flexibility, transparency, productivity, toxicity, and manufacturing cost of the photoconductor. In light of the above-mentioned advantages, most of the current photoconductors employ the organic photoconductive material. The photoconductor which is repeatedly operated by the above-mentioned electrophotographic process or the like is required to exhibit excellent electrostatic properties, more specifically, excellent photosensitivity, acceptance potential, retentivity of charge, potential stability, residual potential and spectral sensitivity.

In recent years, the development of data processing apparatus employing the above-mentioned electrophotographic process is remarkable. In particular, there is a remarkable improvement in the printing quality and the reliability of the digital printer which is capable of recording data by digital recording method, to be more specific, converting the data into digital signals and recording the data using a light. Such a digital recording system is applied not only to the printer, but also to the copying machine. Thus, the digital copying machine is actively developed. It is supposed that the demand for the digital copying machine will further increase in line with the addition of various data processing functions.

The photoconductor designed for the above-mentioned digital recording system is required to have special characteristics which are different from those required for the conventional analogue recording system. For instance, semiconductor laser (LD) or light emitting diode (LED) is widely employed as a light source for the digital recording system because of its compactness, cheapness and high reliability. The wave range of the currently used LD is within the near infrared region, while the wavelength of the currently used LED is 650 nm or more. Therefore, the electrophotographic photoconductors for use with the above-mentioned digital recording system are required to show sufficient sensitivity in the wavelength range from the visible region to the near infrared region. In light of the above-mentioned sensitivity, a squarylium dye (Japanese Laid-Open Patent Applications 49-105536 and 58-21416), a triphenylamine trisazo pigment (Japanese Laid-Open Patent Application 61-151659), and a phthalocyanine pigment (Japanese Laid-Open Patent Applications 48-34189 and 57-14874) are proposed as the photoconductive materials for use in the digital recording.

In particular, the phthalocyanine pigment, that is, a titanyltetraazaporphyrin compound, can show absorption and photosensitivity in the relatively long wavelength range. In addition, a variety of phthalocyanine pigments can be obtained according to the kind of central metal or the type of crystalline form. Therefore, research and development of this type of phthalocyanine pigment has been actively conducted to obtain the improved photoconductive material for use with the digital recording. Examples of the conventional phthalocyanine pigments capable of showing good sensitivity include $\epsilon$-type copper phthalocyanine, X-type metal-free phthalocyanine, $\tau$-type metal-free phthalacyanine, vanadyl phthalocyanine, and titanyl phthalocyanine. To be more specific, titanylphthalocyanine pigments with high sensitivity are proposed in Japanese Laid-Open Patent Applications 64-17066, 3-128973 and 5-98182. Those titanylphthalocyanine pigments exhibit maximum absorption in the wavelength range of 700 to 860 nm, so that they can show remarkably high sensitivity with respect to the semiconductor laser beam. It is also known to be effective for the purpose of obtaining phthalocyanine pigments with specific crystal structures to treat the phthalocyanine pigments with an acid, an organic solvent or water (Japanese Laid-Open Patent Applications 145550). Japanese Laid-Open Patent Applications Nos. 8-6050, 8-283599 and 2-269776 disclose a method of treating titanyl phthalocyanines with trihaloacetic acid.

However, when each of the above-mentioned titanylphthalocyanine pigments is employed in the electrophotographic photoconductor, there still remain a lot of practical problems, for example, decline in charging performance due to fatigue, and an increase in temperature- and humidity-dependence of the charging characteristics although the sensitivity is sufficient [Y. Fujimaki, Proc. IS&T's 7th International Congress on Advances in Non-Impact Printing Technologies, 1,269 (1991); K. Daimon et al.; J. Imaging Sci. Technol., 40,249 (1996)].

With regard to other tetraazaporphyrin derivatives, Japanese Patent Publication No. 2-39160, 3-27111, 4-283581 and 4-113361 disclose that pigments with asymmetric scheletons or mixed pigments such as a mixture of a phthalocyanine with a phthalocyanine-nitrogen or phthalocyanine-sulfur analogue is effective as the photoconductive material.

When these pigments are used for an electrophotographic photoconductor, the sensitivity in the visible light and near infrared range, charging characteristics and resistance to repeated use are still unsatisfactory.

SUMMARY OF THE INVENTION

It is an object of the present invention to remove the drawbacks of the photoconductive material in the conventional electrophotographic photoconductors and to provide a novel reaction product useful as an organic photoconductive material for electrophotographic photoconductors, a process of producing such a reaction product, an electrophotographic photoconductor containing such a reaction product, an electrophotographic machine using such a photoconductor and a process cartridge for an electrophotographic machine.

The present inventors have made an earnest study with a view toward solving the above problems and have found that a crystalline reaction product capable of being obtained by reaction of (i) a nitrile derivative of the formula (1) shown below with (ii) a phthalonitrile derivative of the formula (2) shown below or a 1,3-diiminoisoindoline derivative of the formula (3) shown below and, if necessary, with (iii) a metal or a metal-containing compound shows excellent charge generating properties and excellent electrophotographic characteristics. The present invention is based on this finding.

In accordance with the present invention, there is provide a crystalline reaction product having charge generating properties and capable of being obtained by reacting a nitrile derivative of the general formula (1) shown below with a phthalonitrile derivative of the general formula (2) shown below.

In accordance with the present invention, there is also provided a crystalline reaction product having charge generating properties and capable of being obtained by reacting a nitrile derivative of the general formula (1) shown below with a phthalonitrile derivative of the general formula (2) below and with a metal or a metal compound.

In accordance with the present invention, there is further provided a crystalline reaction product having charge generating properties and capable of being obtained by reacting a nitrile derivative of the general formula (1) shown below with a 1,3-diiminoisoindoline derivative of the formula (3) shown below.

In accordance with the present invention, there is further provided a crystalline reaction product having charge generating properties and capable of being obtained by reacting a nitrile derivative of the general formula (1) shown below with a 1,3-diiminoisoindoline derivative of the formula (3) shown below and with a metal or a metal compound.

In accordance with the present invention, there is provided an amorphous reaction product capable of being obtained by reacting a nitrile derivative of the general formula (1) shown below with a phthalonitrile derivative of the general formula (2) below.

In accordance with the present invention, there is further provided an amorphous reaction product capable of being obtained by reacting a nitrile derivative of the general formula (1) shown below with a phthalonitrile derivative of the general formula (2) shown below and with a metal or a metal compound.

In accordance with the present invention, there is further provided an amorphous reaction product capable of being obtained by reacting a nitrile derivative of the general formula (1) shown below with a 1,3-diiminoisoindoline derivative of the formula (3) shown below.

In accordance with the present invention, there is further provided an amorphous reaction product capable of being obtained by reacting a nitrile derivative of the general formula (1) shown below with a 1,3-diiminoisoindoline derivative of the formula (3) shown below and with a metal or a metal compound.

In accordance with the present invention, there is further provided a process for the production of a reaction product having a strong diffraction peak at a Bragg angle 2θ±0.2° of 27.2° but having no diffraction peak at a Bragg angle 2θ±0.2° of in the range of 4°–10° in a CuK$_\alpha$ X-ray diffraction pattern thereof, characterized in that a reaction product having a strong diffraction peak at a Bragg angle 2θ±0.2° of 27.2° and having weak diffraction peak at a Bragg angle 2θ±0.2° of in the range of 4°–10° in a CuK$_\alpha$ X-ray diffraction pattern thereof or the above amorphous reaction product is subjected to a crystal conversion treatment using at least one solvent selected from organic solvents, acids and water.

In accordance with the present invention, there is further provided a pigment characterized in that the pigment comprises the above crystalline reaction product having charge generating properties.

In accordance with the present invention, there is further provided an electrophotographic photoconductor comprising an electroconductive support and a photoconductive layer provided thereon, characterized in that the photoconductive layer comprises the above pigment.

In accordance with the present invention, there is further provided an electrophotographic machine comprising charging means, exposing means, developing means, transfer means, cleaning means, charge removing means and an electrophotographic photoconductor, characterized in that the above electrophotographic photoconductor is mounted as the electrophotographic photoconductor.

In accordance with the present invention, there is further provided a process cartridge for an electrophotographic machine comprising charging means and an electrophotographic photoconductor, characterized in that the above electrophotographic photoconductor is mounted as the electrophotographic photoconductor.

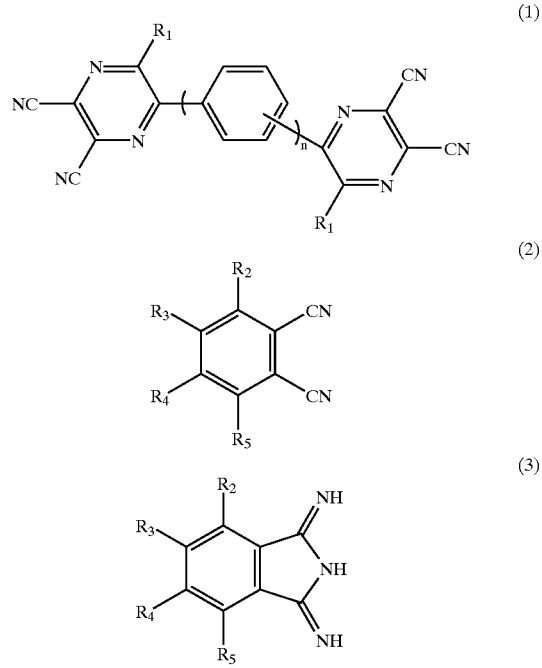

In the above formulas (1)–(3), $R_1$–$R_5$ stand, independently from each other, for a hydrogen atom, a halogen atom, an aliphatic hydrocarbyl group which may have a substituent, an aromatic group which may have a substituent, a hydrocarbyloxy group which may have a substituent, a nitro group or a cyano group and n is an integer of 1 or 2, with the proviso that two of $R_2$–$R_5$ may link to each other to form a ring.

EMBODIMENTS OF THE INVENTION

Figure 1:
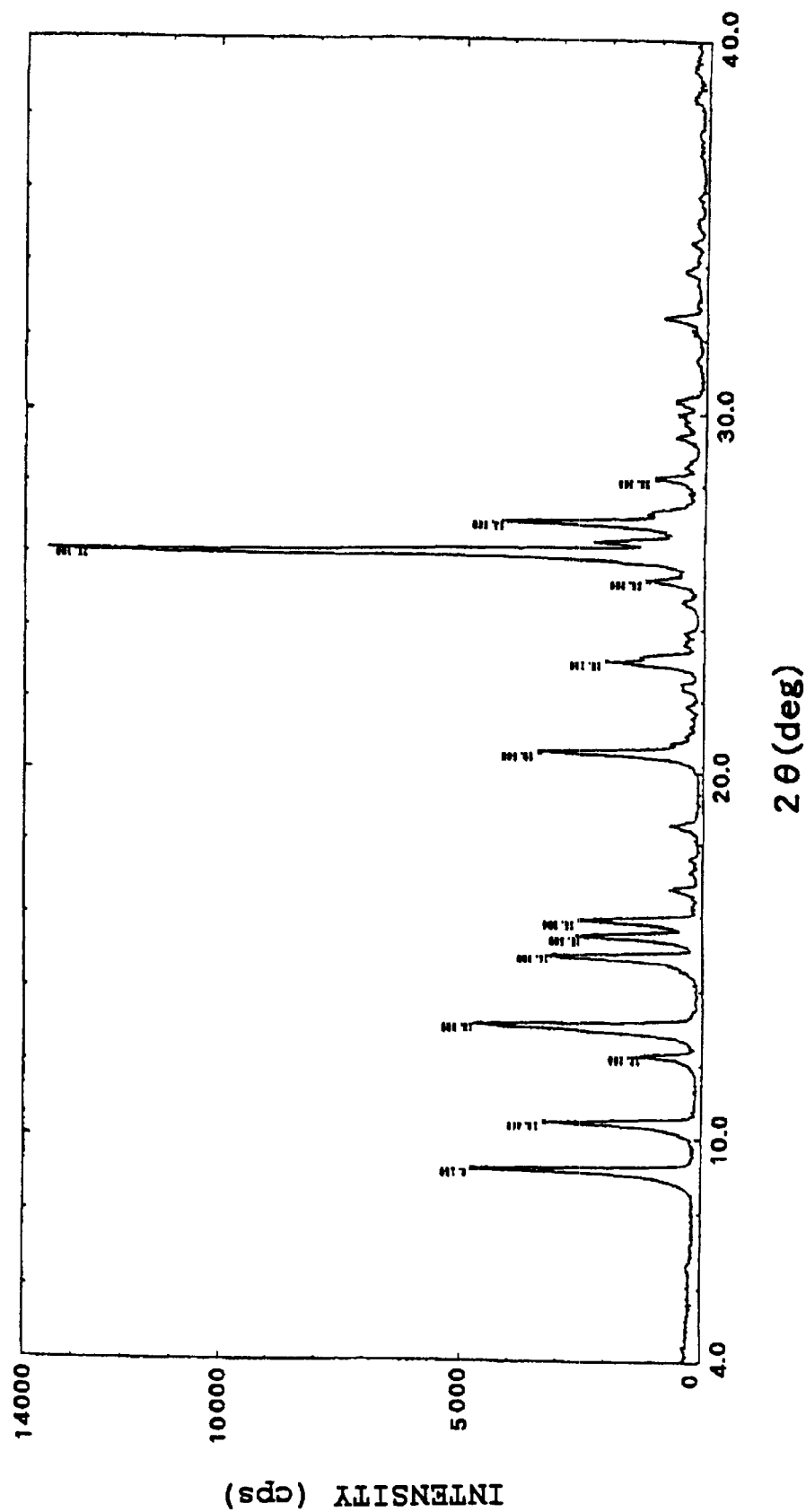
FIG. 1 is an X-ray diffraction spectrum of a reaction product obtained in Example 6.
Figure 2:
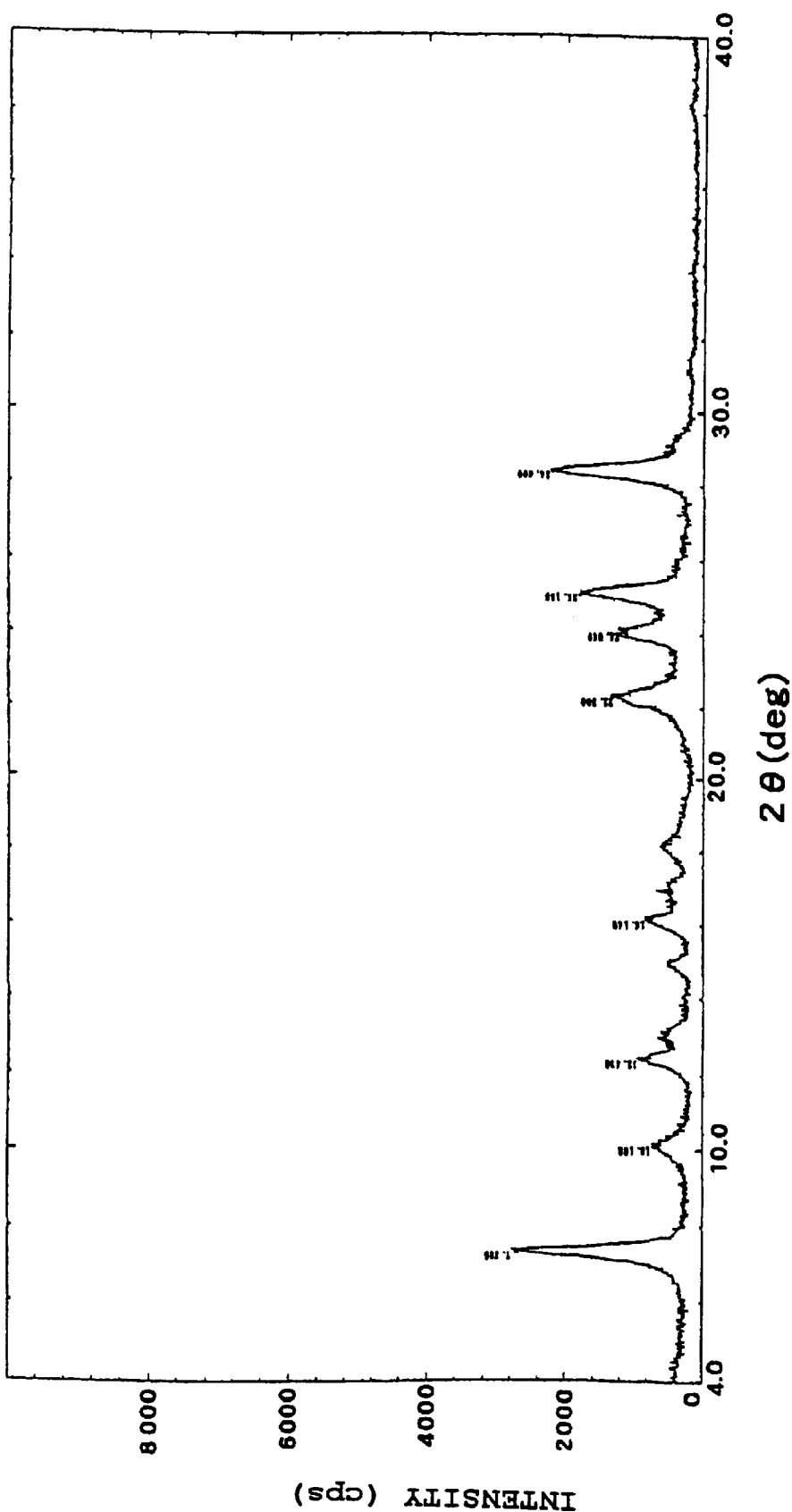
FIG. 2 is an X-ray diffraction spectrum of a reaction product obtained in Example 7.
Figure 3:
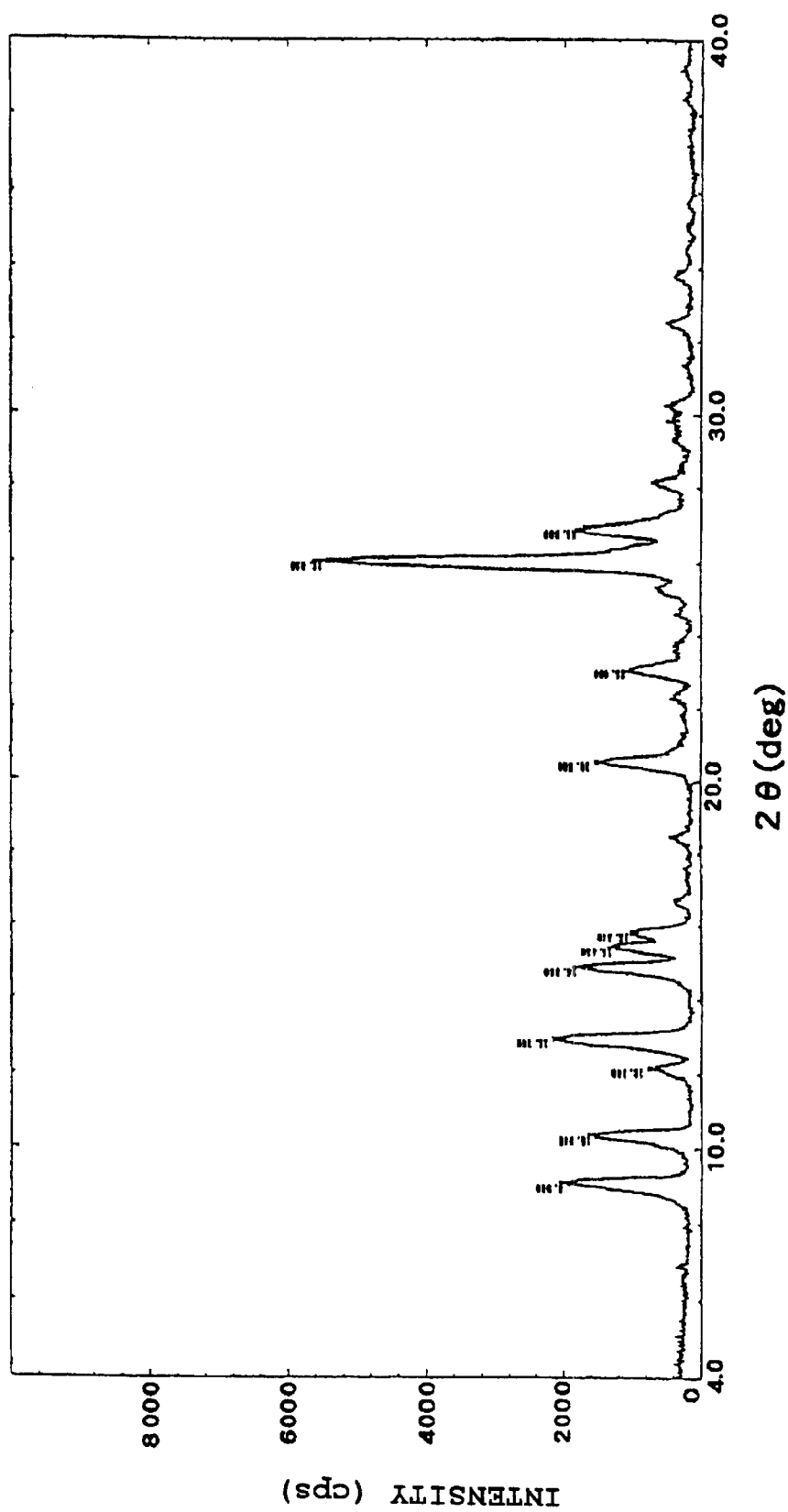
FIG. 3 is an X-ray diffraction spectrum of a reaction product obtained in Example 8.
Figure 4:
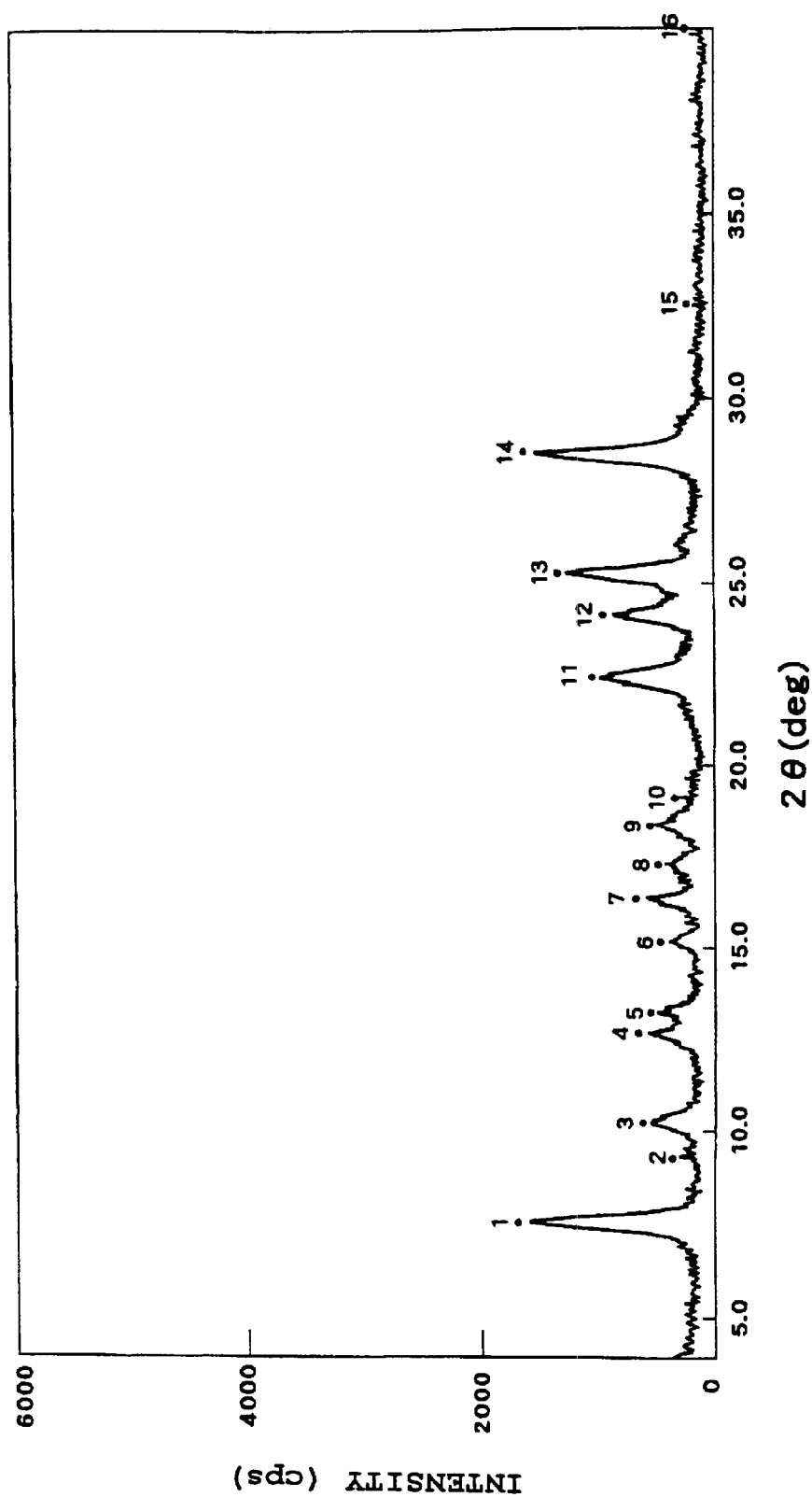
FIG. 4 is an X-ray diffraction spectrum of a reaction product obtained in Example 9.

A first reaction product according to the present invention is a metal-free reaction product capable of being obtained by reacting (i) a nitrile derivative of the above general formula (1) with (ii) a phthalonitrile derivative of the above general formula (2) or a 1,3-diiminoisoindoline derivative of the above formula (3).

A second reaction product according to the present invention is a metal-containing reaction product capable of being obtained by reacting (i) a nitrile derivative of the above general formula (1) with (ii) a phthalonitrile derivative of the above general formula (2) or a 1,3-diiminoisoindoline derivative of the above formula (3) and (iii) with a metal or a metal compound.

In the above formulas (1)–(3), $R_1$–$R_5$ stand, independently from each other, for a hydrogen atom, a halogen atom, an aliphatic hydrocarbyl group, an aromatic group, a hydrocarbyloxy group, a nitro group or a cyano group, with the proviso that two of $R_2$–$R_5$ may link to each other to form a ring.

The aliphatic hydrocarbyl group has a number of carbon atoms of 1–20, preferably 1–10 and may be a chain or cyclic hydrocarbyl group. The chain hydrocarbyl groups includes alkyl and alkenyl groups. Preferred chain aliphatic hydrocarbyl groups include alkyl groups having 1–20 carbon atoms, preferably 1–4 carbon atoms. The cyclic hydrocarbyl groups may be cycloalkyl groups having 5–20 carbon atoms, preferably 6–10 carbon atoms.

A substituent may be bonded to the aliphatic hydrocarbyl group. Such a substituent is inert to the reaction used in the present invention. The substituents may include halogen atoms, alkoxyl groups having 1–6 carbon atoms, a nitro group and a cyano group.

The above aromatic group has an aromatic nucleus of a carbon ring or a hetero ring. The aromatic group having a carbon ring may be a single ring (benzene ring), a polycyclic condensed ring (naphthalene ring, pyrene ring, fluorene ring, anthracene ring, chrysene ring, etc.) or a polycyclic chain ring (biphenyl, terphenyl, etc.). The aromatic group including a hetero ring may be a heteroaromatic group having at least one of hetero atoms such as a nitrogen atom, an oxygen atom and a sulfur atom.

Such aromatic groups may include those having 1–20, preferably 1–10 atoms that constitute the ring. Illustrative of hetero rings are thiophene ring, benzothiophene ring, thianthrene ring, furan ring, benzofuran ring, carbazol ring, pyridine ring, pyrazine ring and pyrrolidine ring.

A substituent may be bonded to the aromatic group. Such a substituent is inert to the reaction used in the present invention. The substituents may include halogen atoms, alkyl groups having 1–6 carbon atoms, alkoxyl groups having 1–6 carbon atoms, a nitro group, a cyano group, a phenyl group and a naphthyl group.

The above hydrocarbyloxy group may be an aliphatic hydrocarbyloxy group or an aromatic hydrocarbyloxy group. The aliphatic hydrocarbyloxy group may be a linear alkoxyl group having 1–20 carbon atoms, preferably 1–10 carbon atoms, or a cyclic alkoxyl group having 1–20 carbon atoms, preferably 1–10 carbon atoms. The aromatic hydrocarbyloxy group may be an alryloxy group having 6–18 carbon atoms, preferably 6–12 carbon atoms, or an arylalkoxyl group having 7–18 carbon atoms, preferably 7–12 carbon atoms.

A substituent may be bonded to the hydrocarbyloxy group. Such a substituent is inert to the reaction used in the present invention. The substituents may include halogen atoms, a nitro group and a cyano group.

Examples of halogen atoms include iodine, bromine, chlorine and fluorine. Examples of aliphatic hydrocarbyl groups which may have a substituent include methyl group, ethyl group, n-propyl group, iso-propyl group, tert-butyl group, sec-butyl group, n-butyl group, iso-butyl group, trifluoromethyl group, 2-cyanoethyl group.

Examples of aromatic groups which may have a substituent include phenyl group, naphthyl group, biphenylyl group, terphenylyl group, pyrenyl group, fluorenyl group, 9,9-dimethyl-2-fluorenyl group, azulenyl group, anthryl group, triphenylenyl group, chrysenyl group, fluorenylidenephenyl group, 5H-dibenzo[a,d]cycloheptenylidenephenyl group, benzyl group, 4-chlorobenzyl group, 4-methylbenzyl group, naphthylmethyl group, thienyl group, benzothienyl group, furyl group, benzofuranyl group, carbazolyl group, pyridyl group, pyridinyl group, pyrrolidyl group and oxazolyl group.

Examples of hydrocarbyloxy groups which may have a substituent include methoxy group, ethoxy group, n-propoxy group, iso-propoxy group, n-butoxy group, iso-butoxy group, sec-butoxy group, tert-butoxy group, 2-hydroxyethoxy group, 2-cyanoethoxy group, benzyloxy group, 4-methylbenzyloxy group and trifluoromethoxy group.

The metal may be an alkali metal or an alkaline earth metal. Illustrative of suitable metals are Mg, Li and Na.

The metal compound may be an alkali metal compound, an alkaline earth metal compound or a transition metal compound. Especially, compounds of metals selected from those belonging to Groups IB, IIB, IIA, IVA, IVB, VB, VIB, VIIB and VIII of the Short Periodic Table are included in the metal compounds.

Illustrative of suitable metal compounds are compounds having a metal such as Na, Li, Cu, Ti, Mg, Co, Mn, Pb, V, Fe, Zn, Ge, Sn, Ni, Al, Ga, Mo or In.

Any kind of conventional metal compounds may be used for the purpose of the present invention. Metal halides and metal alkoxides are suitably used. Examples of the metal compounds may include metal halides such as $TiCl_4$, $CoCl_2$, $CuCl_2$, CuCl, $InCl_3$, $InBr_3$, $AlCl_3$, $GaCl_2$ and $VCl_3$, and metal alkoxides such as $Ti(OBu)_4$ and $Mg(OEt)_2$.

Shown in Tables 1 and 2 are examples of reaction products according to the present invention illustrated in terms of raw materials. The reaction products those obtained by reaction of (i) the compound (1) (nitrile derivative) shown below with the compound (2) (phthalonitrile derivative) shown below and those obtained by reaction of (i) the compound (1) shown below with (ii) the compound (2) shown below and with (iii) metals or metal-containing compounds. In Tables 1 and 2, $R_1$ and n correspond to $R_1$ and n of the compound (1) shown below, while $R_2$–$R_5$ correspond to $R_2$–$R_5$ of the compound (2) shown below.

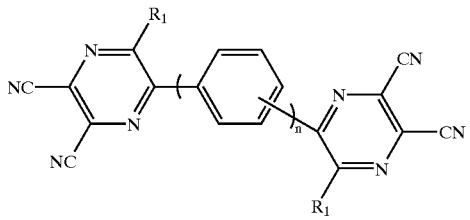

(1)

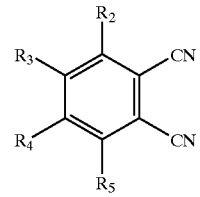

(2)

TABLE 1

| Product No. | $R_1$ | $R_2$ | $R_3$ | $R_4$ | $R_5$ | Metal or metal-containing compound | n |
|---|---|---|---|---|---|---|---|
| 1-A | Ph | H | H | H | H | CuCl | n |
| 1-B | Ph | H | H | H | H | $Ti(OBu)_4$ | 1(1,4-) |
| 1-C | Ph | H | H | H | H | Mg | 1(1,4-) |
| 1-D | Ph | H | H | H | H | $VCl_3$ | 1(1,4-) |
| 1-E | Ph | H | H | H | H | $AlCl_3$ | 1(1,4-) |
| 1-F | Ph | H | H | H | H | $AlCl_3$ | 1(1,3-) |
| 1-G | Ph | H | H | H | H | $AlCl_3$ | 2(1,4-) |
| 1-H | Ph | H | H | H | H | $AlCl_3$ | 2(1,3-) |
| 1-I | Ph | H | H | H | H | $GaCl_2$ | 2(1,2-) |
| 1-J | Ph | H | H | H | H | $GaCl_2$ | 1(1,4-) |
| 1-K | Ph | H | H | H | H | $GaCl_2$ | 1(1,3-) |
| 1-L | Ph | H | H | H | H | $CoCl_2$ | 2(1,4-) |
| 1-M | Ph | H | H | H | H | $InCl_3$ | 1(1,4-) |
| 1-N | Ph | H | H | H | H | $InBr_3$ | 1(1,3-) |
| 2-A | H | H | H | H | H | CuCl | 2(1,4-) |
| 2-B | H | H | H | H | H | $Ti(OBu)_4$ | 2(1,3-) |
| 2-C | H | H | H | H | H | Mg | 1(1,4-) |
| 2-D | H | H | H | H | H | $Ti(OBu)_4$ | 1(1,4-) |
| 3-A | Ph | F | F | F | F | CuCl | 1(1,3-) |
| 3-B | Ph | F | F | F | F | $Ti(OBu)_4$ | 1(1,4-) |
| 3-C | Ph | F | F | F | F | Mg | 1(1,3-) |
| 3-D | Ph | F | F | F | F | $VCl_3$ | 1(1,4-) |
| 4-A | F | F | F | F | F | $CuCl_2$ | 1(1,4-) |
| 4-B | F | F | F | F | F | $Ti(OBu)_4$ | 1(1,4-) |
| 4-C | F | F | F | F | F | Mg | 1(1,4-) |
| 4-D | F | F | F | F | F | $VCl_3$ | 1(1,3-) |

TABLE 2

| Product No. | $R_1$ | $R_2$ | $R_3$ | $R_4$ | $R_5$ | Metal or metal-containing compound | n |
|---|---|---|---|---|---|---|---|
| 5A | Me | H | H | H | H | $Ti(OBu)_4$ | 1(1,4-) |
| 6A | Me | F | F | F | F | $Ti(OBu)_4$ | 1(1,4-) |
| 7A | Ph | H | (benzo-fused) | | H | $Ti(OBu)_4$ | 1(1,4-) |
| 8A | H | H | (benzo-fused) | | H | $TiCl_4$ | 1(1,4-) |
| 9A | H | H | Me | H | H | $Ti(OBu)_4$ | 1(1,4-) |

TABLE 2-continued

| Product No. | R₁ | R₂ | R₃ | R₄ | R₅ | Metal or metal-containing compound | n |
|---|---|---|---|---|---|---|---|
| 10A | Ph | H | Me | H | H | Ti(OBu)₄ | 1(1,4-) |
| 12-A | Ph | H | H | H | H | — | 1(1,4-) |
| 12-B | Ph | H | H | H | H | — | 1(1,3-) |
| 12-C | Ph | H | H | H | H | — | 2(1,4-) |
| 12-D | Ph | H | H | H | H | — | 2(1,3-) |
| 12-E | Ph | H | H | H | H | — | 2(1,2-) |
| 12-F | Ph | H | H | H | H | — | 1(1,4-) |
| 12-G | Ph | H | H | H | H | — | 1(1,3-) |
| 12-H | Ph | H | H | H | H | — | 2(1,4-) |
| 12-I | H | H | H | H | H | — | 2(1,3-) |
| 12-J | H | H | H | H | H | — | 1(1,4-) |
| 12-K | Ph | F | F | F | F | — | 1(1,4-) |
| 12-L | Ph | F | F | F | F | — | 1(1,3-) |
| 12-M | F | F | F | F | F | — | 1(1,4-) |
| 12-N | F | F | F | F | F | — | 1(1,3-) |
| 12-O | F | F | F | F | F | — | 1(1,4-) |
| 12-P | Me | H | H | H | H | — | 1(1,4-) |
| 12-Q | Me | F | F | F | F | — | 1(1,4-) |
| 12-R | Ph | H | —benzo— | | H | — | 1(1,4-) |
| 12-S | H | H | —benzo— | | H | — | 1(1,4-) |
| 12-T | H | H | Me | H | H | — | 1(1,4-) |
| 12-U | Ph | H | Me | H | H | — | 1(1,4-) |

The reaction products shown in Tables 1 and 2 may be obtained by reacting the above nitrile derivative with the above phthalonitrile compound and, if necessary, with a metal or a metal-containing compound without using a solvent or in the presence of a solvent. The reaction temperature is generally from room temperature to 300° C., especially from 40° C. to 200° C. The use of such a temperature is preferred for reasons of reduced by-products and from the standpoint of yield.

The solvent may be a halogenated hydrocarbon such as α-chloronaphthalene, dichlorobenzene or trichlorobenzene, an alcohol such as pentanol or octanol, an amine such as N,N-dimethylformamide or N-methylpyrrolidone, or an aromatic hydrocarbon such as benzene, toluene or nitrobenzene.

The amount of the phthalonitrile derivative (compound 2) is 6–4000 moles, preferably 6–1,600 moles, more preferably 6–800 moles, per mole of the nitrile derivative (compound 1). The amount of the metal or metal compound is 0.001–100 moles, preferably 0.1–10 moles, more preferably 0.25–1.0 mole, in terms of metal, per mole of the nitrile derivative.

When a solvent is used, the amount thereof is 50–3000 parts by weight, preferably 200–1500 parts by weight, per 100 parts by weight of the nitrile derivative.

The reaction product according to the present invention may be a product obtained by reacting (i) a nitrile derivative of the general formula (1) shown below with (ii) a 1,3-diiminoisoindoline derivative of the general formula (3) shown below or a product obtained by reacting (i) a nitrile derivative of the general formula (1) shown below with (ii) a 1,3-diiminoisoindoline derivative of the general formula (3) shown below in the presence of (iii) a metal or a metal compound.

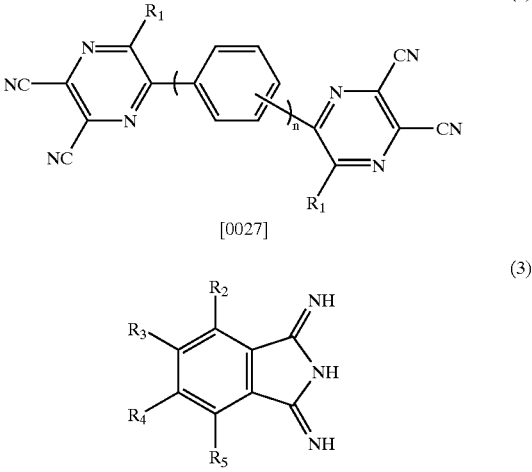

[0027]

The reaction of the nitrile derivative with the 1,3-diiminoisoindoline derivative can be performed in the same manner as that of the reaction between the nitrile derivative and the phthalonitrile derivative. The reaction temperature is especially 70–300° C., preferably 100–140° C. The amount of the 1,3-diiminoisoindoline derivative is 6–4000 moles, preferably 6–1600 moles, more preferably 6–800 moles, per mole of the nitrile derivative.

The phthalonitrile compound (2) and the 1,3-diiminoisoindoline (3) may be obtained by a known method disclosed in "Phthalocyanine, Chemistry and Function" by Shirai and Kobayashi. Some of them are also commercially available.

The nitrile compound (1) may be prepared according to the following reaction:

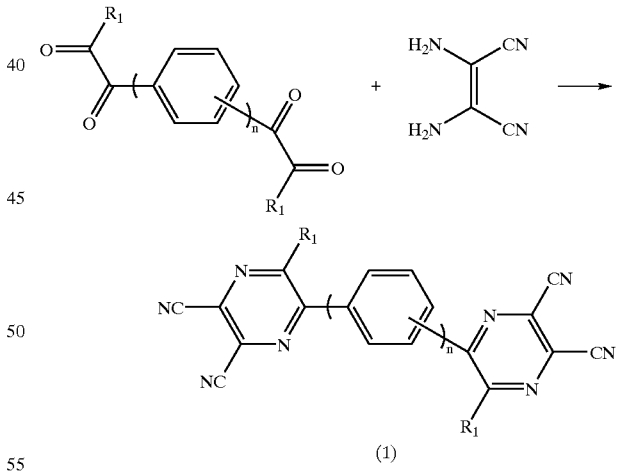

wherein n is an integer of 1 or 2.

The above reaction may be carried out with heating generally in the absence of a solvent or in the presence of a solvent such as an alcohol, e.g. ethanol, butanol, pentanol or octanol, an aromatic hydrocarbon, e.g. benzene, toluene or nitrobenzene, a halogenated hydrocarbon, e.g. □-chloronaphthalene, dichlorobenzene or trichlorobenzene, an acidic solvent, e.g. acetic acid, or an amine, e.g. N,N-dimethylformamide or 1-methyl-2-pyrrolidinone. For reasons of improving reaction yield and solubility of reaction raw materials, it is preferred that the reaction be performed in the presence of an acid catalyst such as acetic acid, sulfuric acid or hydrochloric acid. The above reaction is performed at a temperature of generally from room temperature to 300° C. The use of a reaction temperature from 100° C. to 180° C. is preferred from the standpoint of yield.

The reaction of the nitrile compound (1) with the naphthonitrile compound (2) or 1,3-diiminoisoindoline (3) may be carried out in the presence of an amine catalyst such as urea, formamide or 1,8-diazabicyclo[5,4,0]undecene (DBU). The amine catalyst may be used in an amount of 0.1–100 moles, preferably 0.1–5 moles, per mole of the nitrile derivative.

The product obtained by the reaction of the nitrile compound of the above general formula (1) with the phthalonitrile compound of the above general formula (2) or 1,3-diiminoisoindoline of the above general formula (3) and, if necessary, with the metal or metal-containing compound is a solid at room temperature. The color is green to dark blue depending upon the composition of the product and is suitable as an organic pigment.

The reaction product according to the present invention may be crystalline solid. The crystalline solid does not have a melting point but decomposes at 400° C. or more to cause reduction of mass. The crystal structure of the crystalline solid may be converted, if desired, into another crystal structure by a crystal converting treatment.

As a method of converting crystal structure to obtain a reaction product having a different crystal structure, conventional methods, such as an acid treatment, a solvent treatment, a mechanical treatment, a heat treatment, a milling treatment and a combination of these treatments, may be used.

In the acid treatment, a solid (reaction product) is dissolved in an acid, such as sulfuric acid, trichloroacetic acid or trifluoroacetic acid, or a mixture of such an acid with an organic solvent preferably at a temperature of 0° C. to room temperature. The solution thus obtained is then added dropwise to ice water, water or an organic solvent or a mixed organic solvent in which the reaction product is insoluble or hardly soluble, so that solids are precipitated. The solid product is separated by filtration or the like method to obtain a reaction product.

In the solvent treatment, a solid (reaction product) is suspended with stirring in an organic solvent, water or a mixture thereof at room temperature or at an elevated temperature. The organic solvent may be, for example, an aromatic hydrocarbon such as benzene, toluene, dichlorobenzene or nitrobenzene, an alcohol such as methanol, ethanol, n-propanol, n-butanol or n-pentanol, a ketone such as acetone, cyclohexanone or methyl ethyl ketone, an ether such as n-butyl ether, ethylene glycol n-butyl ether or tetrahydrofuran, an amine such as N,N-dimethylformamide, N-methylpyrrlidone or quinoline, an ester such as methyl acetate, ethyl acetate or n-butyl acetate, or a nitrogen-containing solvent such as 2-pyrrolidinone, 1-methyl-2-pyrrolidinone, 5-methyl-2-pyrrolidinone, 1,5-dimethyl-2-pyrrolidinone, 1,3-dimethyl-2-imidazolidinone, 2-imidazolidinone or 1-(2-hydroxyethyl)-2-imidazolidinone.

The amount of the organic solvent is desirably at least 5 times, more preferably 5–100 times, the volume of the solid of the reaction product for reasons of facilitating stirring and of obtaining uniform crystals. When one or more organic solvents are used by themselves, the solvent treatment is generally performed at a temperature of 250° C. or less. When water and an organic solvent are used for the solvent treatment, they can be mixed with the reaction product in any desired order. Water and an organic solvent may be mixed in a reactor so that the reaction product can be added to the organic solvent in which water is dissolved in a saturated amount in the initial stage and is surely present. The reaction product which has been subjected to the above acid treatment may be subsequently treated with an organic solvent or a mixture of two or more organic solvents, as such without being dried, at room temperature or an elevated temperature. The temperature at which the heat treatment is carried out is 50–200° C., preferably 50–150° C. The treatment time is not specifically limited but is desired to be such that the mixture can be sufficiently stirred homogeneously. The reaction product subjected to the above acid treatment may be dried before the solvent treatment.

In the milling treatment, the reaction product is treated at ambient temperature or an elevated temperature with a milling device such as sand mill or ball mill using glass beads, steel beads or alumina balls. The milling treatment may be carried out using the above milling medium together with a solvent.

The reaction product according to the present invention can be an amorphous solid. The amorphous solid also decomposes at 400° C. or more.

As the method of obtaining an amorphous reaction product, there may be mentioned, for example, an acid treatment and a mechanical treatment. One acid treatment is an acid paste method in which a solid reaction product is added little by little to an acid, such as sulfuric acid, trichloroacetic acid or trifluoroacetic acid, at a temperature of not higher than room temperature, preferably 0° C. to room temperature, with stirring, to dissolve the solid therein. The solution thus obtained is then added dropwise to ice, water or an organic solvent or a mixed organic solvent in which the solid product is not or scarcely soluble, thereby precipitating the reaction product which is thereafter collected by filtration. It is preferred that the above solution or dispersion be added to ice or ice water, especially ice water. Further, it is preferred that the above solution be added to vigorously stirred ice water for quickly diffusing the solution into the ice water.

The mechanical treatment may be a milling treatment in which the solid product is treated with a milling device such as sand mill or ball mill using glass beads, steel beads or alumina balls at room temperature or an elevated temperature.

Whether or not the product is amorphous can be confirmed by a diffraction pattern in X-ray analysis. When the product is amorphous, no sharp peaks are present in the X-ray diffraction pattern using $CuK_\alpha$ ray. In the present specification, the term "sharp peak" is intended to refer to a peak having a half-width value of not greater than 1°. Thus, a product which does not provide, in X-ray analysis thereof, an X-ray diffraction pattern having a diffraction peak of not greater than 1° is an amorphous product.

A product obtained by the reaction of the nitrile compound (1) with the phthalonitrile compound (2) and, optionally, with the metal or metal-containing compound in the presence of an organic solvent is generally a crystalline product. Thus, when the crystalline product is to be converted into a product having a different crystal structure, it is preferred that the reaction product be first subjected to an acid treatment for the conversion of the crystalline product into amorphous product and then to a solvent treatment, because the conversion of the crystal structure can be easily performed.

For the production of a reaction product having various different crystal structures, it is effective that a crystalline or amorphous product be subjected a treatment with an organic solvent (as described above) with stirring at room temperature or an elevated temperature, preferably at 50° C. or less. An acid treatment is also effective. In the acid treatment, the reaction product is dissolved little by little in an acid such as sulfuric acid, trichloroacetic acid, trifluoroacetic acid or a mixture of such an acid with an organic solvent at a temperature of 0° C. to room temperature. The solution thus obtained is then added dropwise to water, ice water, ice or an organic solvent or a mixed organic solvent in which the product is insoluble or hardly soluble, so that the reaction product is precipitated. The treated product is separated by filtration.

It is possible to obtain a reaction product having different crystal structures by controlling the treatment conditions, such as kind of solvent, treatment time and treatment temperature, of the solvent treatment or acid treatment. The reaction product having different crystal structures can be confirmed by a diffraction pattern in X-ray diffraction analysis.

The crystalline reaction product according to the present invention is featured by having charge generating properties. While a reaction product having any crystal structure can exhibit charge generating properties, it is preferred that the product provide a $CuK_\alpha$ X-ray diffraction pattern having strong diffraction peaks at a Bragg angle $2\theta \pm 0.2°$ of in the range of 20°–30°, more preferably a $CuK_\alpha$ X-ray diffraction pattern having strong diffraction peaks at a Bragg angle $2\theta \pm 0.2°$ of 27.2°, most preferably a $CuK_\alpha$ X-ray diffraction pattern having strong diffraction peaks at a Bragg angle $2\theta \pm 0.2°$ of 27.2° but no diffraction peaks at a Bragg angle $2\theta \pm 0.2°$ of in the range of 4°–10°, for reasons of exhibiting excellent charge generating efficiency and good electrophotographic characteristics.

The reaction product providing a $CuK_\alpha$ X-ray diffraction pattern having strong diffraction peaks at a Bragg angle $2\theta \pm 0.2°$ of 27.2° but no diffraction peaks at a Bragg angle $2\theta \pm 0.2°$ of in the range of 4°–10° will be described in detail below. The term "a diffraction pattern having no diffraction peaks at a Bragg angle $2\theta \pm 0.2°$ of in the range of 4°–10°" used herein is intended to refer to a $CuK_\alpha$ X-ray diffraction pattern which does not have, in a Bragg angle $2\theta \pm 0.2°$ of in the range of 4°–10°, any peak attributed to crystals, any low intensity peak with a broad half-width value attributed to fine crystals, and any such a low intensity halo (which is not a clear peak) as seen in a glassy state material. When the product has such a peak attributed to crystals or fine crystals or a halo at a Bragg angle $2\theta \pm 0.2°$ of in the range of 4°–10°, there is a fear the resulting electrophotoconductive properties are adversely affected due to a change of the crystal structure caused during a crystal treatment in an organic solvent or upon lapse of time. Although the cause is not clear, it is inferred that crystals or fine crystals which causes a peak or halo at a Bragg angle $2\theta \pm 0.2°$ of in the range of 4°–10° serve as a seed crystal to alter the crystal structures. On the other hand, a reaction product providing a diffraction pattern having no diffraction peaks at a Bragg angle $2\theta \pm 0.2°$ of in the range of 4°–10° has excellent stability and can retain its crystal structures even when stored in an organic solvent. Thus, a coating liquid for use in coating of a photoconductive layer of an electrophotographic photoconductor permits long period storage, ensuring reduction in manufacturing costs.

For the production of a reaction product having no of 4°–10°, it is preferable to use a mixture of trifluoroacetic acid with an organic solvent, more preferably a mixture of trifluoroacetic acid with a chlorine-containing solvent for the treatment of the reaction product. The chlorine-containing organic solvent may be, for example, chloroform, dichloromethane or 1,2-dichloroethane. The mixing ratio of the organic solvent to the acid is 0.1:99.9 to 99.9:0.1, preferably 0.5:99.5 to 99.5:0.5, more preferably 1:9 to 9:1 for reasons of solubility of the reaction product in the mixed liquid and for conversion of the whole reaction product into desired crystals. The product is dissolved little by little in the mixture of trifluoroacetic acid with a chlorine-containing solvent. The solution thus obtained is then added dropwise to an organic solvent or a mixed organic solvent in which the above product is insoluble or hardly soluble, so that the reaction product is precipitated. While any organic solvent as the above organic solvent may be used, the use of a mixed solvent containing a chlorine-containing and an alcohol is preferred. The chlorine-containing solvent may be chloroform, dichloromethane or 1,2-dichloroethane, while the alcohol may be methanol or ethanol.

The crystalline reaction product according to the present invention has charge generating properties and, hence, is suitably used as a charge generating material for electrophotographic photoconductors. When the crystalline reaction product is dispersed in a binder and is formed into a film, the film can absorb light of a near infrared region, i.e. a wavelength in the range of 500–700 nm, which corresponds to the wavelength of light emitted from laser diodes (LD). Thus, with the use of the product according to the present invention as a charge generating material, it is possible to obtain an electrophotographic photoconductor having high sensitivity.

The product according to the present invention can be confirmed by mass spectrometry. For example, when the nitrile derivative A of the following formula (6), the phthalonitrile of the formula (7) and $Ti(OBu)_4$ as a metal-containing compound are reacted, there is obtained a reaction product providing a mass spectrum having a peak at $1383 \pm 1$.

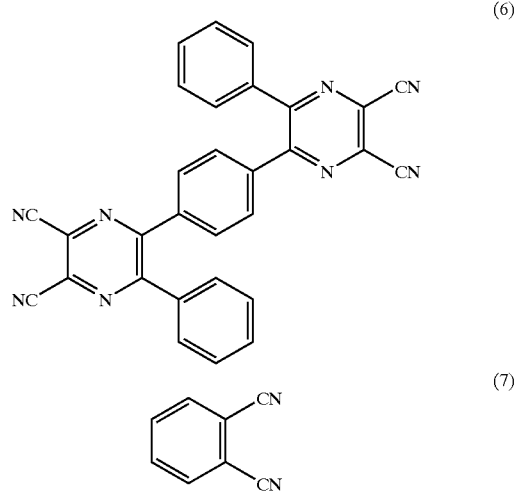

(6)

(7)

Thus, the above reaction product would contain the compounds of the following formulas (8) and (9). The mass spectrometry of the reaction product gives fragment peaks corresponding to the molecular weight of $1383 \pm 1$ attributed to the compound (8) and the molecular weight of $576 \pm 1$ attributed to the compound (9), from which the reaction product according to the present invention can be confirmed.

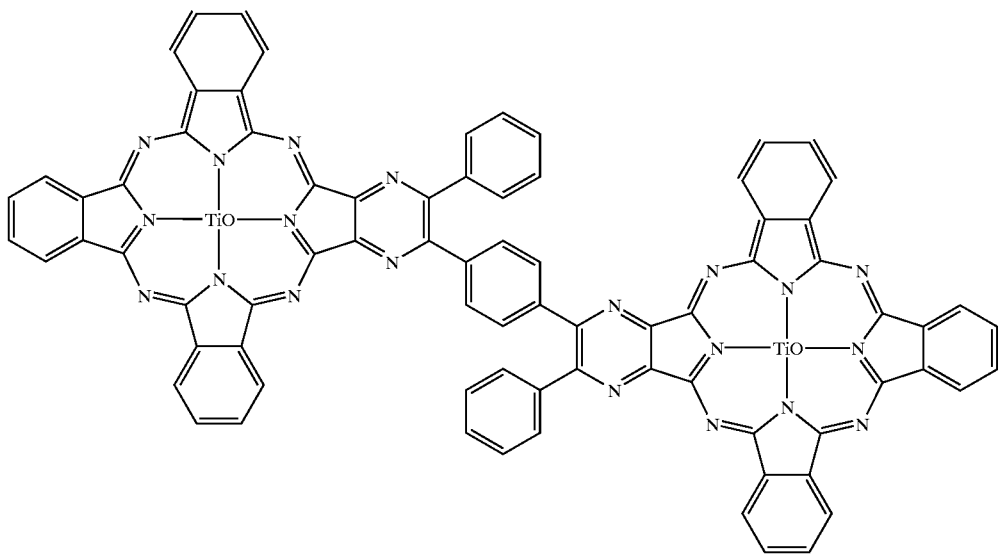

(8)

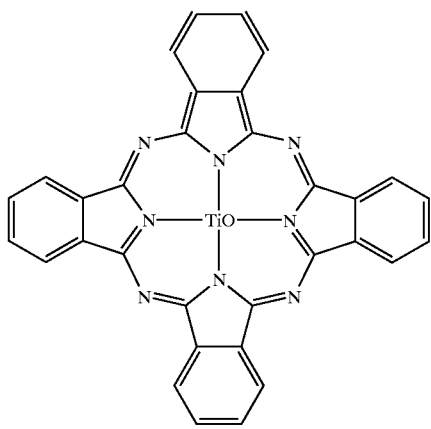

(9)

Additionally, X-ray fluorescent elementary analysis can detect Ti in the reaction product.

An electrophotographic photoconductor of a single-layered type or a layered type (function-separating type) can be fabricated, using the crystalline product (pigment) having charge generating properties according to the present invention alone or in combination with a charge transport material. To fabricate the electrophotogracphic photoconductor of a single-layered type, a photoconductive layer is provided on an electroconductive support in such a manner that the solvent-treated product is dispersed in a binder resin singly or together with a charge transport material. In the case of a layered type (function-separating type), a charge generation layer comprising the solvent-treated product is provided on an electroconductive support, and a charge transport layer comprising a charge transporting material is overlaid on the charge generation layer. The charge generation layer and the charge transport layer may be laminated in reversed order.

An intermediate layer may be provided between the support and the photoconductive layer for the purpose of improving the adhesion and for enhancing the charge blocking characteristics. Furthermore, a protective layer may be provided on the photoconductive layer to improve the mechanical durability, such as wear resistance.

The photoconductive layer may be prepared by dissolving or dispersing the solvent-treated reaction product in a suitable solvent optionally together with a binder, the resulting liquid being applied and dried.

As a method for dispersing the crystalline reaction product having charge generating properties according to the present invention, there may be mentioned a ball mill, ultrasonic wave or a homomixer. The application of the coating liquid may be by dip coating, blade coating or spray coating.

To upgrade the dispersibility of the reaction product in the photoconductive layer for the preparation of the photoconductive layer, it is preferable that the average particle size of the reaction product be 2 $\mu$m or less more preferably 1 m$\mu$ or less. The lower limit of the average particle size is preferably 0.01 m$\mu$, because too small a particle diameter causes aggregation of fine particles, increase of the resistivity of the photoconductive layer, deterioration of sensitivity and durability due to an increase of defective crystallites and limitation of fine pulverization.

Specific examples of the solvent which is used to prepare a dispersion or solution for the formation of the photoconductive layer include N,N-dimethylformamide, toluene, xylene, monochlorobenzene, 1-methyl-2-pyrrlidinone, 1,2-dichloroethane 1,1,1-trichloroethane, dichloromethane, 1,1,2 trichloroethane, trichloroethylene, tetrahydrofuran, methyl ethyl ketone, methyl isobutyl ketane, cyclohexanone, ethyl acetate, butyl acetate and dioxane.

Any binder resin that has good electrically insulating properties and conventionally used in the preparation of the electrophotographic photoconductor can be employed for the formation of the photoconductive layer in the present invention. Specific examples of such a binder resin include addition polymerization-type resins, polyaddition-type resins and polycondensation-type resins such as polyethylene, polyvinyl butyral, polyvinyl formal, polystyrene resin, phenoxy resin, polypropylene, acrylic resin, methacrylic resin, vinyl chloride resin, vinyl acetate resin, epoxy resin, polyurethane resin, phenolic resin, polyester resin, alkyd resin, polycarbonate resin, polyamide resin, silicone resin and melamine resin; copolymer resins comprising as the repeating units two or more monomers for use in the above-mentioned resins, for example, electrically insulating resins such as vinyl chloride-vinyl acetate copolymer resin, styrene-acrylic copolymer resin, and vinyl chloride-vinyl acetate-maleic anhydride copolymer resin; and a polymeric organic semiconductor such as poly-N-vinylcarbazole. These binder resins may be used alone or in combination.

The crystalline reaction product (pigment) according to the present invention may be used as a mixture with another pigment such as a phthalocyanine pigment according to required characteristics of the photoconductor.

The mixing method is not specifically limited and may be carried out by various suitable methods.

Examples of such mixing methods include (1a) a method in which the reaction product of the present invention is mechanically milling with a phthalocyanine pigment by a conventional method, (2a) a method in which the reaction product of the present invention is mixed with a phthalocyanine pigment using a conventional mixing device such as a tumbler for use in mixing powders, (3a) a method in which the reaction product of the present invention is mixed with a phthalocyanine pigment in a suitable organic solvent such as xylene using a mixer, (4a) a method in which the reaction product of the present invention and a phthalocyanine pigment are added to a binder resin and dispersed using a device such as ball mill or sand mill, (5a) a method in which the reaction product of the present invention and a phthalocyanine pigment is dispersed in a binder resin, followed by addition of the reaction product or the phthalocyanine pigment, and (6a) a method in which the reaction product of the present invention and a phthalocyanine pigment are mixed in an inorganic acid such as sulfuric acid, phosphoric acid, acetic acid or an organic acid such as trifluoroacetic acid, followed by coprecipitation with water or an alkaline substance. The present invention is not limited to the above methods.

The mixing ratio of the product to the phthalocyanine pigment is, in terms of molar ratio, preferably 0.001:99.999 to 99.999:0.001, more preferably 0.1:99.9 to 99.9:0.1, for reasons of prevention of an increase in residual potential and a reduction of chargeability during repeated use.

Examples of the phthalocyanine pigment for use in the present invention include metal-free phthalocyanine, metal phthalocyanine or a mixture thereof. The metal phthalocyanine may be copper phthalocyanine, aluminum phthalocyanine, magnesium phthalocyanine, chlorogallium phthalocyanine, hydroxygallium phthalocyanine, vanadyl phthalocyanine, titanyl phthalocyanine, chloroindium phthalocyanine, hydroxyindium phthalocyanine, zinc phthalocyanine, iron phthalocyanine or cobalt phthalocyanine but is not limited to the above.

The reaction product according to the present invention may be also used in combination with other pigments than phthalocyanine pigment as follows: organic pigments, for example, azo pigments such as C.I. Pigment Blue 25 (C.I. 21180), C.I. Pigment Red 41 (C.I. 21200), C.I. Acid Red 52 (C.I. 45100), C.I. Basic Red 3 (C.I. 45210), an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application 53-132347), an azo pigment having a dibenzothiophene skeleton (Japanese Laid-Open Patent Application 54-21728), an azo pigment having an oxadiazole skeleton (Japanese Laid Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); indigo pigments such as C.I. Pigment Blue 16 (C.I. 74100) C.I. Vat Brown 5 (C.I. 73410) and C.I. Vat Dye (C.I. 73030); and perylene pigments such as Algol Scarlet B and Indanthrene Scarlet R (made by Bayer Co. Ltd.). Two or more organic pigments mentioned above may be used.

In fabrication of a photoconductor using the above layer constitution and substances, there are preferred ranges for the film thickness and the amount of the substances. In the case of a function separation type (support/charge generation layer/charge transport layer), a binder is used as required in the charge generation layer. In this case, the amount of the reaction product is preferably at least 20% by weight based on the binder and the thickness of the charge generation layer is preferably in the range of 0.01 to 5 $\mu$m. In the charge transport layer, the amount of the charge transport material is preferably in the range of 20 to 200 wt % based on the binder and the thickness of the charge transport layer is preferably in the range of 5 to 100 $\mu$m. The charge transport layer may be formed using a high-molecular weight charge transport material alone.

It is preferred that the charge generation layer contain a charge transport material for reasons of reducing the residual potential and improving the sensitivity. The charge transport material is preferably used in an amount of 20 to 200% by weight based on the binder.

In the single-layered photoconductive layer, it is preferable that the amount of the reaction product of the present invention be in the range of 5 to 95% by weight based on the binder resin for use in the photoconductive layer. In this case, the thickness of the single-layered photoconductive layer is preferably in the range of 10 to 100 $\mu$m. When a charge transport material is added to the single-layered photoconductive layer, it is preferable that the amount of the charge transport material be in the range of 30 to 200% by weight based on the binder resin. There can be employed a photoconductive layer comprising a high-molecular weight charge transport material and the product according to the present invention. In this case, it is preferable that the amount of the product be in the range of 5 to 95% by weight based on the high-molecular weight charge transport material. In this case, it is preferable that the thickness of the photoconductive layer be in the range of 10 to 100 $\mu$m.

To improve the chargeability, the photoconductive layer may further comprise a phenol compound, a hydroquinone compound, a hindered phenol compound, a hindered amine compound, and a compound having a hindered amine and a hindered phenol in a molecule thereof.

As the electroconductive support, there can be employed a metallic plate, drum or foil made of aluminum, nickel, copper, titanium, gold or stainless steel; a plastic film on which an electroconductive material such as aluminum, nickel, copper, titanium, gold, tin oxide or indium oxide is deposited; and a sheet of paper or a plastic film, which may be formed in a drum, coated with an electroconductive material.

An intermediate layer may be provided on the electroconductive support. The intermediate layer comprises a resin as the main component. Since the photoconductive layer is provided on the intermediate layer by a coating method using a solvent, it is desirable that the resin for use in the intermediate layer have high resistance against general-purpose organic solvents. Preferable examples of the resin for use in the intermediate layer include water-soluble resins such as polyvinyl alcohol, casein and sodium polyacrylate; alcohol-soluble resins such as copolymer nylon and methoxymethylated nylon; and hardenable resins with three-dimensional network such as polyurethane, melamine resin, phenolic resin, alkyd-melamine resin and epoxy resin. The undercoat layer may further comprise finely-divided particles of metallic oxides such as titanium oxide, silica, alumina, zirconium oxide, tin oxide and indium oxide in order to prevent the occurrence of moire and reduce the residual potential. Similar to the previously mentioned photoconductive layer, the intermediate layer can be provided on the electroconductive support by coating method, using an appropriate solvent. Further, the intermediate layer for use in the present invention may be prepared using a coupling agent such as a silane coupling agent, titanium coupling agent or chromium coupling agent. Furthermore, to prepare the intermediate layer, $Al_2O_3$ may be deposited on the electroconductive support by anodizing process, or an organic material such as poly-para-xylylene (parylene), or an inorganic material such as $SiO_2$, $SnO_2$, $TiO_2$, ITO or $CeO_2$ may be deposited on the electroconductive support by vacuum thin film forming method. It is proper that the thickness of the intermediate layer be 5 μm or less.

Examples of a resin for use as a material for the formation of the protective layer include ABS resin, ACS resin, copolymer of olefin and vinyl monomer, chlorinated polyether, allyl resin, phenolic resin, polyacetal polyamide, polyamideimide, polyacrylate, polyallyl sulfone, polybutylene, polybutylene terephthalate, polycarbonate, polyether sulfone, polyethylene, polyethylene terephthalate, polyimide, acrylic resin, polymethylpentene, polypropylene, polyphenylene oxide, polysulfone, polystyrene, AS resin, butadiene-styrene copolymer, polyurethane, polyvinyl chloride, polyvinylidene chloride and epoxy resin. The protective layer may further comprise a fluorine-containing resin such as polytetrafluoroethylene, and a silicone resin to improve the abrasion resistance. In addition, inorganic materials such as titanium oxide, tin oxide and potassium titanate may be dispersed in the above mentioned fluorine-containing resin and silicone resin. The protective layer may be provided on the photoconductive layer by the conventional coating method. The thickness of the protective layer is preferably in the range of about 0.1 to 10 μm. Furthermore, a vacuum-deposited thin film of a-C or a-SiC may be used as the protective layer in the present invention.

The charge transport materials include a positive hole transport material and an electron transport material.

The positive hole transport materials may be, for example, poly-N-carbazole and derivatives thereof, poly-γ-carbazolyl ethylglutamate and derivatives thereof, a condensation product of pyrene and formaldehyde and derivatives thereof, polyvinyl pyrene, polyvinyl phenanthrene, oxazole derivatives, imidazole derivatives and triphenylamine derivatives. Stilbene compounds of the following formula (4) may also be suitably used for reasons of excellent charge transporting properties:

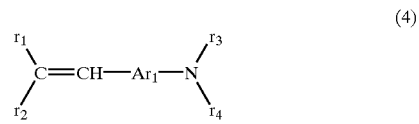

(4)

wherein $r_1$ and $r_2$ stand, independently from each other, for a substituted or unsubstituted alkyl group or a substituted or unsubstituted aryl group, $r_3$ and $r_4$ stand, independently from each other, for a hydrogen atom, a substituted or unsubstituted alkyl group, a substituted or unsubstituted aryl group, or a heterocyclic group, with in the proviso that $r_1$ and $r_2$ may together form a ring, and $Ar_1$ stands for a substituted or unsubstituted aryl group or a heterocyclic group.

Illustrative of suitable stilbene compounds are shown in Tables 3–12. The present invention is not limited to these compounds. In Tables 3–12, $R_1$, $R_2$, $Ar_1$, $R_3$ and $R_4$ represent those corresponding to the above general formula (4).

TABLE 3

| Compound No. | $R_1$ | $R_2$ | $Ar_1$ | $R_3$ | $R_4$ |
|---|---|---|---|---|---|
| 1 | $CH_3$ | $CH_3$ | 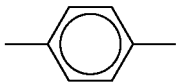 | 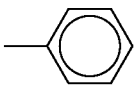 | 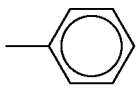 |
| 2 | H | 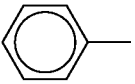 | " | " | " |
| 3 | " | 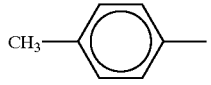 | " | " | " |

TABLE 3-continued
| Compound No. | R₁ | R₂ | Ar₁ | R₃ | R₄ |
|---|---|---|---|---|---|
| 4 | " | " | " | 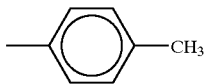 | " |
| 5 | " | " | " | 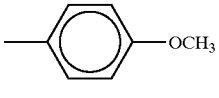 | " |
| 6 | " | " | " |  | " |
| 7 | " | " | " | 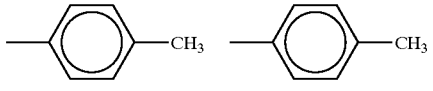 | 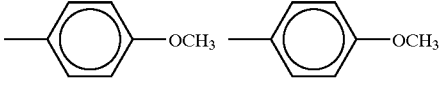 |
| 8 | " | " | " | 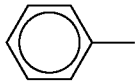 | 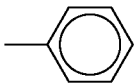 |
| 9 | CH₃ | 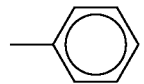 | " | 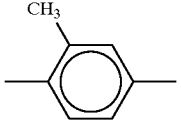 | 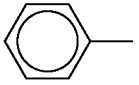 |
| 10 | H | " | 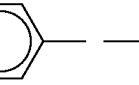 | " | " |
TABLE 4
| Compound No. | R₁ | R₂ | Ar₁ | R₃ | R₄ |
|---|---|---|---|---|---|
| 11 |  | 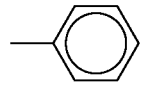 | 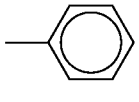 | —CH₃ | 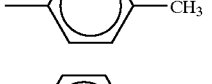 |
| 12 | " | " | " |  | " |
| 13 | " | " | " | 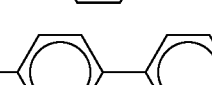 | " |
| 14 | " | " | " | 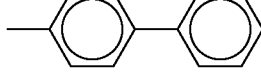 | " |
| 15 | " | " | " |  | " |
| 16 | " | " | " |  | " |

TABLE 4-continued

| Compound No. | R$_1$ | R$_2$ | Ar$_1$ | R$_3$ | R$_4$ |
|---|---|---|---|---|---|
| 17 | " | " | " | —CH$_2$—C$_6$H$_5$ (benzyl) | " |
| 18 | " | " | " | 2-methylphenyl | " |
| 19 | " | " | " | 3-methylphenyl | " |
| 20 | " | " | " | 4-methylphenyl | 4-methylphenyl |

TABLE 5

| Compound No. | R$_1$ | R$_2$ | Ar$_1$ | R$_3$ | R$_4$ |
|---|---|---|---|---|---|
| 21 | phenyl | phenyl | 1,4-phenylene | 4-methoxyphenyl | 4-methoxyphenyl |
| 22 | " | " | " | 1-naphthyl | phenyl |
| 23 | 4-methylphenyl | " | " | phenyl | " |
| 24 | 3-methylphenyl | " | " | " | " |
| 25 | 3-methylphenyl | " | " | " | " |
| 26 | 4-methoxyphenyl | " | " | " | " |
| 27 | 4-chlorophenyl | " | " | " | " |

TABLE 5-continued
| Compound No. | R₁ | R₂ | Ar₁ | R₃ | R₄ |
|---|---|---|---|---|---|
| 28 | " | " | " | 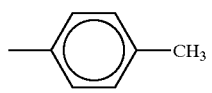 | " |
| 29 | " | " | " | 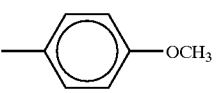 | " |
TABLE 6
| Compound No. | R₁ | R₂ | Ar₁ | R₃ | R₄ |
|---|---|---|---|---|---|
| 30 |  | 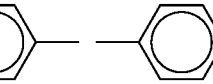 | 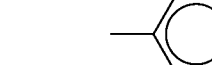 |  | 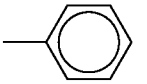 |
| 31 | 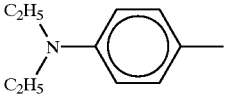 | " | " | " | " |
| 32 | 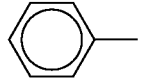 | " | 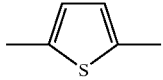 | " | " |
| 33 | " | " | 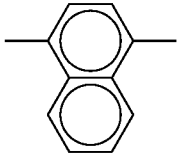 | " | " |
| 34 | " | H |  | 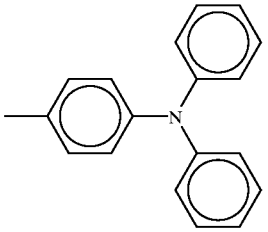 | " |
| 35 | " | 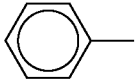 | " | 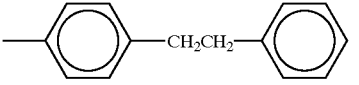 | " |
| 36 | 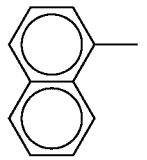 | H | " | 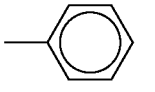 | " |

TABLE 7

| Compound No. | $R_1$ | $R_2$ | $Ar_1$ | $R_3$ | $R_4$ |
|---|---|---|---|---|---|
| 37 | $r_1, r_2$ C= forms | bicyclic (indane/decalin-like) methylene | -C₆H₄- (para-phenylene) | phenyl | phenyl |
| 38 | " | indane methylene | " | " | " |
| 39 | " | fluorene methylene | " | " | " |
| 40 | " | fluorene methylene | " | -C₆H₄-CH₃ (p-tolyl) | -C₆H₄-CH₃ (p-tolyl) |

TABLE 8

| Compound No. | $R_1$ | $R_2$ | $Ar_1$ | $R_3$ | $R_4$ |
|---|---|---|---|---|---|
| 41 | phenyl | phenyl | -C₆H₄- | -C₆H₄-CH₃ (p) | -C₆H₄-C₂H₅ (p) |
| 42 | " | " | " | -C₆H₄-C₆H₄-CH₃ (biphenyl-p-methyl) | -C₆H₄-CH₃ (p) |
| 43 | " | " | " | -C₆H₄-CH₃ (o-tolyl) | -C₆H₄-CH₃ (o-tolyl) |
| 44 | " | " | " | -C₆H₄-C₂H₅ (p) | -C₆H₄-C₂H₅ (p) |
| 45 | " | " | " | -C₆H₄-CH₃ (p) | -C₆H₄-OCH₃ (p) |

TABLE 8-continued
| Compound No. | R₁ | R₂ | Ar₁ | R₃ | R₄ |
|---|---|---|---|---|---|
| 46 | " | " | " | 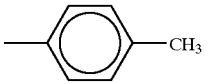 | 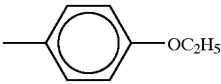 |
| 47 | " | " | " |  |  |
| 48 | " | " | " | 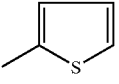 | 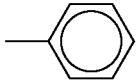 |
| 49 | " | " | " | 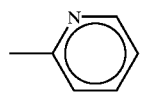 | 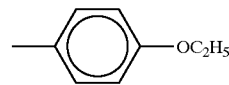 |
| 50 | " | " | " | 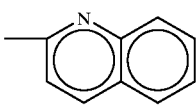 | 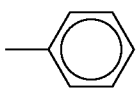 |
TABLE 9
| Compound No. | R₁ | R₂ | Ar₁ | R₃ | R₄ |
|---|---|---|---|---|---|
| 51 | 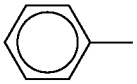 | 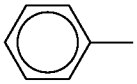 | 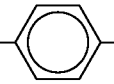 | 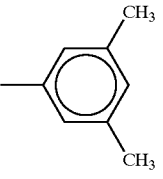 | 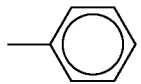 |
| 52 | " | " | " | 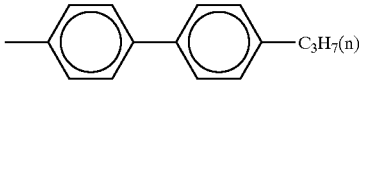 | 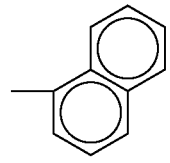 |
| 53 | " | " | " | 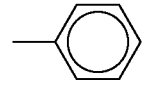 | 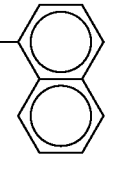 |
| 54 | " | " | " | 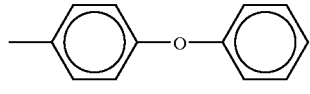 | 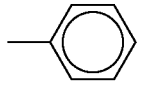 |
| 55 | " | " | " | 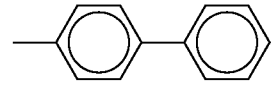 | 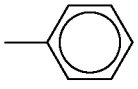 |
| 56 | " | " | " | 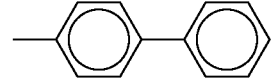 |  |

TABLE 9-continued

| Compound No. | $R_1$ | $R_2$ | $Ar_1$ | $R_3$ | $R_4$ |
|---|---|---|---|---|---|
| 57 | " | " | " | 2-ethylphenyl | naphthyl |
| 58 | " | " | " | 2-biphenylyl | phenyl |
| 59 | " | " | " | 4-ethylphenyl | 4-methoxyphenyl |
| 60 | " | " | " | 3-ethoxyphenyl | 3-ethoxyphenyl |

TABLE 10

| Compound No. | $R_1$ | $R_2$ | $Ar_1$ | $R_3$ | $R_4$ |
|---|---|---|---|---|---|
| 61 | phenyl | phenyl | 1,4-phenylene | 2-fluorenyl | 3-methoxyphenyl |
| 62 | " | " | " | —$CH_3$ | —$CH_3$ |
| 63 | " | " | " | —$C_2H_5$ | —$C_2H_5$ |
| 64 | " | " | " | —$CH_2$—phenyl | —$CH_3$ |
| 65 | " | " | " | —$CH_2$—phenyl | —$CH_2$—phenyl |
| 66 | " | " | " | —$CH_2$—phenyl | 4-methylphenyl |
| 67 | " | " | " | 3,4-dimethylphenyl | phenyl |
| 68 | " | " | " | 4-ethylphenyl | phenyl |

TABLE 10-continued
| Compound No. | R₁ | R₂ | Ar₁ | R₃ | R₄ |
|---|---|---|---|---|---|
| 69 | " | " | " | 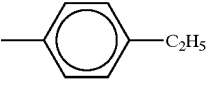—C₂H₅ | 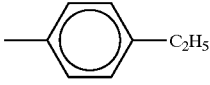—C₂H₅ |
| 70 | " | " | " | 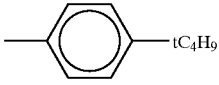—tC₄H₉ | 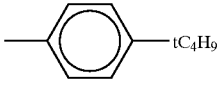—tC₄H₉ |
TABLE 11
| Compound No. | R₁ | R₂ | Ar₁ | R₃ | R₄ |
|---|---|---|---|---|---|
| 71 | 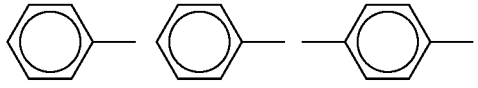 | 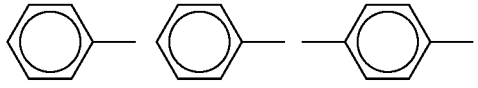 | 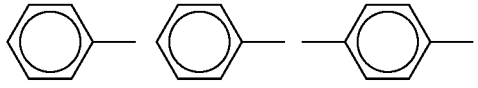 | 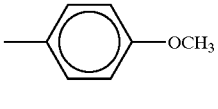—OCH₃ | 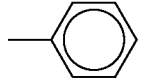 |
| 72 | " | " | " | 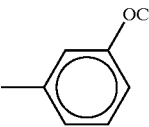 | 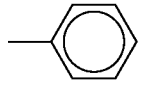 |
| 73 | " | " | " | 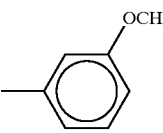 | 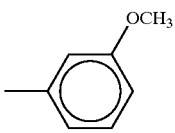 |
| 74 | " | " | " | 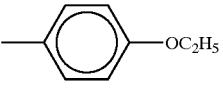—OC₂H₅ | 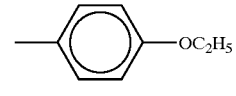—OC₂H₅ |
| 75 | " | " | " | 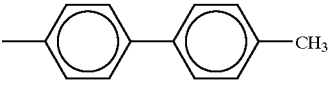—CH₃ | —CH₃ |
| 76 | " | " | " | 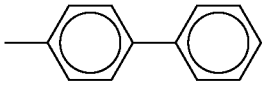 | 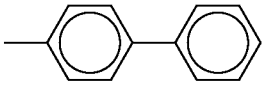 |
| 77 | " | " | " | 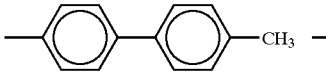—CH₃ | 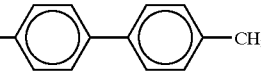—CH₃ |
| 78 | " | " | " | 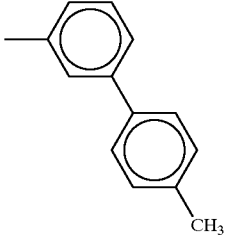 | 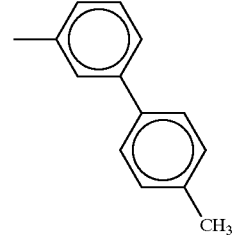 |

TABLE 11-continued
| Compound No. | R₁ | R₂ | Ar₁ | R₃ | R₄ |
|---|---|---|---|---|---|
| 79 | " | " | " | 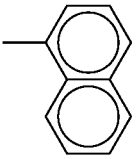 | 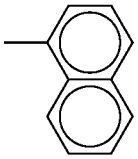 |
| 80 | " | " | " | 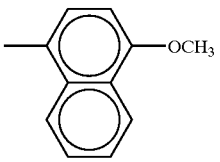 | 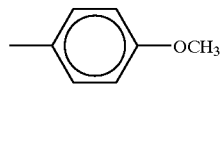 |
TABLE 12
| Compound No. | R₁ | R₂ | Ar₁ |
|---|---|---|---|
| 81 | 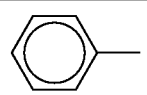 | 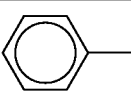 | 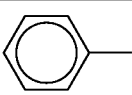 |
| 82 | " | " | " |
| 83 | " | " | " |
| 84 | " | " | " |
| 85 | " | " | " |
| 86 | " | " | " |
| 87 | " | " | " |
| 88 | " | " | " |
| 89 | " | " | " |
| Compound No. | R₃ | R₄ |
|---|---|---|
| 81 | 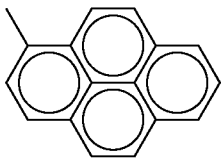 | 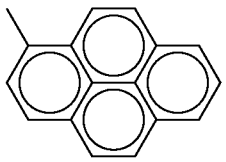 |
| 82 | 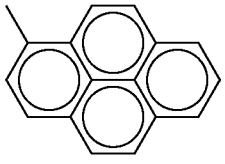 | 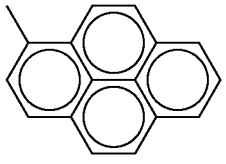 |
| 83 | 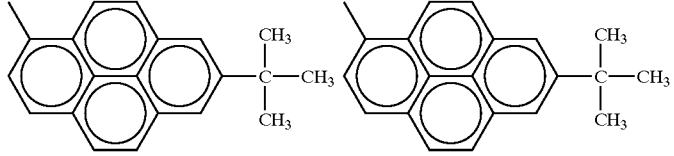 | 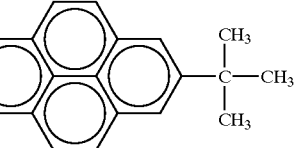 |
| 84 | 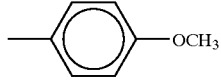 |  |

TABLE 12-continued

| | | |
|---|---|---|
| 85 | 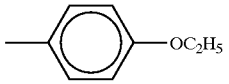 | 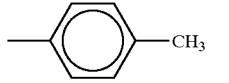 |
| 86 |  | 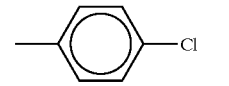 |
| 87 | 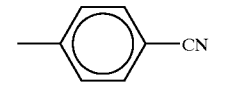 | 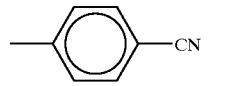 |
| 88 | 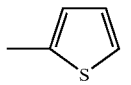 | 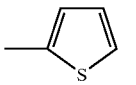 |
| 89 | 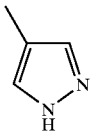 | 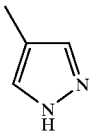 |

As a positive hole transport material, there may be mentioned the following compounds represented by the general formulas (10) to (27).

(1) Compound represented by the following general formula (10) (described in Japanese Laid-Open Patent Applications Nos. 55-154955 and 55-156954):

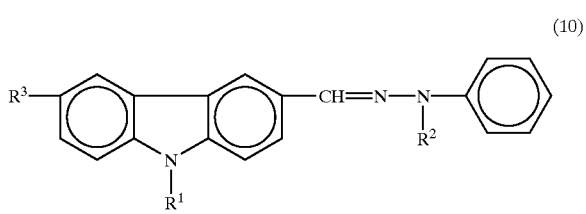

(10)

wherein $R^1$ is methyl group, ethyl group, 2-hydroxyethyl group or 2-chloroethyl group; $R^2$ is methyl group, ethyl group, benzyl group or phenyl group; $R^3$ is a hydrogen atom, a chlorine atom, a bromine atom, an alkyl group having 1 to 4 carbon atoms, an alkoxyl group having 1 to 4 carbon atoms, a dialkylamino group or nitro group.

Examples of the above compound represented by the general formula (10) are 9-ethylcarbazole-3-aldehyde-1-methyl-1-phenylhydrazone, 9-ethylcarbazole-3-aldehyde-1-benzyl-1-phenylhydrazone, and 9-ethylcarbazole-3-aldehyde-1,1-diphenylhydrazone.

(2) Compound represented by the following general formula (11) (described in Japanese Laid-Open Patent Application No. 55-52063):

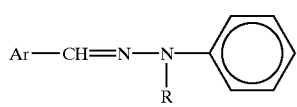

(11)

wherein Ar is a naphthalene ring, anthracene ring, styryl ring, each of which may have a substituent, a pyridine ring, furan ring or thiophene ring; and R is an alkyl group or benzyl group.

Examples of the above compound represented by the general formula (11) are 4-diethylaminostyryl-3-aldehyde-1-methyl-1-phenylhydrazone, and 4-methoxynaphthalene-1-aldehyde-1-benzyl-1-phenyihydrazone.

(3) Compound represented by the following general formula (12) (described in Japanese Laid-Open Patent Application No. 56-81850):

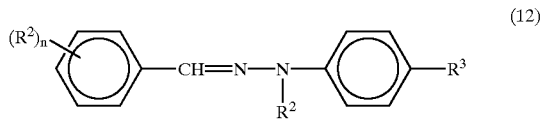

(12)

wherein $R^1$ is an alkyl group, benzyl group, phenyl group or naphthyl group, $R^2$ is a hydrogen atom, an alkyl group having 1 to 3 carbon atoms, an alkoxyl group having 1 to 3 carbon atoms, a dialkylamino group, a diaralkylamino group or a diarylamino group, n is an integer of 1 to 4, with the proviso that when n is 2 or more, $R^2$ may be the same or different; and $R^3$ is a hydrogen atom or methoxy group.

Examples of the above compound represented by the general formula (12) are 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-benzyl-1-(4-methoxy)phenylhydrazone, 4-diphenylaminobenzaldehyde-1-benzyl-1-phenylhydrazone, and 4-dibenzylaminobenzaldehyde-1,1-diphenylhydrazone.

(4) Compound represented by the following general formula (13) (described in Japanese Laid-Open Patent Application No. 51-10983):

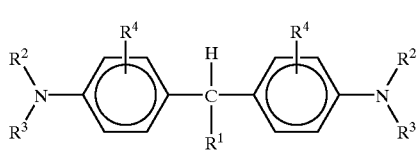

(13)

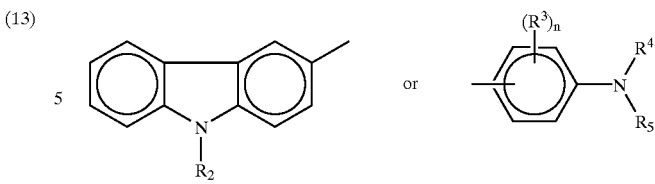

wherein $R^1$ is an alkyl group having 1 to 11 carbon atoms, a substituted or unsubstituted phenyl group, or a heterocyclic group; $R^2$ and $R^3$ are each independently a hydrogen atom, an alkyl group having 1 to 4 carbon atoms, a hydroxyalkyl group, chloroalkyl group, or a substituted or unsubstituted aralkyl group, with the proviso that $R^2$ and $R^3$ may form a nitrogen-containing heterocyclic ring in combination; and $R^4$, which may be the same or different, each is a hydrogen atom, an alkyl group having 1 to 4 carbon atoms, an alkoxyl group or a halogen atom.

Examples of the above compound represented by the following general formula (13) are 1,1-bis(4-dibenzylaminophenyl)propane, tris(4-diethyl-aminophenyl)methane, 1,1-bis(4-dibenzylaminophenyl)propane, and 2,2'-dimethyl-4,4'bis(diethylamino)triphenylmethane.

(5) Compound represented by the following general formula (14) (described in Japanese Laid-Open Patent Application No. 51-94829):

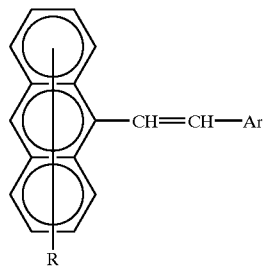

(14)

wherein R is a hydrogen atom or a halogen atom and Ar is a substituted or unsubstituted phenyl group, naphthyl group, anthryl group or carbazolyl group.

Examples of the above compound represented by the following general formula (14) are 9-(4-diethylaminostyryl)anthracene and 9-bromo-10-(4-diethylaminostyryl)anthracene.

(6) Compound represented by the following general formula (15) (described in Japanese Laid-Open Patent Application No. 52-128373):

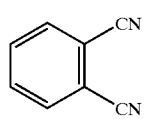

(7)

wherein $R^1$ is a hydrogen atom, a halogen atom, a cyano group, an alkoxyl group having 1 to 4 carbon atoms, or an alkyl group having 1 to 4 carbon atoms; and Ar is where $R^1$ is an alkyl group having 1 to 4 carbon atoms; $R^3$ is a hydrogen atom, a halogen atom, an alkyl group having 1 to 4 carbon atoms, an alkoxyl group having 1 to 4 carbon atoms, or a dialkylamino group; n is an integer of 1 or 2 with the proviso that when n is 2, $R^3$ may be the same or different; and $R^4$ and $R^5$ are each a hydrogen atom, a substituted or unsubstituted alkyl group having 1 to 4 carbon atoms, or a substituted or unsubstituted benzyl group.

Examples of the above compound represented by the general formula (15) are 9-(4-dimethylaminobenzylidene)-fluorene, and 3-(9-fluorenylidene)-9-ethylcarbazole.

(7) Compound (16) (described in Japanese Laid-Open Patent Application No. 56-29245):

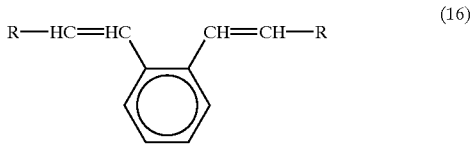

(16)

wherein R is a carbazolyl group, pyridine group, thienyl group, indolyl group, furyl group, a substituted or unsubstituted phenyl group, a substituted or unsubstituted styryl group, a substituted or unsubstituted naphthyl group, or a substituted or unsubstituted anthryl group, with the substituent being selected from the group consisting of a dialkylamino group, an alkyl group, an alkoxyl group, a carboxyl group and an ester group thereof, a halogen atom, a cyano group, an aralkylamino group, an N-alkyl-N-aralkylamino group, an amino group, a nitro group and an acetylamino group.

Examples of the above compound represented by the general formula (16) are 1,2-bis(4-diethylaminostyryl)benzene, and 1,2-bis(2,4-dimethoxystyryl)benzene.

(8) Compound represented by the following general formula (17) (described in Japanese Laid-Open Patent ApplILcatlon No. 58-58552):

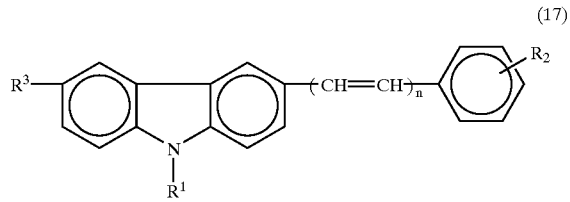

(17)

wherein $R^1$ is a lower alkyl group, a substituted or unsubstituted phenyl group, or benzyl group; $R^2$ and $R^3$ are each a hydrogen atom, a lower alkyl group, a lower alkoxyl group, a halogen atom, a nitro group, or an amino group which may have as a substituent a lower alkyl group or benzyl group; and n is an integer of 1 or 2.

Examples of the above compound represented by the general formula (17) are 3-styryl-9-ethylcarbazole, and 3-(4-methoxystyryl)-9-ethyl carbazole.

(9) Compound represented by the following general formula (18)(described in Japanese Laid-Open Patent Application No. 57 73075):

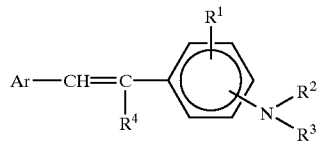
(18)

wherein $R^1$ is a hydrogen atom, an alkyl group, an alkoxyl group or a halogen atom; $R^2$ and $R^3$ are each an alkyl group, a substituted or unsubstituted aralkyl group, or a substituted or unsubstituted aryl group; $R^4$ is a hydrogen atom or a substituted or unsubstituted phenyl group; and Ar is a substituted or unsubstituted phenyl group or a substituted or unsubstituted naphthyl group.

Examples of the above compound represented by the general formula (18) are 4-diphenylaminostilbene, 4-dibenzylaminostilbene, 4-ditolylaminostilbene, 1-(4-diphenylaminostyryl)-naphthalene, and 1-(4-diethylaminostyryl)naphthalene.

Compound represented by the following general formula (19) (described in Japanese Laid-Open Patent Application No. 58-198043):

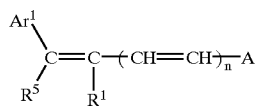
(19)

wherein n is an integer of 0 or 1; $R^1$ is a hydrogen atom, an alkyl group or a substituted or unsubstituted phenyl group; $Ar^1$ is a substituted or unsubstituted aryl group; $R^5$ is a substituted or unsubstituted alkyl group or a substituted or unsubstituted aryl group; and A is 9-anthryl group, a substituted or unsubstituted carbazolyl group or a group of the formula:

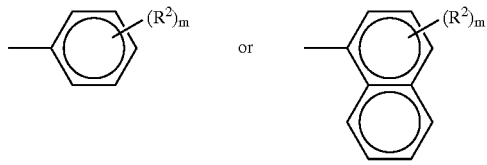

where $R^2$ is a hydrogen atom, an alkyl group, an alkoxyl group, a halogen atom or —$NR^3R^4$ where $R^3$ and $R^4$ are each an alkyl group, a substituted or unsubstituted aralkyl group or a substituted or unsubstituted aryl group, with the proviso that $R^3$ and $R^4$ may be the same or different, or may form a ring in combination, and m is an integer of 0 to 3, provided that when m is 2 or more R may be the same or different and when n is 0, A and R may form a ring in combination.

Examples of the above compound represented by the general formula (19) are 4'-diphenylamino-α-phenylstilbene and 4'-bis(methyl-phenyl)amino-α-phenylstilbene.

(11) Compound represented by the following general formula (20) (described in Japanese Laid-Open Patent Application No. 49-105537):

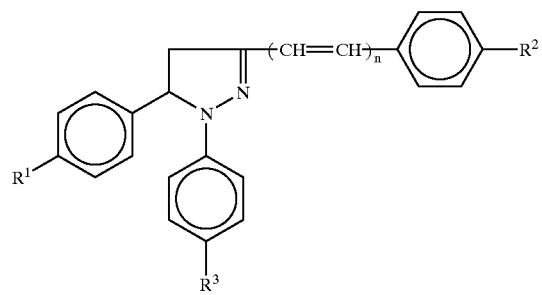
(20)

wherein $R^1$, $R^2$ and $R^3$ are each a hydrogen atom, a lower alkyl group, a lower alkoxyl group, a dialkylamino group or a halogen atom; and n is an integer of 0 or 1.

Examples of the above compound represented by the general formula (20) include 1-phenyl-3-(4-diethylarninostyryl)-5-(4-diethylaminophenyl)pyrazoline and 1-phenyl-3-(4-dimethylaminostyryl)-5-(4-dimethylaminophenyl)pyrazoline.

(12) Compound represented by the following general formula (21) (described in Japanese Laid-Open Patent Appllcation No. 52-139066):

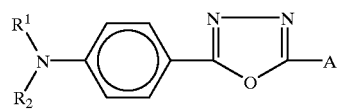
(21)

wherein $R^1$ and $R^2$ are each a substituted or unsubstituted alkyl group or a substltuted or unsubstliluted aryl group; and A is a substituted amino group, a substituted or unsubstituted aryl group or an allyl group.

Examples of the above compound of formula (21) are 2,5-bis(4-diethylaminophenyl)-1,3,4-oxadlazole, 2-N,N-diphenylamino-5-(4-diethylaminophenyl)-1,3,4-oxadiazole, and 2-(4-dimethylaminophenyl)-5-(4-diethylaminophenyl)-1,3,4 oxadlazole.

(13) Compound represented by the following general formula (22) (described in Japanese Laid-Open Patent Application No. 52-139065):

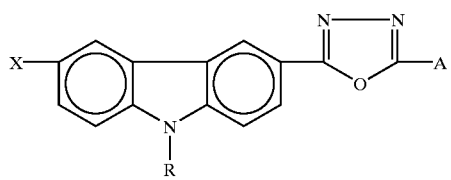
(22)

wherein X is a hydrogen atom, a lower alkyl group or a halogen atom; R is a substituted or unsubstituted alkyl group or a substituted or unsubstituted aryl group; and A is a substituted amino group or a substituted or unsubstituted aryl group.

Examples of the above compound represented by the following general formula (22) are 2-N,N-diphenylamino-5-(N-ethylcarbazole-3-yl)-1,3,4-oxadiazole and 2-(4-diethylaminophenyl)-5-(N-ethylcarbazole-3-yl)-1,3,4-oxadiazole.

(14) Compound represented by the following general formula (23) (described in Japanese Laid-Open Patent Application No. 58-32372):

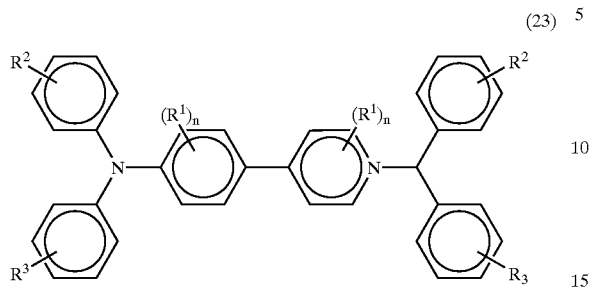

(23)

wherein $R^1$ is a lower alkyl group, a lower alkoxyl group or a halogen atom; n is an integer of 0 to 4; and $R^2$ and $R^3$ may be the same or different and are each a hydrogen atom, a lower alkyl group, a lower alkoxyl group or a halogen atom.

Examples of the benzidine compound represented by the general formula (23) are N,N'-diphenyl-N,N'-bis(3-methylphenyl)-[1,1'-biphenyl]-4,4'-diamine, and 3,3'-dimethyl-N,N,N',N'-tetrakis(4-methylphenyl)-[1,1'-biphenyl]-4,4'-diamine.

(15) Compound represented by the following general formula (24) (described in Japanese Laid-Open Patent Application No. 2-178669):

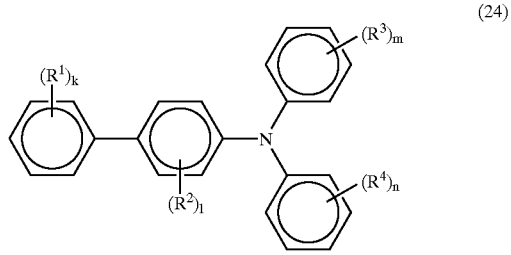

(24)

wherein $R^1$, $R^3$ and $R^4$ are each a hydrogen atom, amino group an alkoxyl group, a thioalkoxyl group, an aryloxy group, ma ethylenedioxy group, a substituted or unsubstituted alkyl group, a halogen atom or a substituted or unsubstituted aryl group; $R^2$ is a hydrogen atom, an alkoxyl group, a substituted or unsubstituted alkyl group or a halogen atom with the proviso that $R^1$, $R^2$, $R^3$ and $R^4$ are not hydrogen atoms at the same time; and k, l, m and n are each an integer of 1 to 4 with the proviso that when each is an integer of 2, 3 or 4, $R^1$, $R^2$, $R^3$ and $R^4$ may be independently the same or different.

Examples of the biphenylamine compound represented by the general formula (24) are 4'-methoxy-N,N-diphenyl-[1,1'-biphenyl]-4-amine, 4'-methyl-N,N'-bis(4-methylphenyl)-[1,1'-biphenyl]-4-amine, and 4'-methoxy-N,N'-bis(4-methylphenyl-[1,1'-biphenyl]-4-amine.

(16) Compound (25) (described in Japanese Laid-Open Patent Application No. 3-285960):

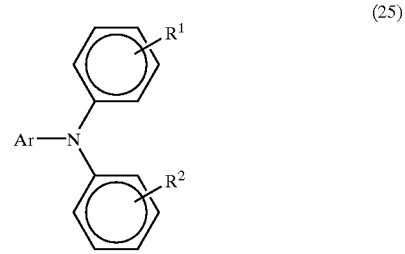

(25)

wherein Ar is a condensed polycyclic hydrocarbon group having 18 or less carbon atoms; and $R^1$ and $R^2$ may be the same or different and are each a hydrogen atom, a halogen atom, a substituted or unsubstituted alkyl group, an alkoxyl group or a substituted or unsubstituted phenyl group.

Examples of the triarylamine compound represented by the general formula (25) are 1-diphenylaminopyrene and 1-di(p-tolylamino)pyrene.

(17) Compound represented by the following general formula (26) (described in Japanese Laid-Open Patent Application No. 62-98394):

$$A—CH=CH—Ar—CH=CH—A \qquad (26)$$

wherein Ar is a substituted or unsubstituted aromatic hydrocarbon group; and A is

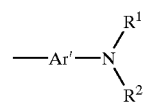

where Ar' is a substituted or unsubstituted aromatic hydrocarbon group; and $R^1$ and $R^2$ are each a substituted or unsubstituted alkyl group or a substituted or unsubstituted aryl group.

Examples of the diolefinic aromatic compound represented by the general formula (26) are 1,4-bis(4-diphenylaminostyryl)benzene and 1,4-bis[4-di(p-tolyl)aminostyryl]benzene.

(18) Compound represented by the following general formula (27) (described in Japanese Laid-Open Patent Application No. 4-230764):

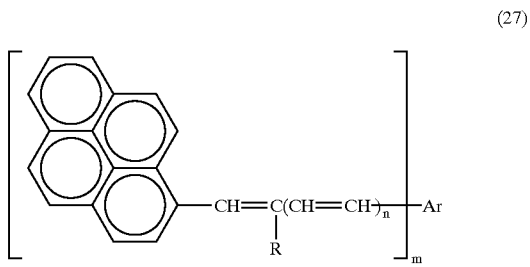

(27)

wherein Ar is an aromatic hydrocarbon group; R is a hydrogen atom, a substituted or unsubstituted alkyl group or a substituted or unsubstituted aryl group; and n is an integer of 0 or 1 and m is an integer of 1 or 2, provided that when n=0 and m=1, Ar and R may form a ring in combination.

Examples of the styrylpyrene compound represented by formula (27) are 1-(4-diphenylaminostyryl)pyrene, and 1-[4-di(p-tolyl)aminostyryl]pyrene.

Electron transport materials may be, for example, chloroanil, bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitroindeno-4H-indeno[1,2-b]thiophen-4-one and 1,3,7-trinitrodibenzothiophene-5,5-dioxide.

In particular, 2,3-diphenylindene compound of the following formula (5).

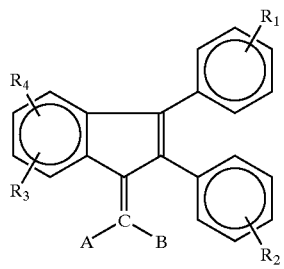

(5)

wherein $R_1$–$R_4$ stand, independently from each other, for a hydrogen atom, a halogen atom, a substituted or unsubstituted alkyl group, a cyano group or a nitro group, and A and B stand, independently from each other, for a hydrogen atom, a halogen atom, a substituted or unsubstituted aryl group, a cyano group, an alkoxycarbonyl group or an aryloxycarbonyl group, is preferably employed because of its excellent electron transporting performance. Of the compounds of the formula (4), 2,3-diphenyl-1-indenylidene) marononitrile of the following formula (28) may be particularly suitably used:

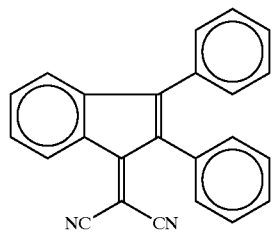

(28)

Further, the compounds of the following formulas (29) and (30) may also be preferably used as the electron transport material for reasons of excellent electron transporting performance:

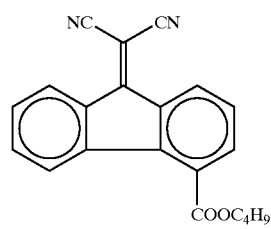

(29)

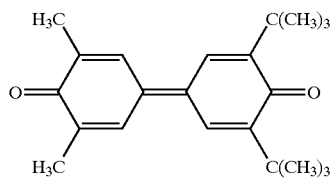

(30)

The above-mentioned charge transport materials may be used alone or in combination of two or more.

The electrophotographic photoconductor of the present invention may be used for an electrophotographic machine comprising charging means, exposing means, developing means, transfer means, cleaning means, charge removing means and an electrophotographic photoconductor and for a process cartridge for an electrophotographic machine comprising charging means and an electrophotographic photoconductor.

Further, the reaction product of the present invention is useful as the photoconductive material for use in the electrophotographic photoconductor, and in addition, as an electronic device for utilization in the field of electronics such as solar batteries and optical disks.

The present invention will be described with reference to examples but is not limited thereby. Parts are by weight.

EXAMPLE 1

(Preparation of Reaction Product No. 1-A)

Figure 33:
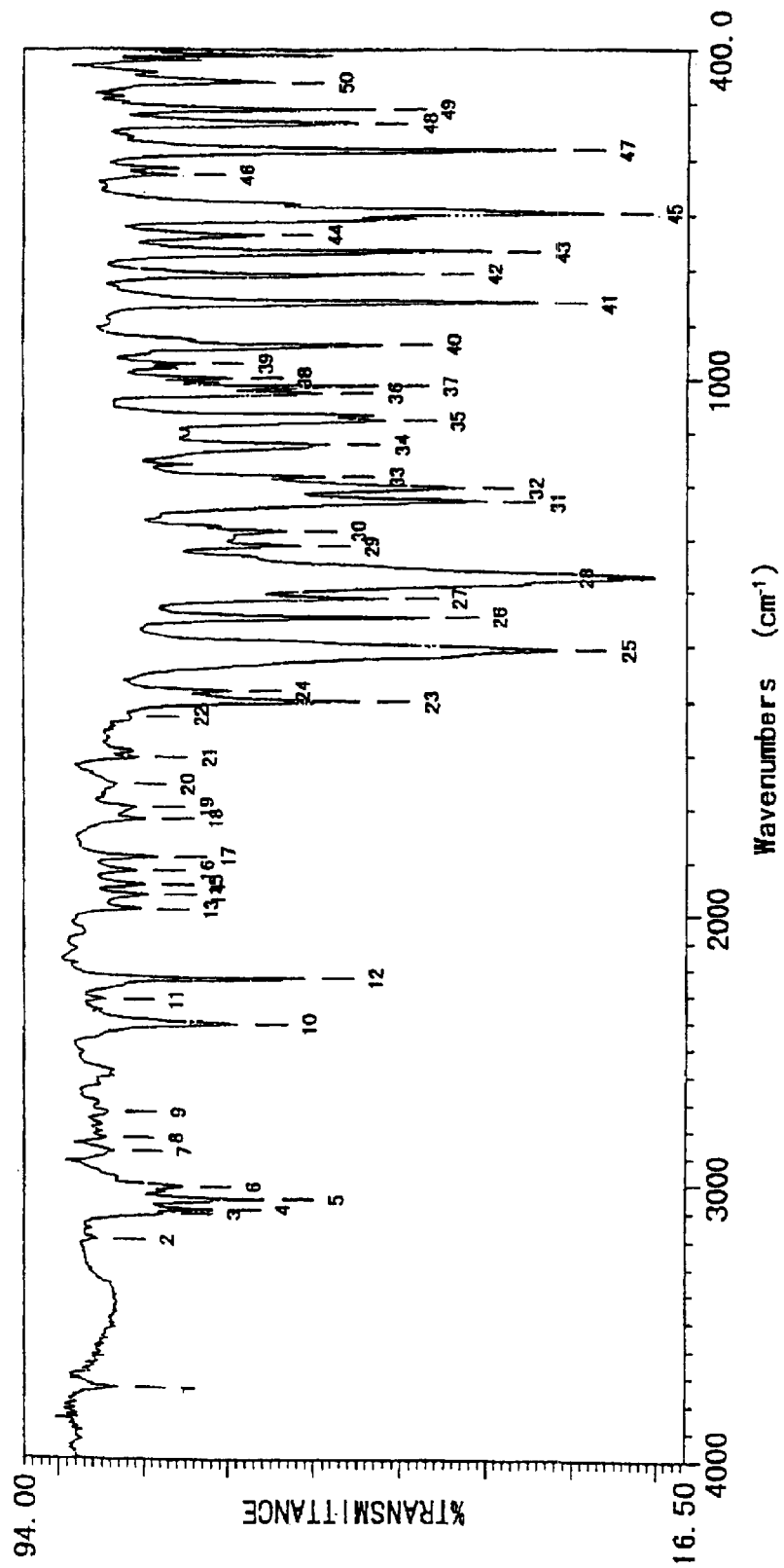
FIG. 33 is an infrared absorption spectrum.

0.1 Mol of 1,4-bisbenzyl, 0.2 mol of diaminomaleonitrile and acetaic acid were stirred under reflux for 6 hours. The mixture was then allowed to be cooled to room temperature, thereby precipitating crystals. The crystals were collected by filtration and isolated by column chromatography using chloroform as a developing solvent to obtain a crude product. This was recrystallized from toluene to obtain a nitrile compound represented by the formula (6) shown below with a yield of 80%. The nitrile compound (6) has a melting point of 270–274° C. An infrared absorption spectrum of the nitrile compound (6) is shown in FIG. 33. The elementary analysis of the nitrile compound (6) gave as follows:

|  | C | H | N |
|---|---|---|---|
| Calculated | 74.32 | 2.74 | 23.21 |
| Found | 74.06 | 2.90 | 23.03 |

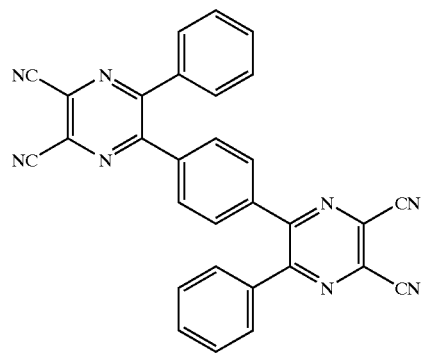

(6)

0.2 Mole of the nitrile derivative A of the formula (6), 0.2 mol of phthalonitrile, 0.1 mol of cuprous chloride and 200 ml of α-chloronaphthalene were mixed with stirring. The mixture was then gradually heated and maintained at 170–180° C. with stirring under a nitrogen gas stream for 5 hours. After completion of the reaction, the reaction mixture was allowed to be cooled to 130° C. and immediately filtered. The solid phase was then washed well with α-chloronaphthalene and then several times with methanol, toluene and water and dried to obtain a reaction product (Exemplified Compound No. 1-A) with a yield of 76%.

EXAMPLE 2

(Preparation of Reaction Product No. 1-B)

0.5 Mole of the nitrile compound (A) represented by the formula (6) obtained in Example 1, 0.3 mol of phthalonitrile, 0.11 mol of Ti(OBu)$_4$ and 200 ml of octanol were mixed with stirring. The mixture was gradually heated to 160° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain a reaction product (Compound No. 1-B) with a yield of 75%.

Figure 26:
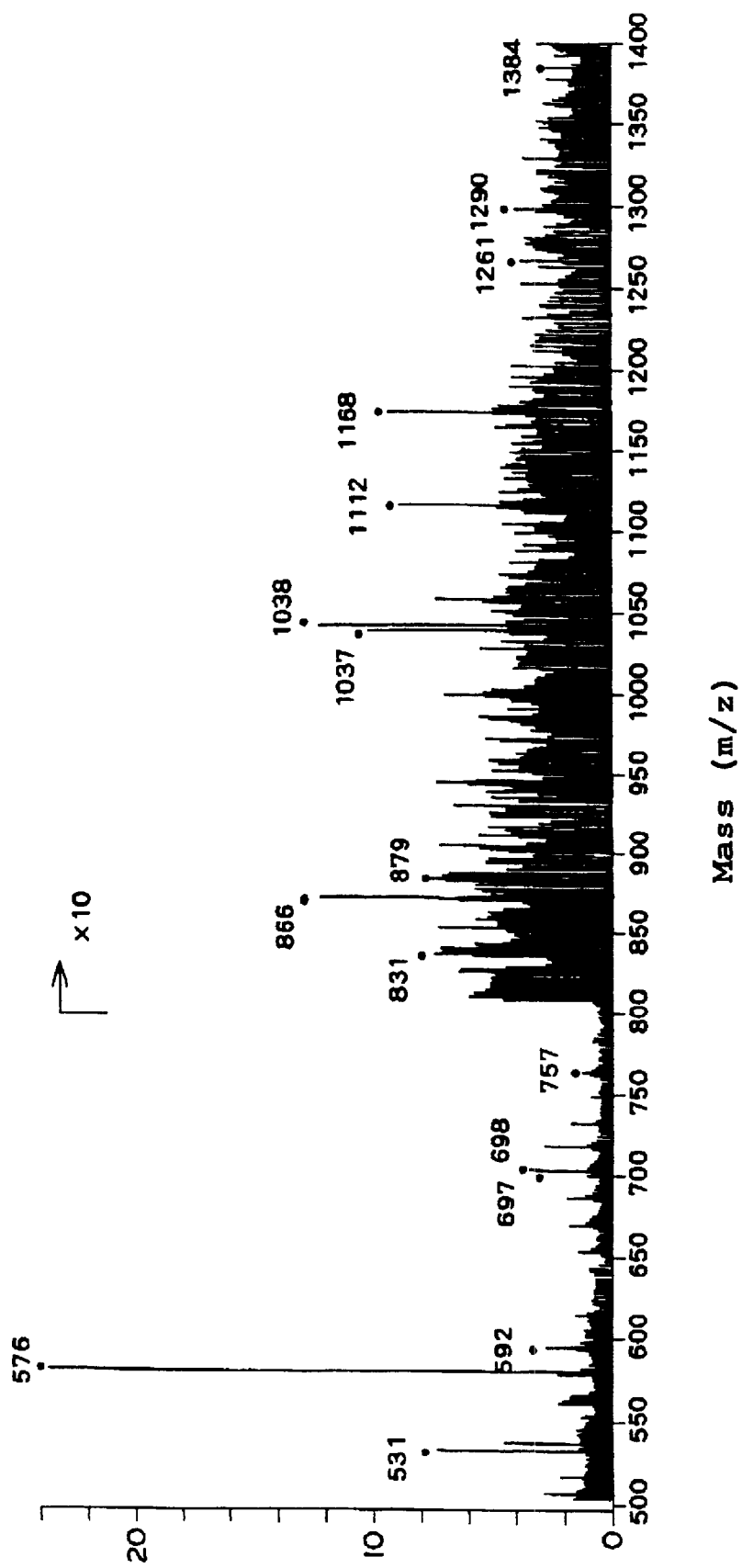
FIG. 26 is a mass spectrum.

The thus obtained Compound No. 1-B was analyzed by mass spectrometer under the following conditions:

LC/MS Device:
  Maker: JEOL
  Name of Device: Mass Analyzer
  Number of Device: MS700
  Conditions of Measurement:
    Ionization: ESI method; +ion detection
    Sample flow rate: 25 μL/min
    Sample injection mode: infusion
    Ring voltage: 80V
    Skimmer voltage: 0V
  Preparation of Sample: Sample was dissolved in formic acid and the solution was diluted with 50% aqueous formic acid to a concentration of 50 ppm The results of the mass spectrometry of Compound No. 1-B are shown in FIG. 26. Peaks corresponding to molecular weight of the compound represented by the above formula (8) (molecular weight: 1383) and the compound represented by the above formula (9) (molecular weight: 576) were observed, suggesting the presence of these compounds.

Figure 27:
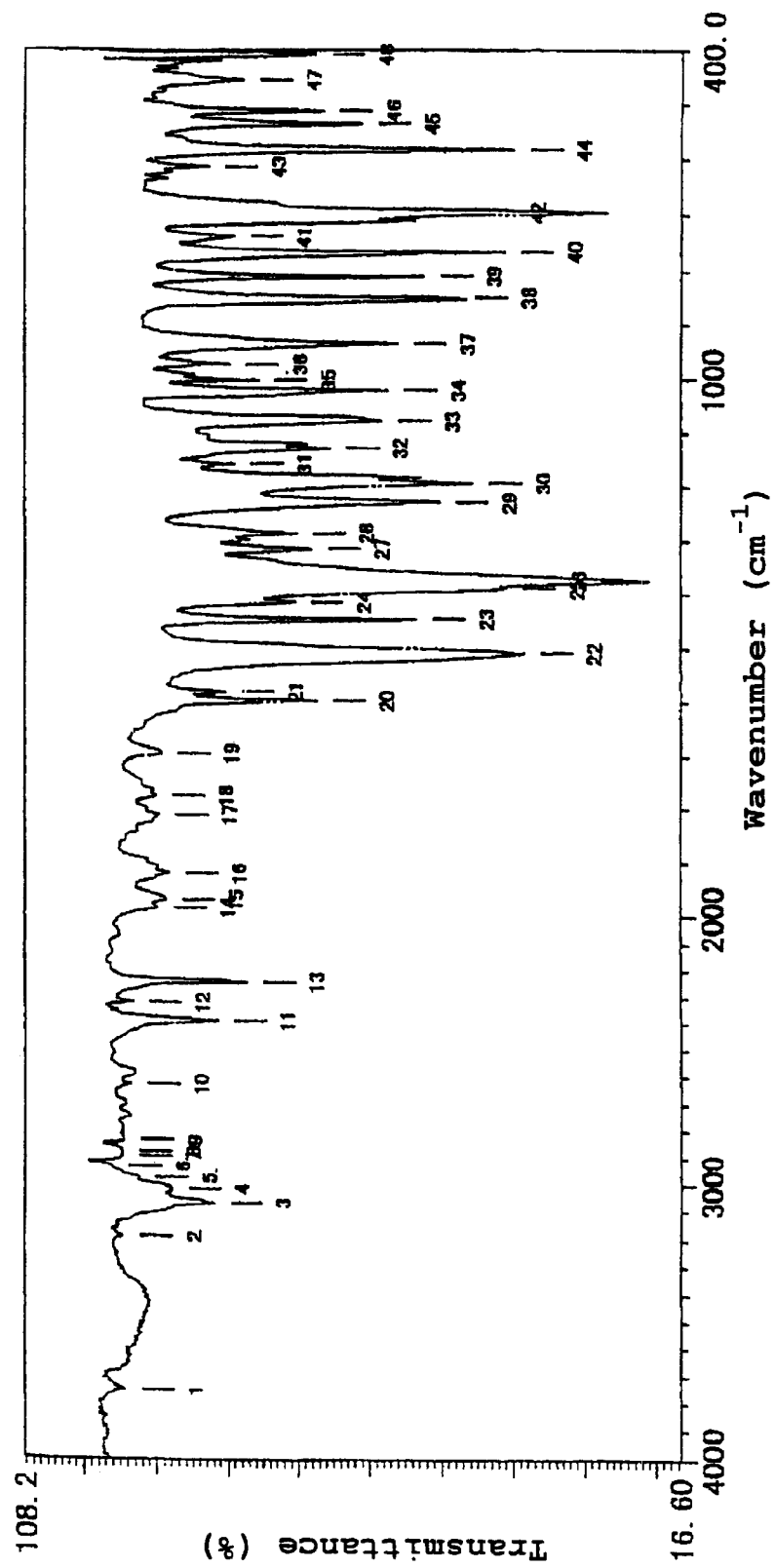
FIG. 27 is an infrared absorption spectrum.
Figure 28:
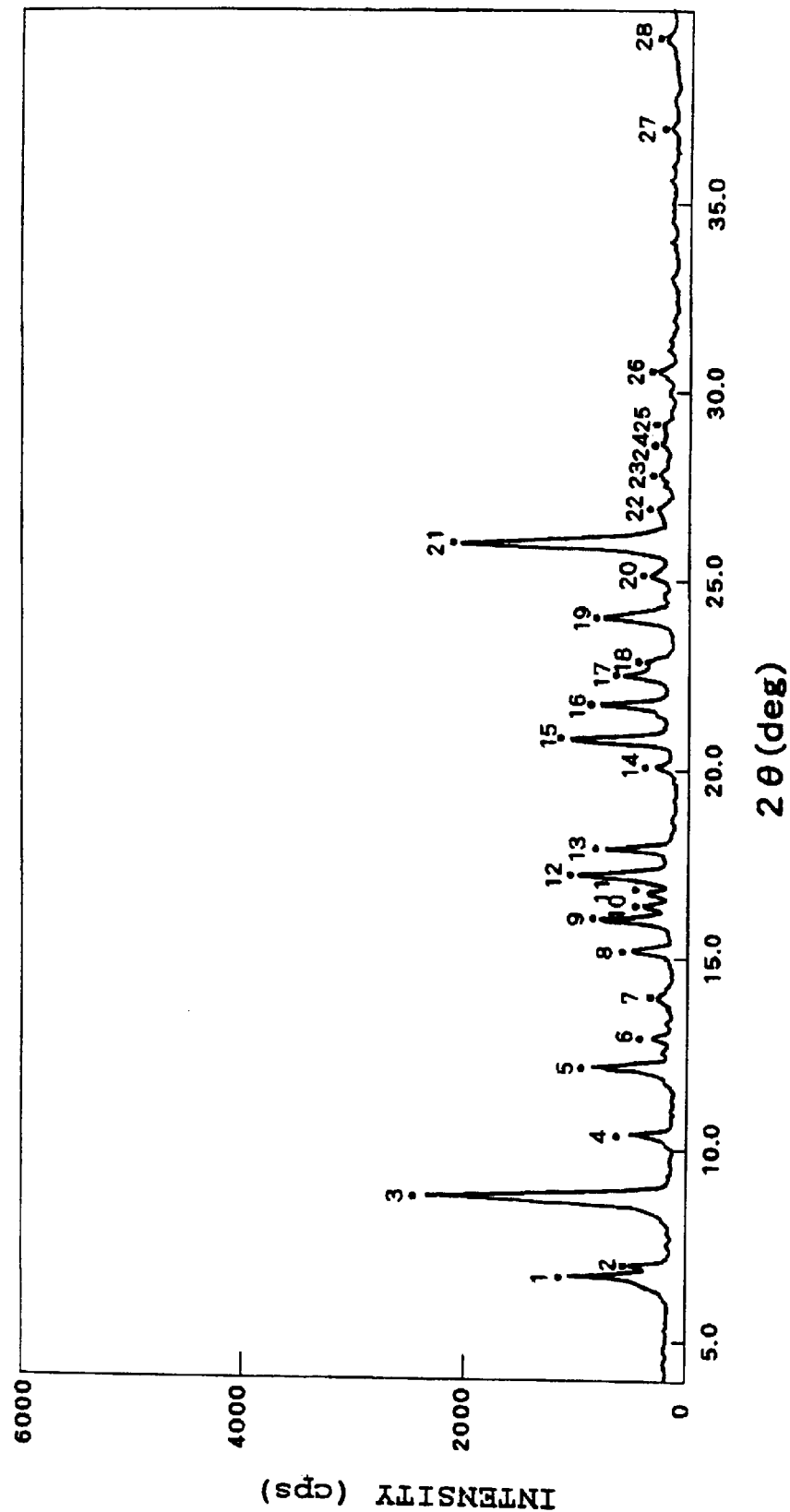
FIG. 28 is an X-ray diffraction spectrum of a reaction product obtained in Example 34.

FIG. 27 is an infrared absorption spectrum of the reaction product. The fluorescent X-ray spectroscopy revealed the presence of Ti in the reaction product.

For the purpose of investigating reproducibility of the reaction product provided by the present invention, manufacture of the reaction product was repeated 10 times in the same manner as described in Example 2. It was found that the products obtained showed the same MS and IR spectra as shown in FIGS. 26 and 27, indicating that the reaction product of the present invention was able to be produced with high reproducibility.

EXAMPLE 3

0.0016 Mole of the nitrile compound A described in Example 1, 0.32 mol of phthalonitrile, 0.09 mol of Ti(OBu)$_4$, 0.16 mole of urea and 200 ml of octanol were mixed with stirring. The mixture was gradually heated to 150° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain a reaction product (Compound No. 1-C) with a yield of 75%.

This product (20 g) was then subjected to an acid treatment using an acid pasting method. Thus, the product was dissolved little by little with stirring in 200 g of concentrated sulfuric acid while being cooled in an ice bath. The mixture was then reacted for 1 hour and subsequently poured into 2000 ml of ice water to form crystals. The crystals were separated by filtration and washed with distilled water until no acid was detected in the washed water. After drying, 18 g of a reaction product was obtained.

EXAMPLE 4

A nitrile derivative (B) represented by the formula (31) was prepared according to the following reaction scheme (DAMN means diaminomaleonitrile):

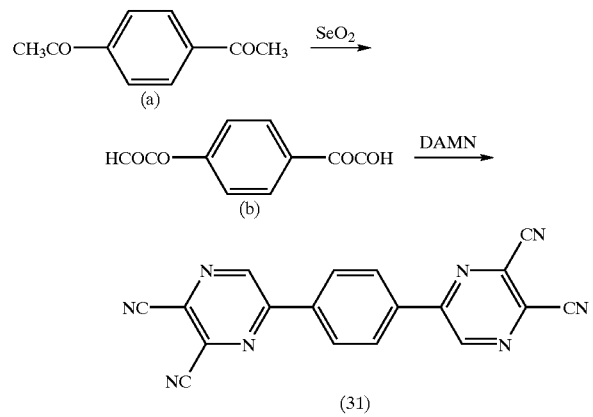

In a reactor, 0.15 mol of SeO$_2$, 120 ml of dioxane and 5 ml of water were charged and heated at 50° C. for 1 hour with stirring, to which a solution of 0.05 ml of (a) dissolved in 20 ml of dioxane was added dropwise. The mixture was then reacted for 8 hours under reflux. Thereafter, the reaction mixture, while hot, was filtered to remove solids. The solvent in the filtrate was removed by distillation to leave the above compound (b).

Figure 34:
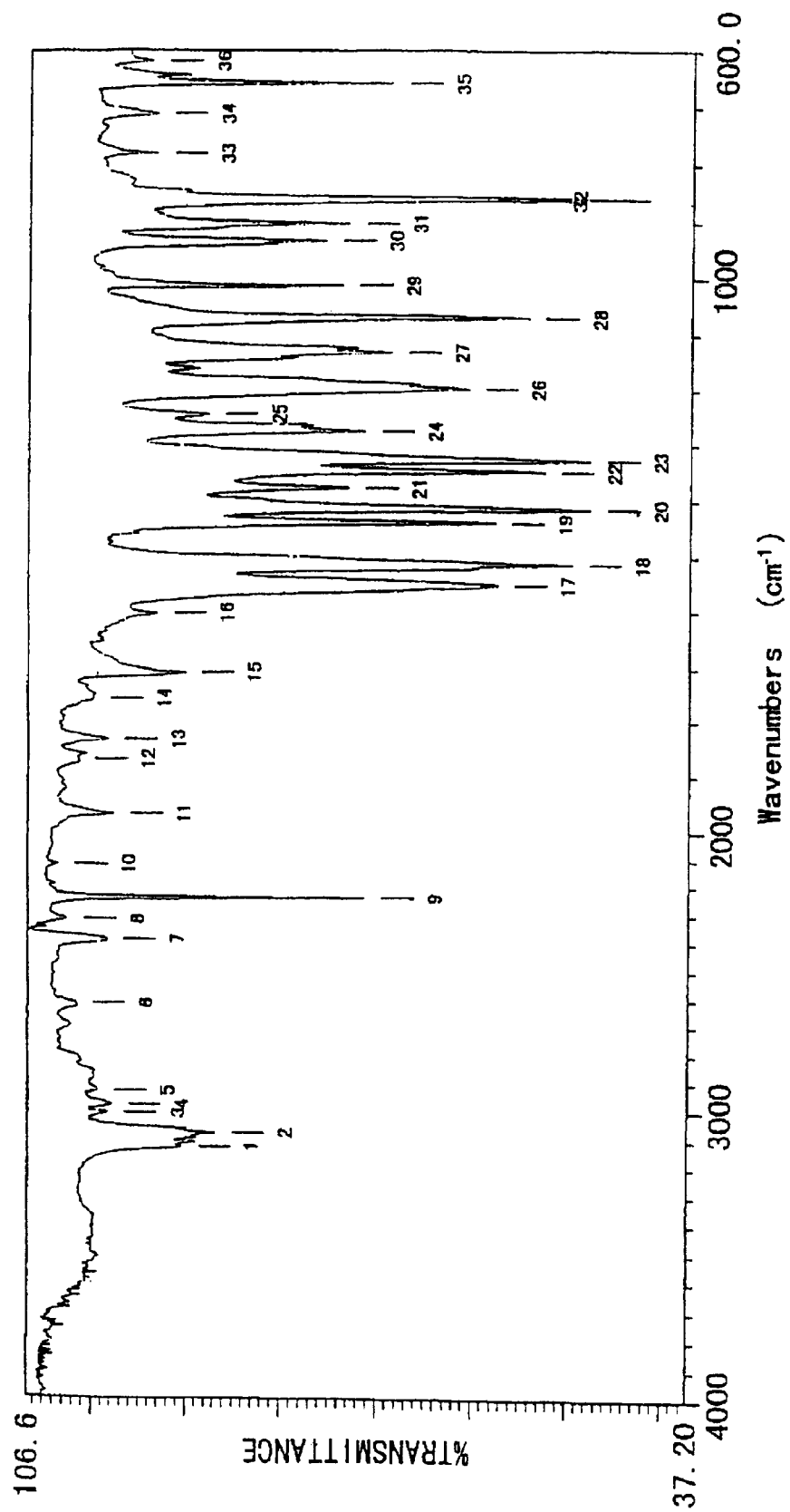
FIG. 34 is an infrared absorption spectrum.

The compound (b) was mixed with 0.1 mol of diaminomaleonitrile, 0.01 mol of p-toluenesulfonic acid and 200 ml of dioxane. The mixture was refluxed for 2 hours and then allowed to be cooled to room temperature, followed by removal of the solvent by distillation. The residue was mixed with 200 ml of methanol to precipitate crystals. The crystals were collected by filtration, washed several times with methanol and dried. The crystals were then isolated by column chromatography using dichloromethane as a developing solvent to obtain a crude product. This was recrystallized from dioxane to the obtain nitrile derivative (B) of the formula (31) with a yield of 60%. An infrared absorption spectrum of the nitrile derivative (B) is shown in FIG. 34. The results of the elementary analysis are shown in Table 14.

TABLE 14

(31)

[Structure of compound (31): pyrazine-phenyl-pyrazine with CN groups]

| | C | H | N |
|---|---|---|---|
| Calculated | 64.67 | 1.81 | 33.52 |
| Found | 64.50 | 1.92 | 33.34 |

0.0016 Mole of the nitrile compound (31), 0.32 mol of phthalonitrile, 0.09 mol of Ti(OBu)$_4$, 0.16 mole of urea and 200 ml of octanol were mixed with stirring. The mixture was gradually heated to 150° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain a reaction product with a yield of 70%.

Figure 29:
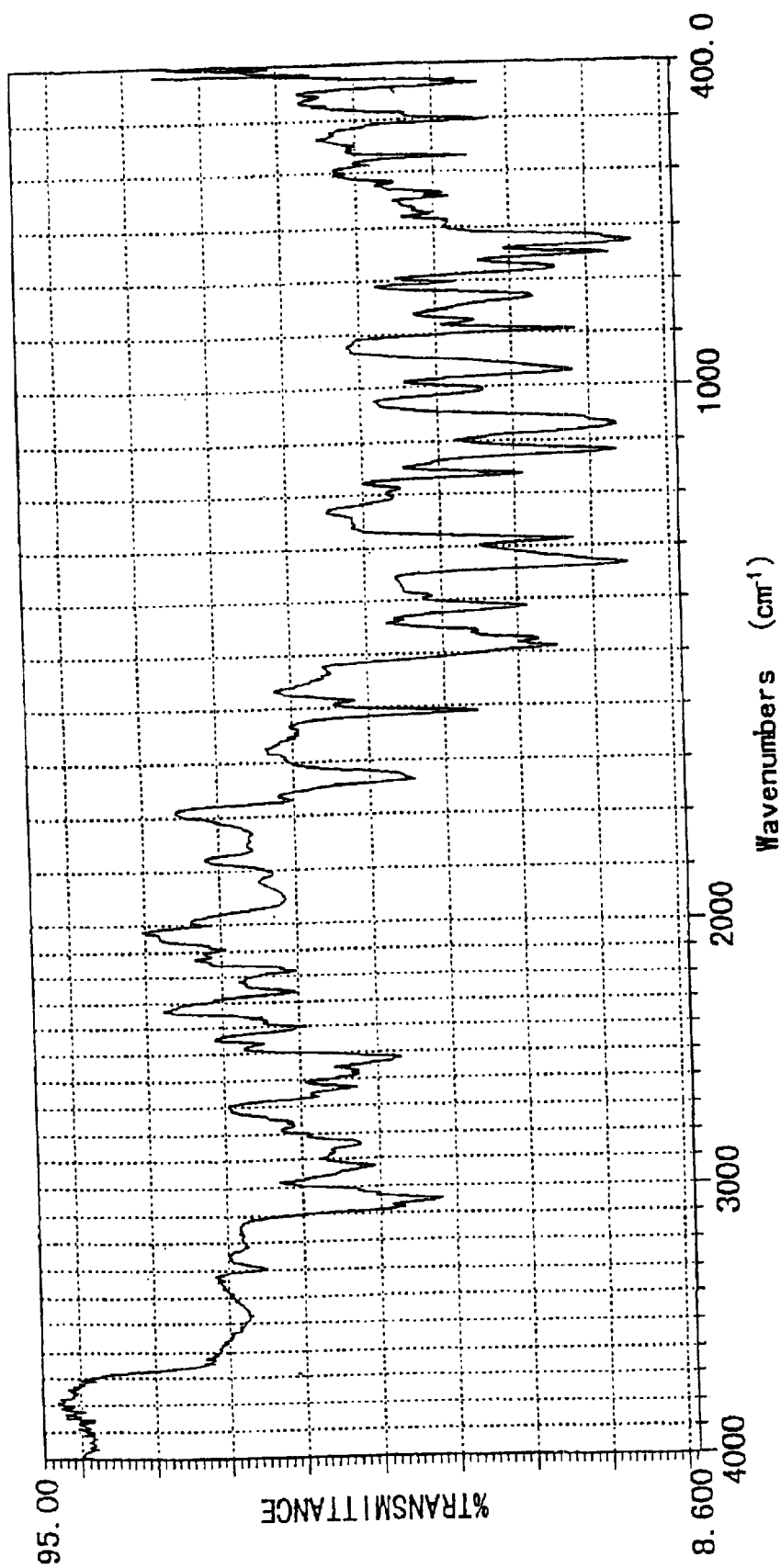
FIG. 29 is an infrared absorption spectrum.

This product (20 g) was then subjected to an acid treatment using an acid pasting method. Thus, the product was dissolved little by little with stirring in 200 g of concentrated sulfuric acid while being cooled in an ice bath. The mixture was then reacted for 1 hour and subsequently poured into 2000 ml of ice water to form crystals. The crystals were separated by filtration and washed with distilled water until no acid was detected in the washed water. After drying, 18 g of a reaction product was obtained. An infrared absorption spectrum of the reaction product is shown in FIG. 29.

EXAMPLE 5

A nitrile derivative (C) of the formula (32) was prepared according to the following reaction scheme (DAMN means diaminomaleonitrile):

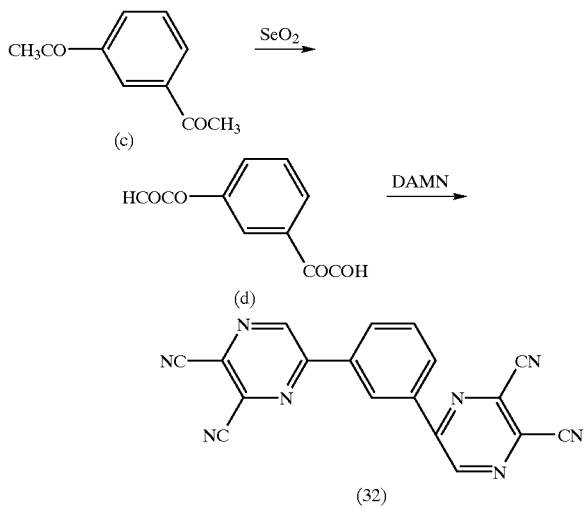

In a reactor, 0.12 mol of SeO$_2$, 120 ml of dioxane and 4 ml of water were charged and heated at 50° C. for 1 hour with stirring, to which a solution of 0.05 ml of the compound (c) dissolved in 20 ml of dioxane was added dropwise. The mixture was then reacted for 8 hours under reflux. Thereafter, the reaction mixture, while hot, was filtered to remove solids. The solvent in the filtrate was removed by distillation to leave the compound (d).

Figure 35:
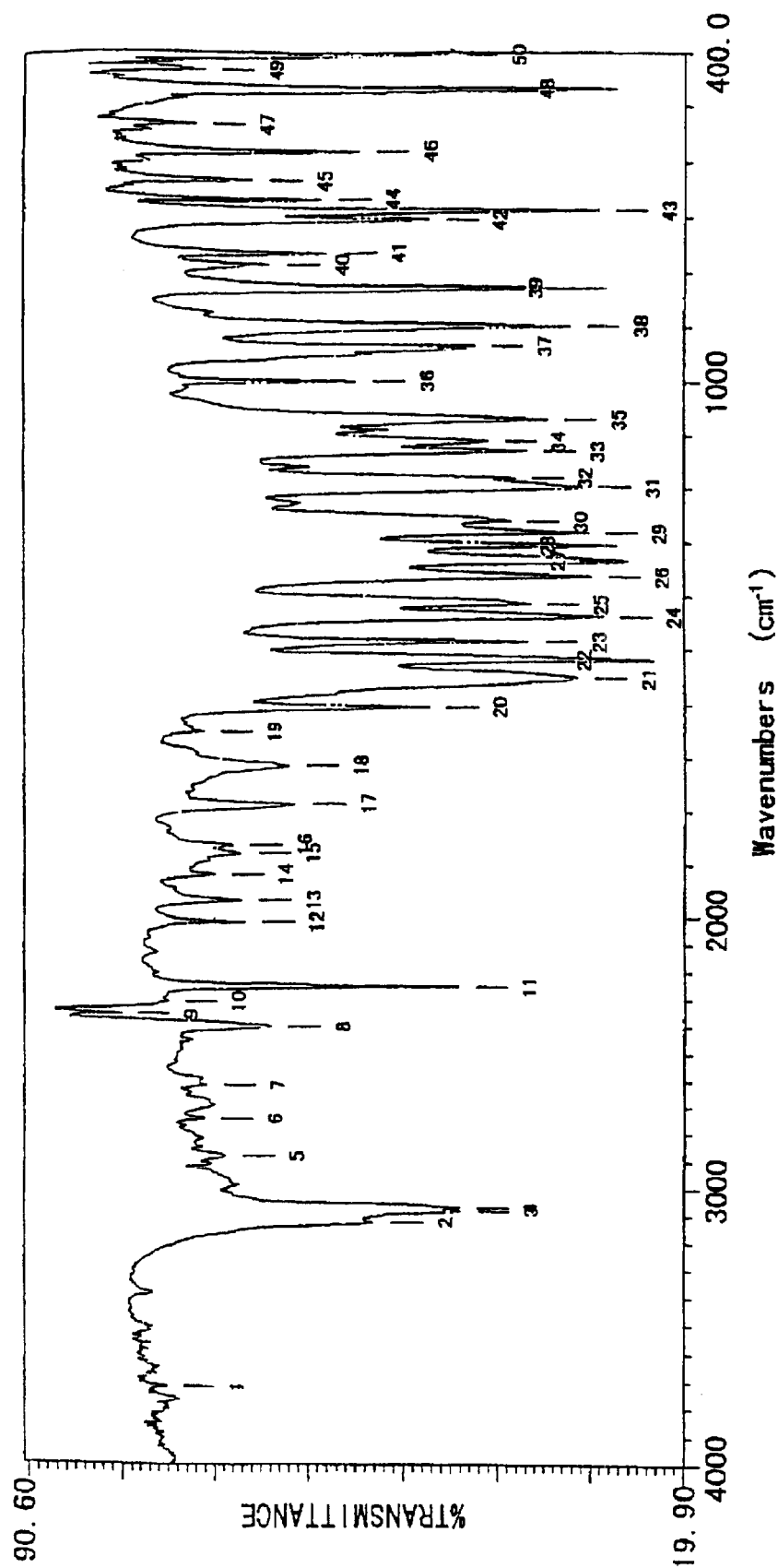
FIG. 35 is an infrared absorption spectrum.

The compound (d) was mixed with 0.1 mol of diaminomaleonitrile, 0.01 mol of p-toluenesulfonic acid and 200 ml of dioxane. The mixture was refluxed for 2 hours and then allowed to be cooled to room temperature, followed by removal of the solvent by distillation. The residue was mixed with 200 ml of methanol to precipitate crystals. The crystals were collected by filtration, washed several times with methanol and dried. The crystals were then isolated by column chromatography using dichloromethane as a developing solvent to obtain a crude product. This was recrystallized from dioxane to obtain the nitrile derivative (C) of the formula (32) with a yield of 55%. The nitrile derivative was found to have a melting point of 279–284° C. An infrared absorption spectrum of the nitrile derivative (C) is shown in FIG. 35. The results of the elementary analysis are shown in Table 15.

TABLE 15

(32)

[Structure of compound (32)]

| | C | H | N |
|---|---|---|---|
| Calculated | 64.67 | 1.81 | 33.52 |
| Found | 64.55 | 1.87 | 33.40 |

0.0016 Mole of the nitrile derivative (C) of the formula (32), 0.32 mol of phthalonitrile, 0.09 mol of Ti(OBu)$_4$, 0.16 mole of urea and 200 ml of octanol were mixed with stirring. The mixture was gradually heated to 150° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain a reaction product with a yield of 71%.

Figure 30:
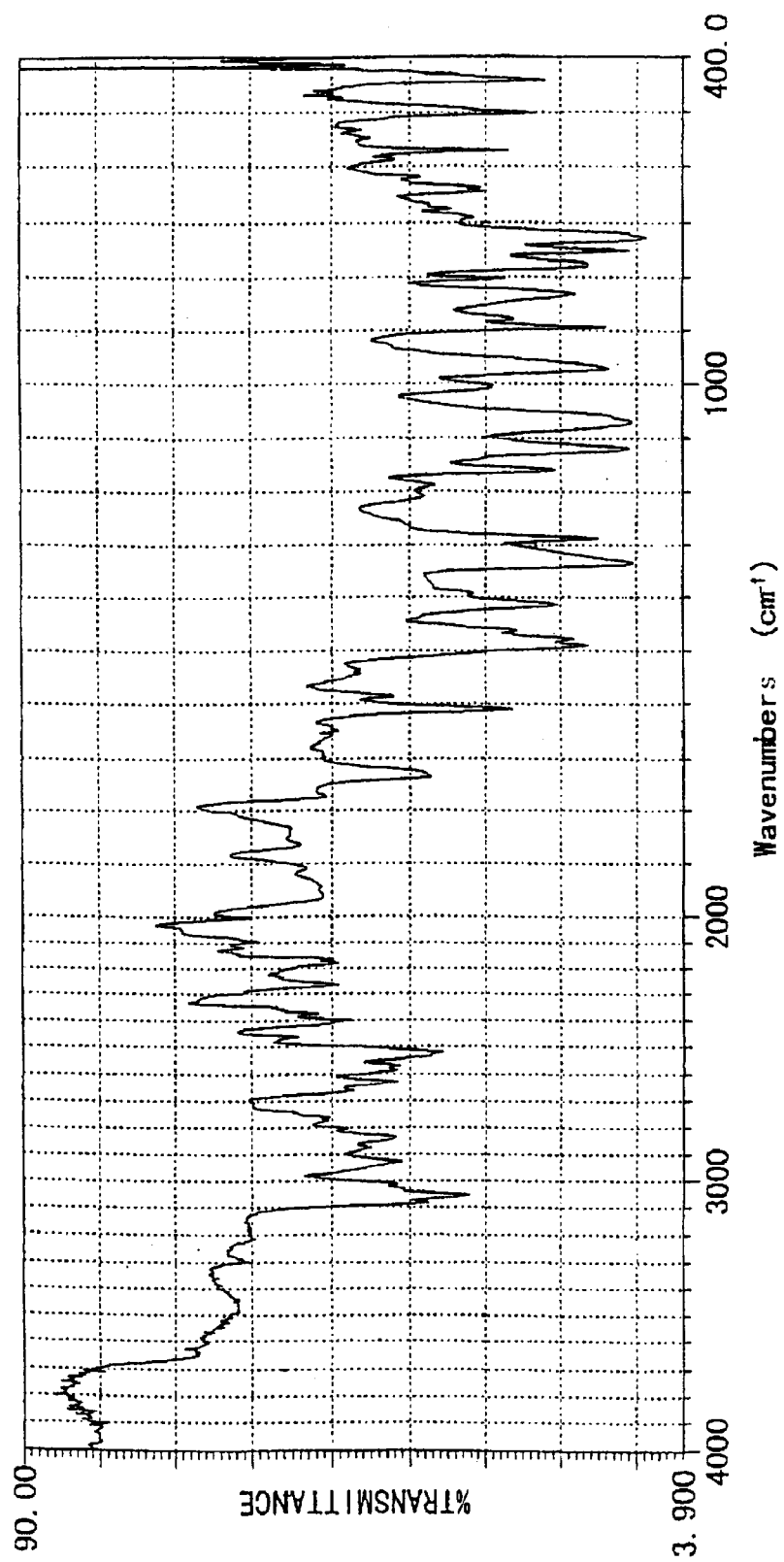
FIG. 30 is an infrared absorption spectrum.

This product (20 g) was then subjected to an acid treatment using an acid pasting method. Thus, the product was dissolved little by little with stirring in 200 g of concentrated sulfuric acid while being cooled in an ice bath. The mixture was then reacted for 1 hour and subsequently poured into 2000 ml of ice water to form crystals. The crystals were separated by filtration and washed with distilled water until no acid was detected in the washed water. After drying, 18 g of a reaction product was obtained. An infrared absorption spectrum of the reaction product is shown in FIG. 30.

EXAMPLE 6

[Crystal Treatment 1 of Compound No. 1-C]

The reaction product (1 g) obtained in Example 3 (reaction product after the acid pasting treatment (the same shall apply hereinafter)) was placed in an Erlenmeyer flask together with 20 ml of N,N-dimethylformamide and heated under reflux conditions for 4 hours. The mixture was cooled to room temperature and filtered to collect solids. The solids were dried to obtain 0.96 g of a reaction product.

EXAMPLE 7

[Crystal Treatment 2 of Compound No. 1-C]

The reaction product (1 g) obtained in Example 3 was placed in an Erlenmeyer flask together with 20 ml of methyl ethyl ketone and heated under reflux conditions for 4 hours. The mixture was cooled to room temperature and filtered to collect solids. The solids were dried to obtain 0.97 g of a reaction product.

EXAMPLE 8

[Crystal Treatment 3 of Compound No. 1-C]

The reaction product (1 g) obtained in Example 3 was placed in an Erlenmeyer flask together with 20 ml of o-chlorobenzene and heated under reflux conditions for 4 hours. The mixture was cooled to room temperature and filtered to collect solids. The solids were dried to obtain 0.97 g of a reaction product.

EXAMPLE 9

[Crystal Treatment 4 of Compound No. 1-C]

The reaction product (1 g) obtained in Example 3 was placed in an Erlenmeyer flask together with 20 ml of cyclohexanone and heated under reflux conditions for 4 hours. The mixture was cooled to room temperature and filtered to collect solids. The solids were dried to obtain 0.98 g of a reaction product.

EXAMPLE 10

0.0016 Mole of the nitrile derivative (B) of the formula (31) obtained in Example 4, 0.32 mol of phthalonitrile, 0.09 mol of $Ti(OBu)_4$, 0.16 mole of urea and 200 ml of octanol was gradually heated to 150° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain a reaction product with a yield of 70%.

This product (5 g) was dissolved little by little with stirring in 50 g of concentrated sulfuric acid while being cooled in an ice bath. The mixture was then reacted for 1 hour and subsequently poured into 500 ml of ice water to form crystals. The crystals were separated by filtration and washed with distilled water until no acid was detected in the washed water, thereby obtaining 20 g of a wet cake (solid matter content: 20%).

EXAMPLE 11

The wet cake (15 g) of the reaction product obtained in Example 10 was mixed with 12 g of distilled water and 120 g of tetrahydrofuran with stirring for 6 hours. The mixture was then filtered and the solid phase was dried to obtain 3.5 g of a reaction product.

EXAMPLE 12

The wet cake (15 g) of the reaction product obtained in Example 10 was mixed with 12 g of distilled water and 120 g of toluene at room temperature with stirring for 6 hours. The mixture was then filtered and the solid phase was dried to obtain 3.6 g of a reaction product.

EXAMPLE 13

The wet cake (15 g) of the reaction product obtained in Example 10 was mixed with 12 g of distilled water and 120 g of 1,4-dioxane at room temperature with stirring for 6 hours. The mixture was then filtered and the solid phase was dried to obtain 3.6 g of a reaction product.

EXAMPLE 14

The wet cake (15 g) of the reaction product obtained in Example 10 was mixed with 12 g of distilled water and 120 g of N,N-dimethylformamide at 80° C. with stirring for 6 hours. The mixture was then filtered and the solid phase was dried to obtain 3.6 g of a reaction product.

EXAMPLE 15

[Preparation of Product 1-B]

1.95 Grams (4.0 mols) of the intermediate product nitrile derivative (A) of the formula (6) obtained in Example 1, 105.64 g (0.808 mol) of phthalonitrile, 74.87 g (0.22 mols) of $Ti(OBu)_4$, 24.26 g (0.400 mol) and 100 ml of 1-octanol were placed in a reactor and gradually heated to 155° C. and maintained at 150–155° C. with stirring under a nitrogen gas stream for 5 hours. After completion of the reaction, the reaction mixture was allowed to be cooled to 70° C. and mixed with 400 ml of methanol. The mixture was again heated at 70° C. with stirring for 45 minutes. After being allowed to stand overnight, the solid phase was then filtered, washed thrice with toluene, twice with methanol and once with water and dried to obtain a reaction product.

EXAMPLE 16

The reaction product (40.0 g) obtained in Example 15 was added little by little to 640 g of concentrated sulfuric acid through 30 minutes while maintaining the temperature at 4–9° C. The mixture was then heated at 6–9° C. for 1 hour with stirring and then added dropwise in 4 liters of ice water through 30 minutes. After stirring for 30 minutes, solids were separated by filtration. The separated solid phase was mixed with 4 liters of ion-exchanged water with stirring and again filtered. Such washing and filtration procedures were repeated 4 times more to obtain 297.7 g of a wet cake (solid matter content: 12.7%, yield: 94.5%).

EXAMPLE 17

The wet cake (153.86 g) obtained in Example 16 was dried in a vacuum dryer at 70° C. for 2 days to obtain 19.52 g of a reaction product.

EXAMPLE 18

The reaction product obtained in Example 15 was subjected to an acid-paste treatment using concentrated sulfuric acid in the same manner as described in Example 16 to obtain a wet cake. The wet cake (8.00 g, solid matter content: 13.1%) was mixed with 2.5 g of ion-exchanged water and 42.0 g of 1-methyl-2-pyrrolidinone with stirring at room temperature for 6 hours. This was then mixed with methanol and the solid phase was separated by filtration to give 1.03 g of a reaction product (yield: 98.1%)

EXAMPLE 19

The wet cake (8.00 g) obtained in Example 16 was mixed with 2.5 g of ion-exchanged water and 42.0 g of 1-methyl-2-pyrrolidinone with stirring at room temperature for 2 hours. This was then mixed with methanol and the solid phase was separated by filtration to give 1.01 g of a reaction product (yield: 99.6%).

EXAMPLE 20

Example 19 was repeated in the same manner as described except that the stirring time was increased to 48 hours. 1.01 Grams of a reaction product was obtained (yield: 99.6%)

EXAMPLE 21

Example 18 was repeated in the same manner as described except that 1,3-dimethyl-2-imidazoline was substituted for 1-methyl-2-pyrrolidinone. 1.04 Grams of a reaction product was obtained (yield: 99.0%).

EXAMPLE 22

Example 18 was repeated in the same manner as described except that the stirring time was increased to 30 hours. 1.01 Grams of a reaction product was obtained (yield: 99.6%).

EXAMPLE 23

Example 18 was repeated in the same manner as described except that the treatment temperature was raised to 80° C. 1.01 Grams of a reaction product was obtained (yield: 99.6%)

EXAMPLE 24

In a mixed solvent containing 2 ml of trifluoroacetic acid and 8 ml of dichloromethane, 1 g of the reaction product obtained in Example 3 was dissolved. The mixture was then stirred for 1 hour and subsequently added dropwise through 5 minutes to a mixed solvent composed of 100 ml of dichloromethane and 100 ml of methanol in an ice bath with stirring to form crystals. The crystals were separated by filtration and washed with distilled water until no acid was detected in the washed water and dried, thereby obtaining a reaction product.

EXAMPLE 25

In a mixed solvent containing 2 ml of trifluoroacetic acid and 8 ml of dichloromethane, 1 g of the reaction product obtained in Example 3 was dissolved. The mixture was then stirred for 1 hour and subsequently added dropwise through 75 minutes to a mixed solvent composed of 100 ml of dichloromethane and 100 ml of methanol in an ice bath with stirring to form crystals. The crystals were separated by filtration and washed with distilled water until no acid was detected in the washed water and dried, thereby obtaining a reaction product.

EXAMPLE 26

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 200 ml of ice water to form crystals. The crystals were separated by filtration and washed with distilled water until no acid was detected in the washed water and dried, thereby obtaining a reaction product.

EXAMPLE 27

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 50 ml of N,N-dimethylformamide in an ice bath with stirring. Thereafter, 50 ml of methanol was added to the mixture and stirred for 1 hour to form crystals. The crystals were separated by filtration and washed with distilled water until no acid was detected in the washed water and dried, thereby obtaining a reaction product.

EXAMPLE 28

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 50 ml of cylohexane in an ice bath with stirring. Thereafter, 50 ml of methanol was added to the mixture and stirred for 1 hour to form crystals. The crystals were separated by filtration and washed with distilled water until no acid was detected in the washed water and dried, thereby obtaining a reaction product.

EXAMPLE 29

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 50 ml of isopropyl ether in an ice bath with stirring. Thereafter, 50 ml of methanol was added to the mixture and stirred for 1 hour to form crystals. The crystals were separated by filtration and washed with distilled water until no acid was detected in the washed water and dried, thereby obtaining a reaction product.

EXAMPLE 30

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 50 ml of methyl ethyl ketone in an ice bath with stirring. Thereafter, 50 ml of methanol was added to the mixture and stirred for 1 hour to form crystals. The crystals were separated by filtration and washed with distilled water until no acid was detected in the washed water and dried, thereby obtaining a reaction product.

EXAMPLE 31

In a mixed solvent containing 2 ml of trifluoroacetic acid and 8 ml of dichloromethane, 1 g of the reaction product obtained in Example 3 was dissolved. The mixture was then stirred for 1 hour and subsequently added dropwise through 5 minutes to 50 ml of methanol with stirring in an ice bath to form crystals. The crystals were separated by filtration and washed with distilled water until no acid was detected in the washed water and dried, thereby obtaining a reaction product.

EXAMPLE 32

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 5 minutes to 50 ml of tetrahydrofuran in an ice bath with stirring. Thereafter, 50 ml of methanol was added to the mixture and stirred for 1 hour to form crystals. The crystals were separated by filtration and washed with distilled water until no acid was detected in the washed water and dried, thereby obtaining a reaction product.

EXAMPLE 33

In a mixed solvent containing 2 ml of trifluoroacetic acid and 8 ml of dichloromethane, 1 g of The reaction product obtained in Example 3 was added through 1 minute. The mixture was then stirred for 45 minutes at room temperature to dissolve the Product and then allowed to sand for 25 minutes. After removal of the supernatant, the mixture was mixed with 50 ml of methanol to form crystals. The crystals were separated by filtration, placed in a beaker, washed with hot water, and then filtered. Such washing with hot water and filtration procedures were repeated two times more. Thereafter, the crystals were dispersed in 50 ml of fluorobenzene, stirred for 15 minutes at room temperature, separated by filtration and dried to obtain a reaction product.

EXAMPLE 34

In a mixed solvent containing 2 ml of trifluoroacetic acid and 8 ml of dichloromethane, 1 g of The reaction product obtained in Example 3 was dissolved. The mixture was then stirred for 1 hour and subsequently added dropwise through 20 seconds to a mixed solvent consisting of 100 ml of dichloromethane and 100 ml methanol with stirring in an ice bath to form crystals. The crystals were separated by filtration and washed with distilled water until no acid was detected in the washed water and dried, thereby obtaining a reaction product.

Each of the products or treated products obtained in Examples 6–14, 18–22 and 24–34 was measured for X-ray diffraction spectrum thereof to give the results shown in FIGS. 1–24 and 28, respectively. The X-ray diffraction spectra were measured under conditions shown below. Wet cake samples were measured after having been dried.

| X-ray tube: | Cu (wavlength: 1.54 Å) |
|---|---|
| Voltage: | 50 kV |
| Current: | 30 mA |
| Scanning speed: | 2 deg/min. |
| Scanning scope: | 3–40 deg |

Figure 5:
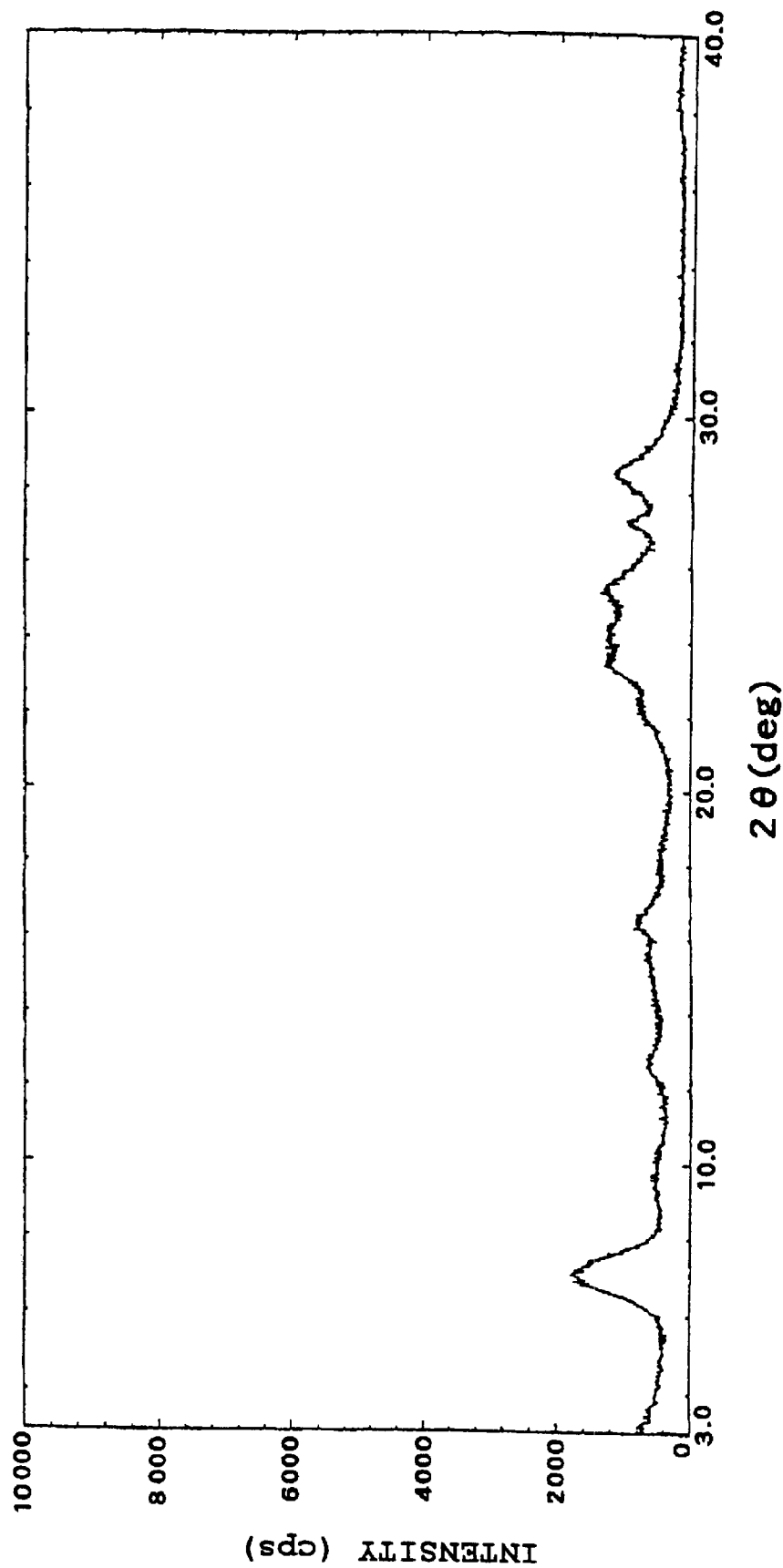
FIG. 5 is an X-ray diffraction spectrum of a reaction product obtained in Example 10.
Figure 6:
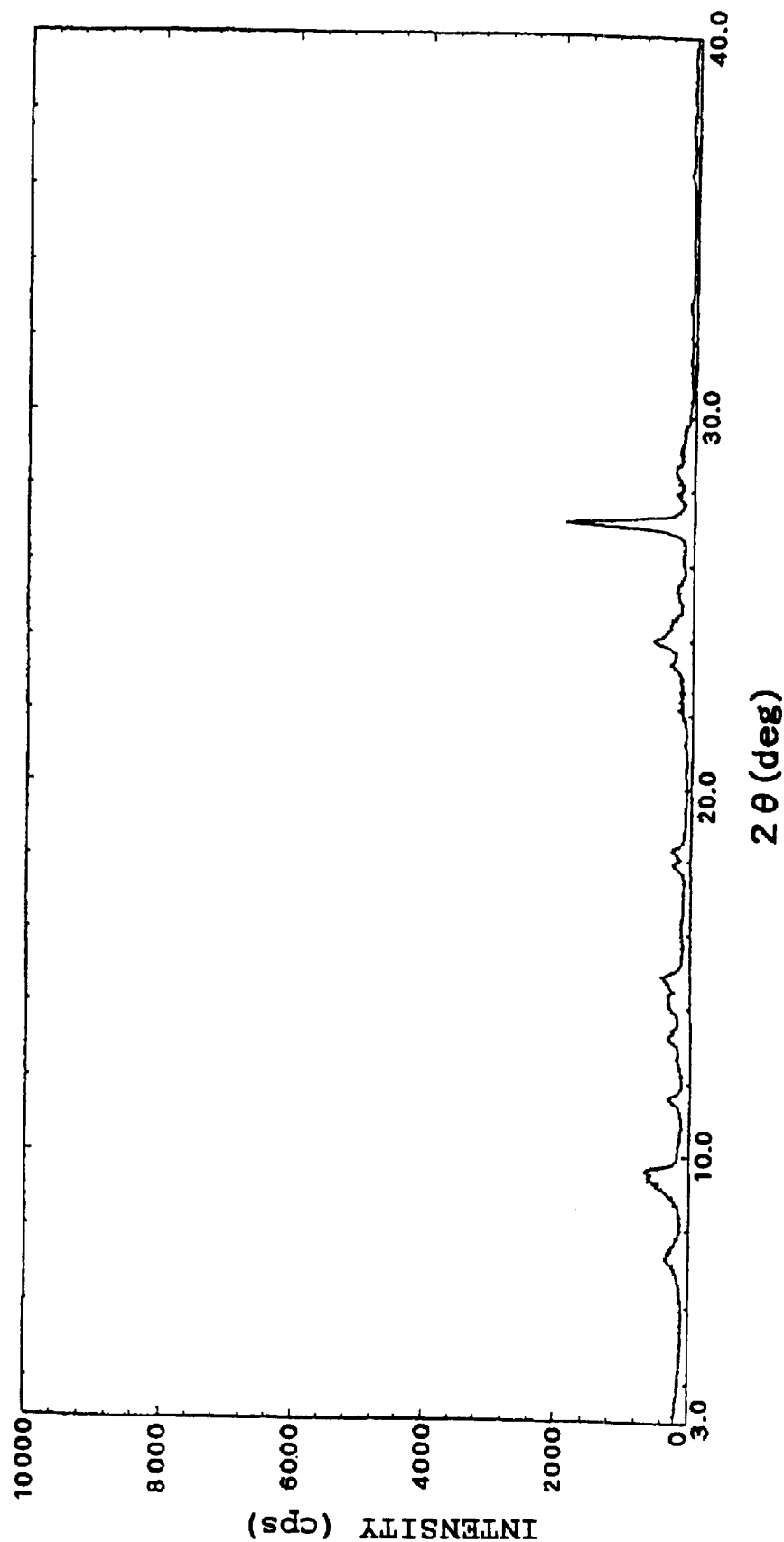
FIG. 6 is an X-ray diffraction spectrum of a reaction product obtained in Example 11.
Figure 7:
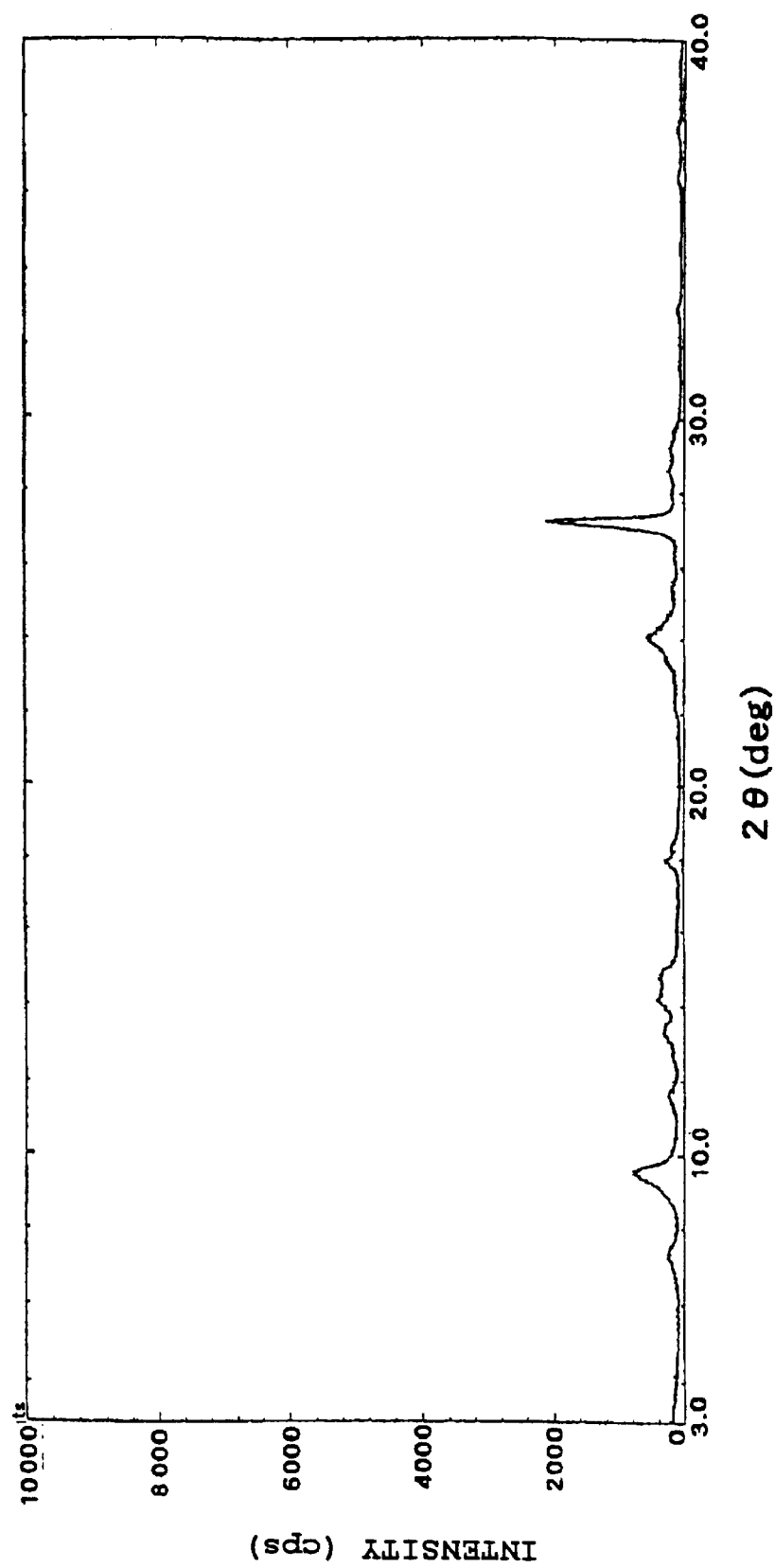
FIG. 7 is an X-ray diffraction spectrum of a reaction product obtained in Example 12.
Figure 8:
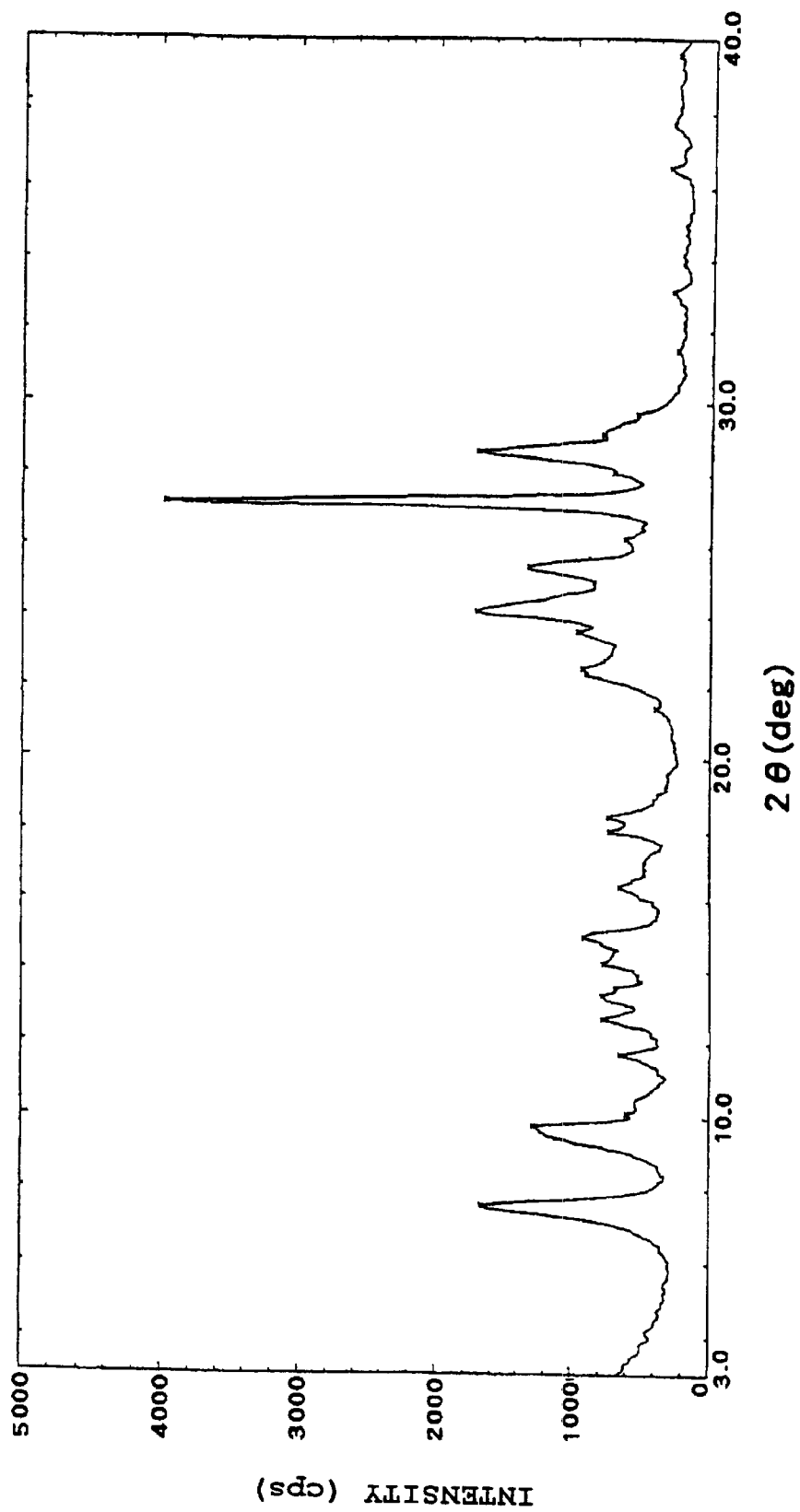
FIG. 8 is an X-ray diffraction spectrum of a reaction product obtained in Example 13.
Figure 9:
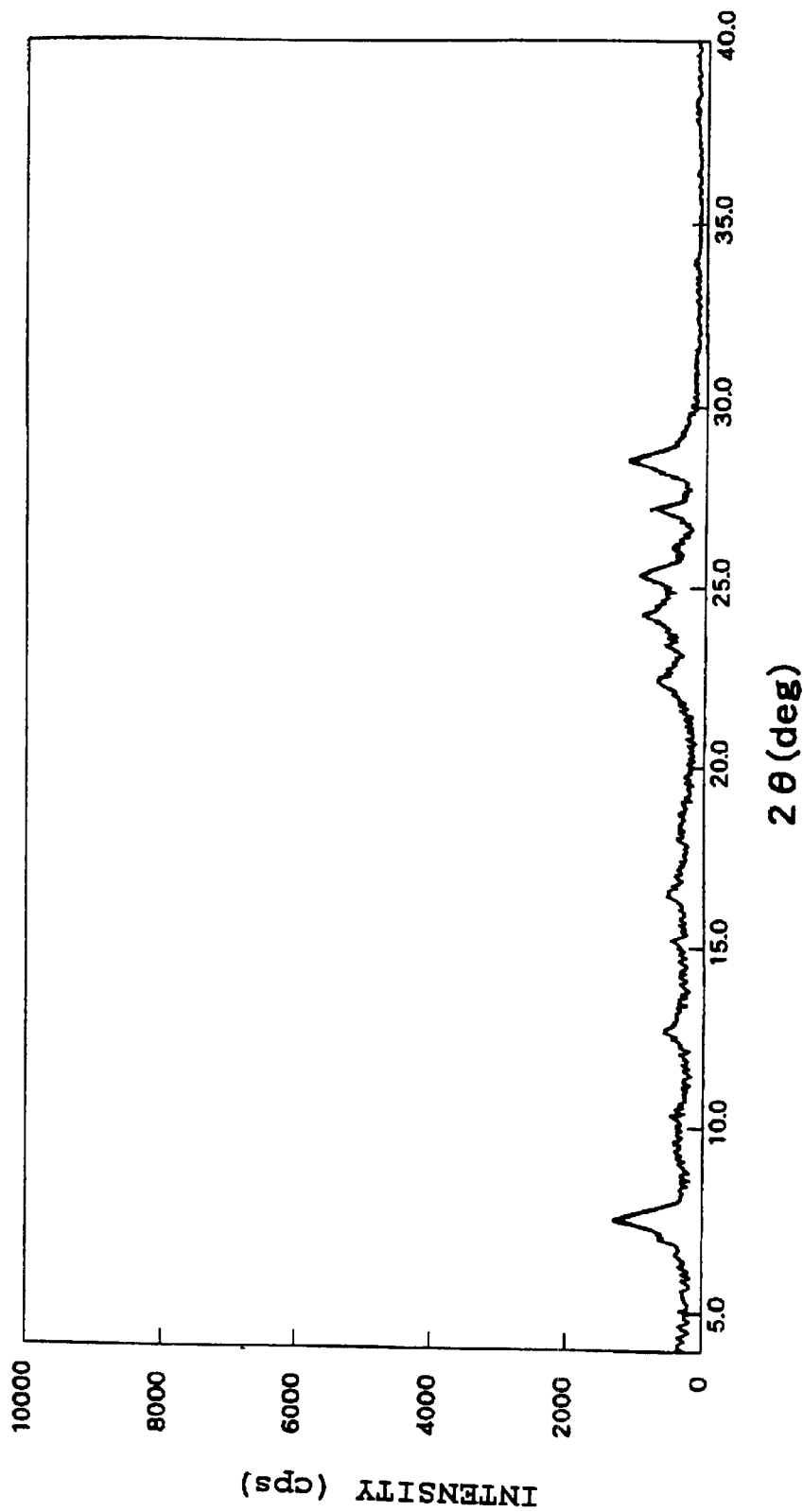
FIG. 9 is an X-ray diffraction spectrum of a reaction product obtained in Example 14.
Figure 10:
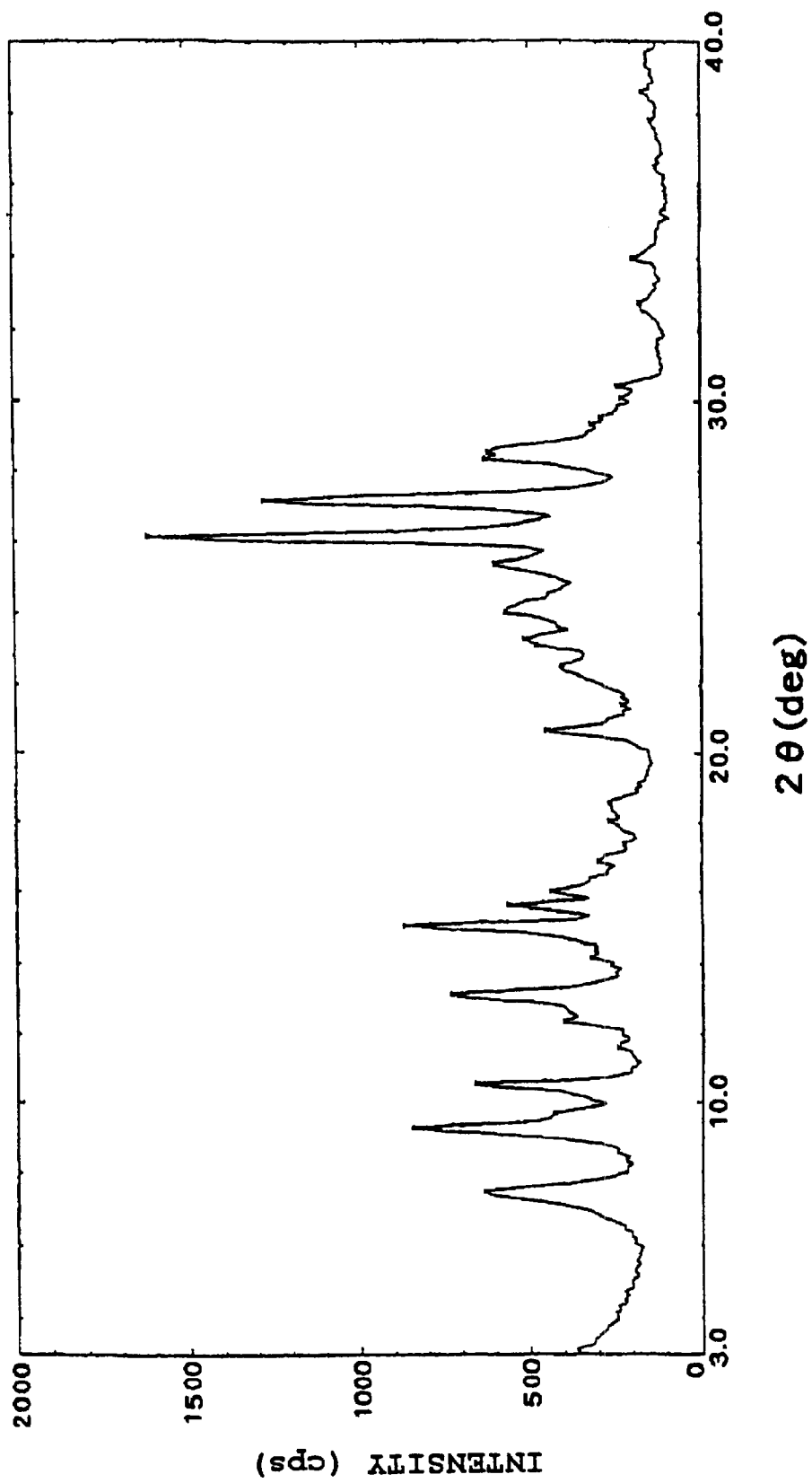
FIG. 10 is an X-ray diffraction spectrum of a reaction product obtained in Example 18.
Figure 11:
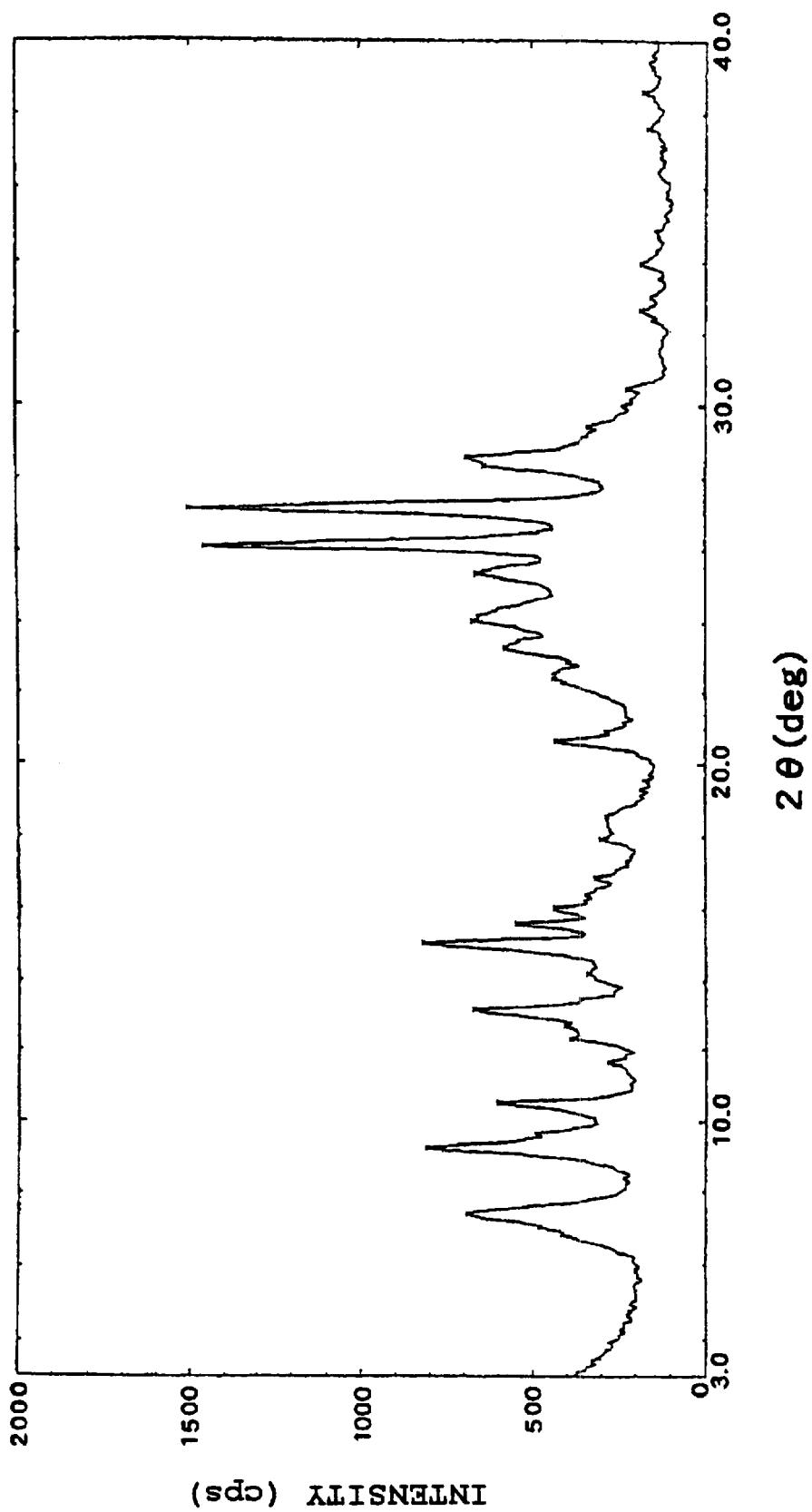
FIG. 11 is an X-ray diffraction spectrum of a reaction product obtained in Example 19.
Figure 12:
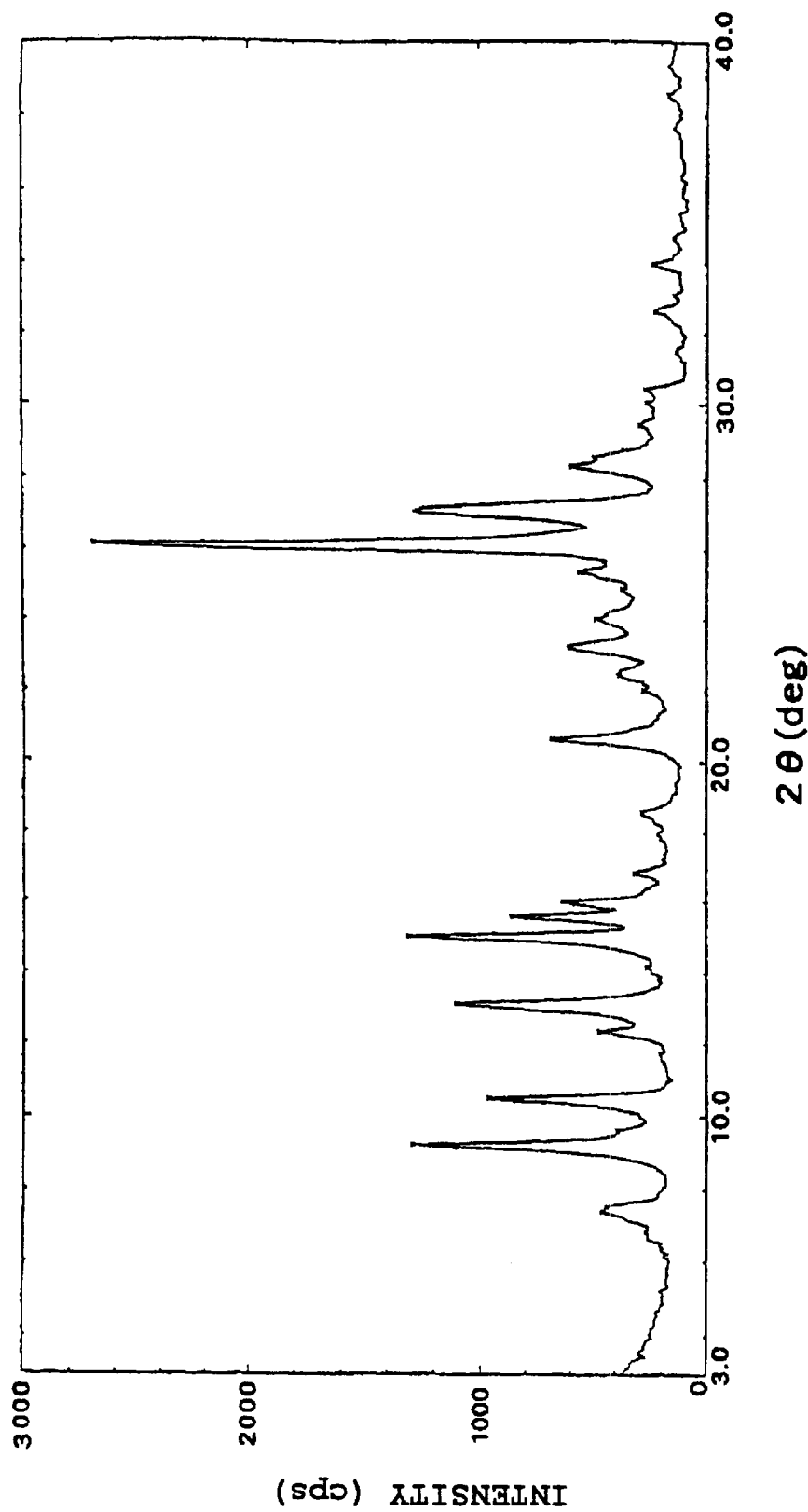
FIG. 12 is an X-ray diffraction spectrum of a reaction product obtained in Example 20.
Figure 13:
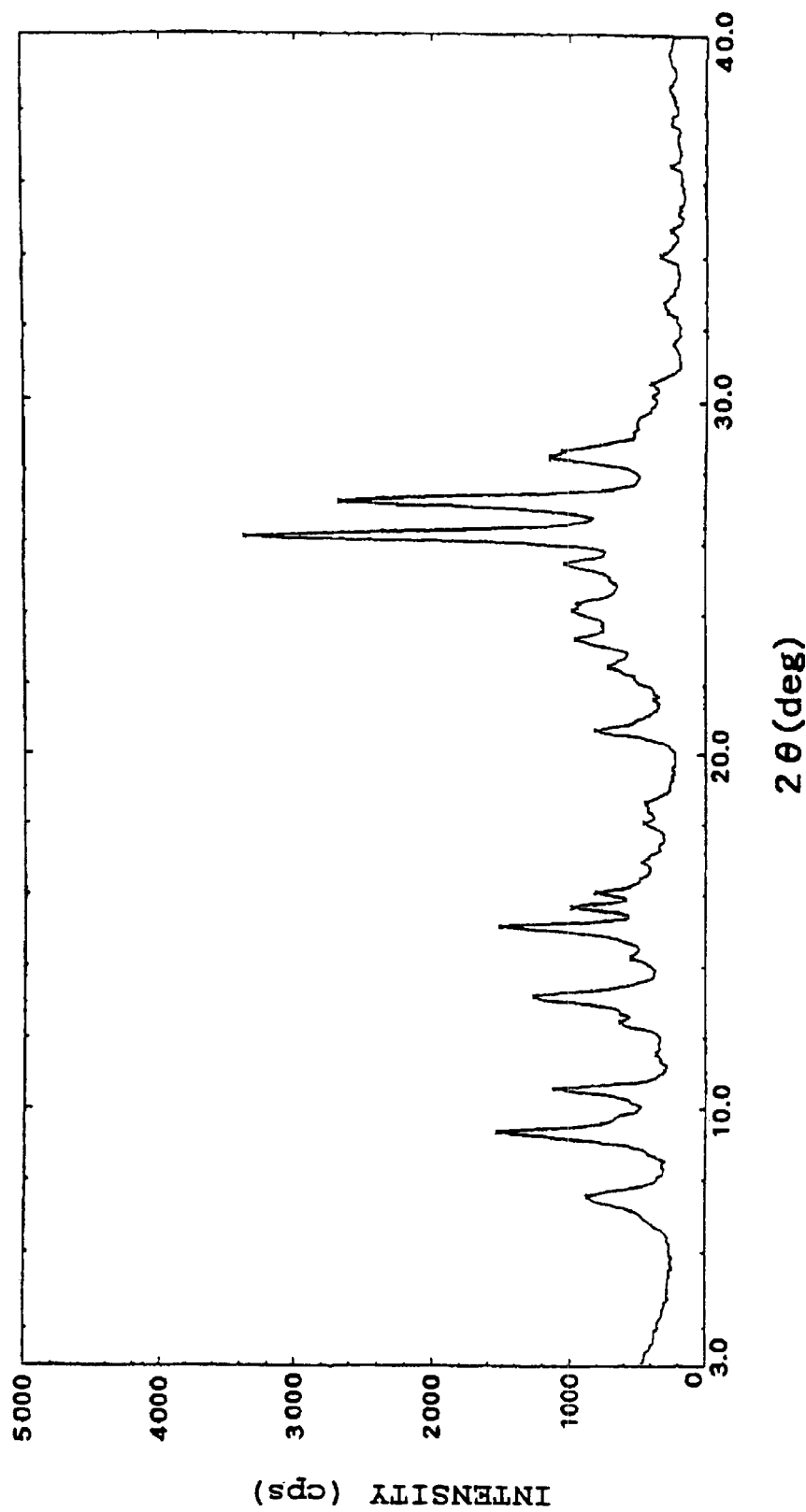
FIG. 13 is an X-ray diffraction spectrum of a reaction product obtained in Example 21.
Figure 14:
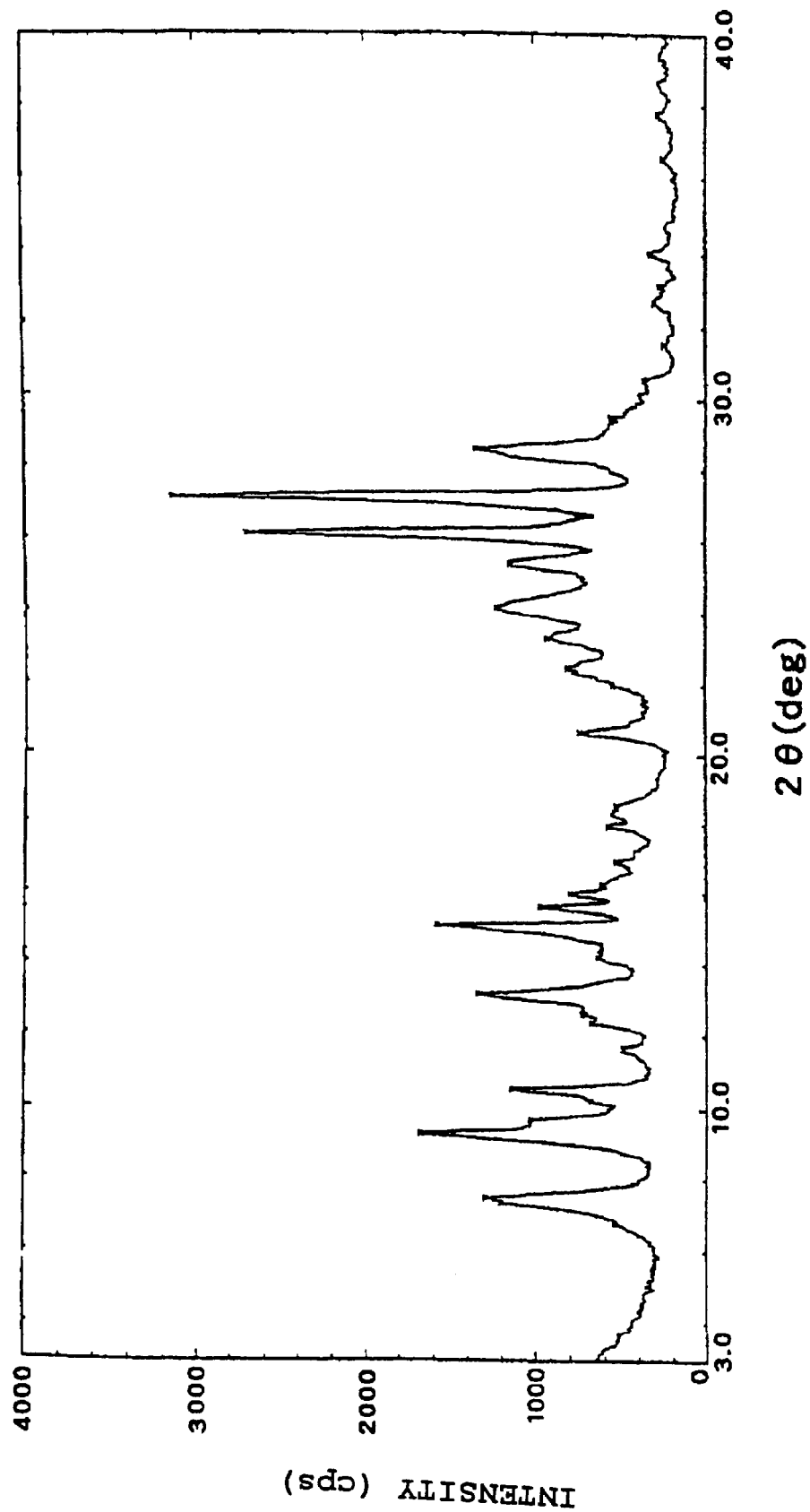
FIG. 14 is an X-ray diffraction spectrum of a reaction product obtained in Example 22.
Figure 15:
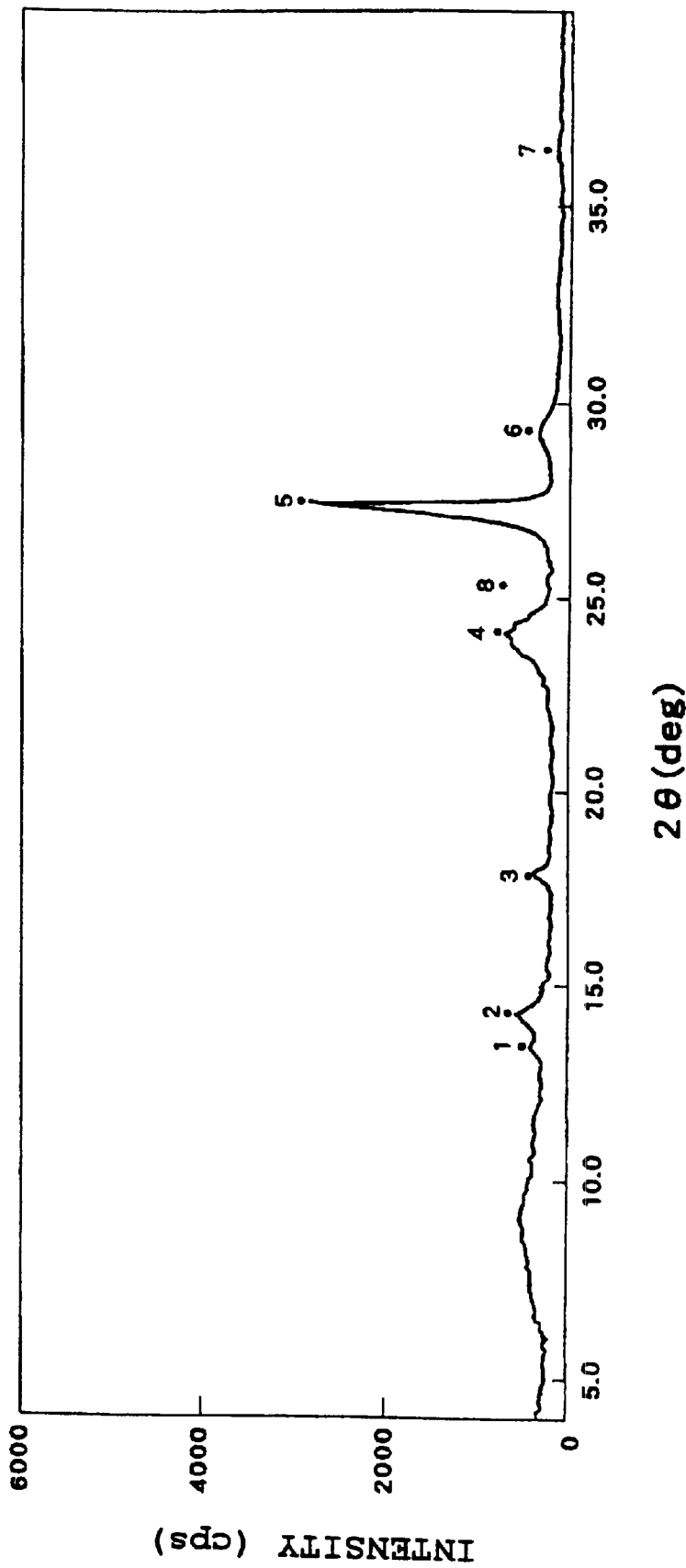
FIG. 15 is an X-ray diffraction spectrum of a reaction product obtained in Example 24.
Figure 16:
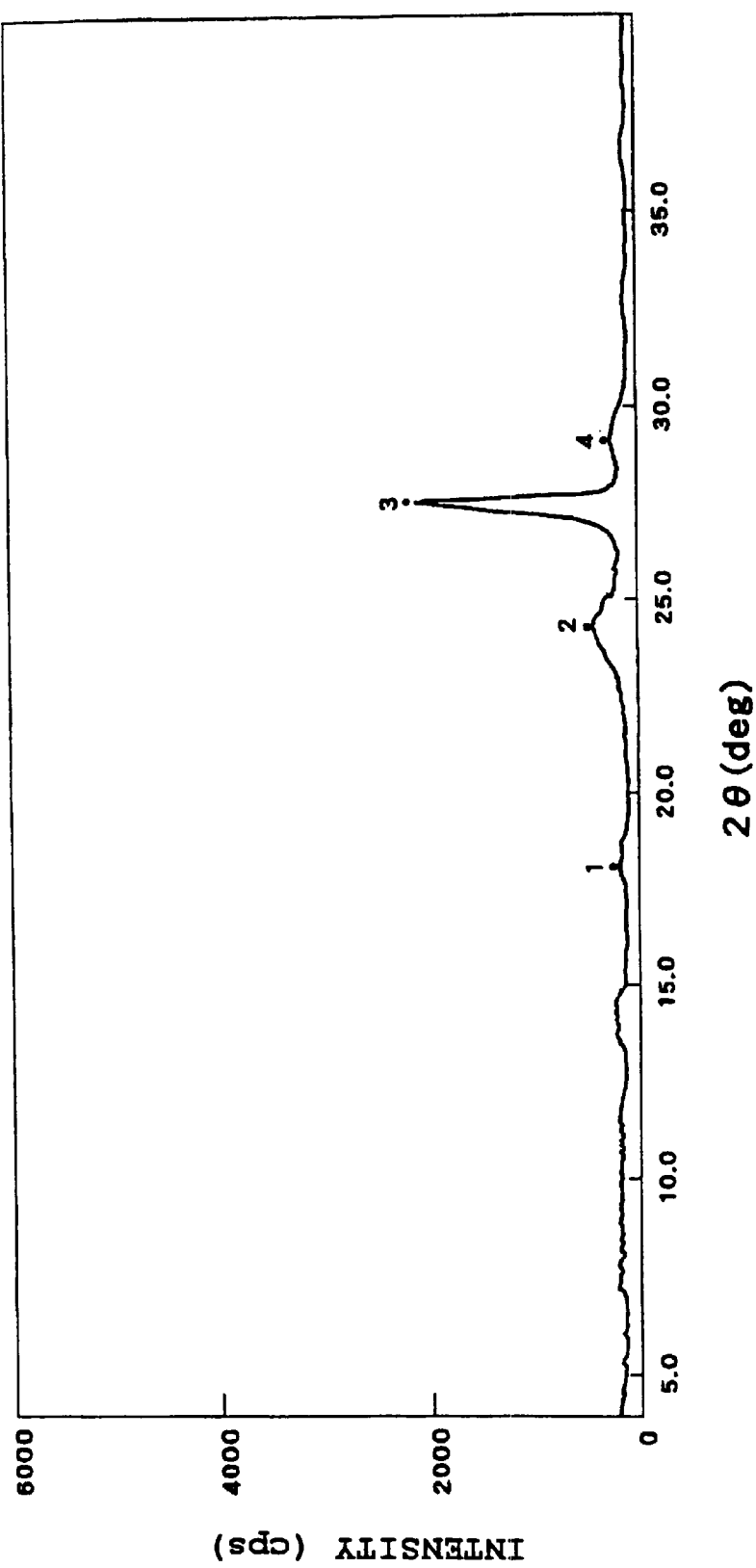
FIG. 16 is an X-ray diffraction spectrum of a reaction product obtained in Example 25.

The X-ray diffraction spectrum shown in FIG. 5 has no diffraction peaks having a half-value width of 1° or less, indicating that the product is amorphous. The X-ray diffraction spectra of FIGS. 1–4 and 6–24 have peaks with a half-value width of 1° or less, indicating that the products are crystalline in nature. Further, differences in the X-ray patterns suggest that the crystal structures of the products are different from each other.

EXAMPLE 35

Example 2 was repeated in the same manner as described except that 1,3-diiminoindoline ($R_2$–$R_5$=H in the general formula (3)) was substituted for the phthalonitrile. In this case, a crystalline reaction product similar to the product of Example 2 was obtained. Using this product, Example 24 was repeated in the same manner as described. It was confirmed that the resulting product had charge generating properties.

Application Example 1

A dispersion containing 3 parts of the product obtained in Example 24, 1 part of polyvinyl butyral resin (BM-S manufactured by Sekisui Chemical Co., Ltd.) and 80 parts of methyl ethyl ketone was placed in a ball mill pot and milled for 3 hours using PSZ balls with a diameter of 2 mm to obtain a coating liquid for forming a charge generation layer. This was applied on an aluminum plate and dried at 100° C. for 20 minutes to form a charge generation layer having a thickness of about 0.3 μm. A coating liquid for forming a charge transport layer was prepared by mixing 7 parts by weight of a positive hole charge transporting material of the formula (33) shown below, 10 parts by weight of a commercially available polycarbonate resin (PCX-5 manufactured by Teijin Chemicals Ltd.), 68 parts by weight of dichloromethane and 0.0002 part by weight of a commercially available silicone oil (KF50 manufactured by Shin-Etsu Chemical Co., Ltd.). The coating liquid was applied on the above-prepared charge generation layer and dried at 110° C. for 20 minutes to obtain a charge transport layer having a thickness of about 28 μm, thereby obtaining an electrophotographic photoconductor.

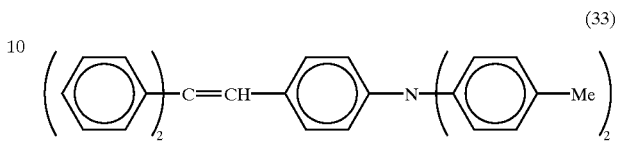

(33)

Application Example 2

Application Example 1 was repeated in the same manner as described except that the product obtained in Example 25 was substituted for the product of Example 24, thereby obtaining an electrophotographic photoconductor of Application Example 2.

Application Example 3

Application Example 1 was repeated in the same manner as described except that the product obtained in Example 26 was substituted for the product of Example 24, thereby obtaining an electrophotographic photoconductor of Application Example 3.

Application Example 4

Application Example 1 was repeated in the same manner as described except that the product obtained in Example 27 was substituted for the product of Example 24, thereby obtaining an electrophotographic photoconductor of Application Example 4.

Application Example 5

Application Example 1 was repeated in the same manner as described except that the product obtained in Example 28 was substituted for the product of Example 24, thereby obtaining an electrophotographic photoconductor of Application Example 5.

Application Example 6

Application Example 1 was repeated in the same manner as described except that the product obtained in Example 29 was substituted for the product of Example 24, thereby obtaining an electrophotographic photoconductor of Application Example 6.

Application Example 7

Application Example 1 was repeated in the same manner as described except that the product obtained in Example 30 was substituted for the product of Example 24, thereby obtaining an electrophotographic photoconductor of Application Example 7.

Application Example 8

Application Example 1 was repeated in the same manner as described except that the product obtained in Example 31 was substituted for the product of Example 24, thereby obtaining an electrophotographic photoconductor of Application Example 8.

Application Example 9

Application Example 1 was repeated in the same manner as described except that the product obtained in Example 32 was substituted for the product of Example 24, thereby obtaining an electrophotographic photoconductor of Application Example 9.

Application Example 10

Application Example 1 was repeated in the same manner as described except that the product obtained in Example 33 was substituted for the product of Example 24, thereby obtaining an electrophotographic photoconductor of Application Example 10.

Application Example 11

Application Example 1 was repeated in the same manner as described except that a positive hole charge transporting material represented by the formula (34) below was substituted for the charge transporting material (33), thereby obtaining an electrophotographic photoconductor of Application Example 11.

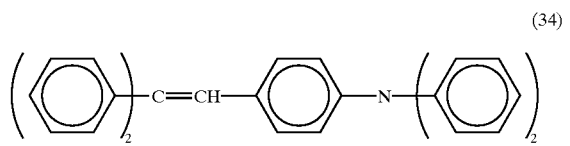

(34)

Application Example 12

Application Example 1 was repeated in the same manner as described except that a positive hole charge transporting material represented by the formula (35) below was substituted for the charge transporting material (33), thereby obtaining an electrophotographic photoconductor of Application Example 12.

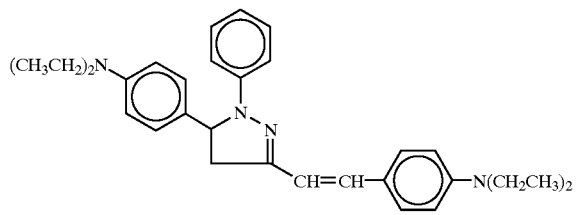

(35)

Application Example 13

Application Example 1 was repeated in the same manner as described except that a positive hole charge transporting material represented by the formula (36) below was substituted for the charge transporting material (33), thereby obtaining an electrophotographic photoconductor of Application Example 13.

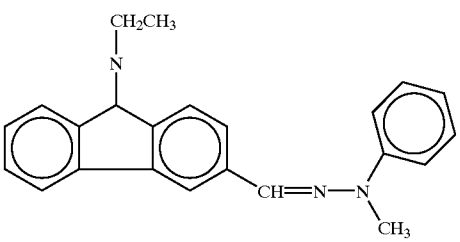

(36)

Application Example 14

Application Example 1 was repeated in the same manner as described except that the product obtained in Example 6 was substituted for the product of Example 24, thereby obtaining an electrophotographic photoconductor of Application Example 14.

Application Example 15

Application Example 1 was repeated in the same manner as described except that the product obtained in Example 7 was substituted for the product of Example 24, thereby obtaining an electrophotographic photoconductor of Application Example 15.

Application Example 16

Application Example 1 was repeated in the same manner as described except that the product obtained in Example 12 was substituted for the product of Example 24, thereby obtaining an electrophotographic photoconductor of Application Example 16.

Comparative Example 0.1 Mole of phthalocyanine, 0.025 mol of Ti(OBu)$_4$, 0.05 mol of urea and 200 ml of octanol were mixed with stirring. The mixture was gradually heated to 150° C. and maintained at 150–160° C. with stirring under a nitrogen gas stream for 6 hours. After completion of the reaction, the reaction mixture was allowed to be cooled and filtered. The solid phase was then washed well with octanol and then several times with methanol, toluene and water and dried to obtain titanylphthalocyanine with a yield of 70%.

Figure 25:
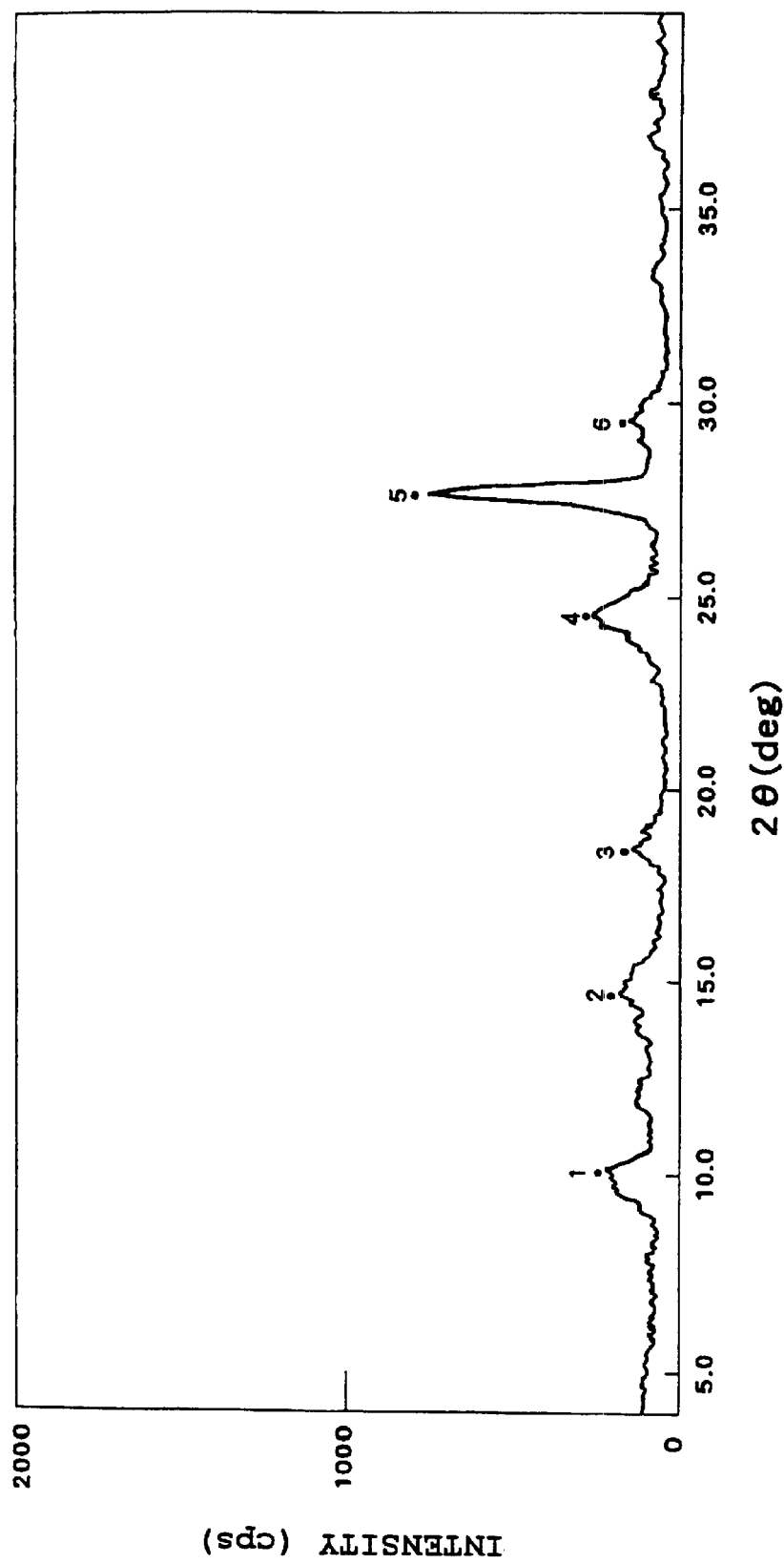
FIG. 25 is an X-ray diffraction spectrum of a reaction product obtained in Comparative Example.

In a mixed solvent containing 2 ml of trifluoroacetic acid and 8 ml of dichloromethane, 1 g of the thus obtained titanylphthalocyanine was added through 1 minute. The mixture was then stirred for 45 minutes at room temperature to dissolve the titanylphthalocyaine and then allowed to sand for 25 minutes. After removal of the supernatant, the mixture was mixed with 50 ml of methanol to form crystals. The crystals were separated by filtration, placed in a beaker, washed with 200 ml of hot water, and then filtered. Such washing with hot water and filtration procedures were repeated two times more. Thereafter, the crystals were dispersed in 50 ml of fluorobenzene, stirred for 15 minutes at room temperature, separated by filtration and dried to obtain treated titanylphthalocyanine whose X-ray diffraction spectrum measured in the same conditions as those giving FIGS. 1–24 is shown in FIG. 25.

Application Example 1 was repeated in the same manner as described except that the above treated titanylphthalocyanine was substituted for the product of Example 24, thereby obtaining an electrophotographic photoconductor of Comparative Example.

The photoconductors obtained in Application Examples 1–16 and Comparative Example were measured for their electrostatic characteristics under conditions of 25° C./55% RH using EPA-8100 manufactured by Kawaguchi Electro Works Co., Ltd. in accordance with a dynamic mode. Thus, each photoconductor was negatively charged at −6 kV for 20 seconds. Then the photoconductor was allowed to stand in the dark for 20 seconds and the surface potential $V_0$ [V] was measured. The photoconductor was then irradiated with a monochromatic light with a wavelength of 780 nm such that the illuminance on the surface of the photoconductor was 1 $\mu W/cm^2$. The exposure Em1/2 [$\mu J/cm^2$] required to reduce the surface potential from −800V to −400 V was measured for the evaluation of sensitivity of the photoconductor to light emitted from LD (near infrared region). The results are summarized in Table 16 below.

TABLE 16

|  | $V_0$ [−V] | $Em_{1/2}$ [J/cm$^2$] |
| --- | --- | --- |
| Application Example 1 | 870 | 0.35 |
| Application Example 2 | 1050 | 0.2 |
| Application Example 3 | 950 | 0.4 |
| Application Example 4 | 850 | 0.2 |
| Application Example 5 | 700 | 0.95 |
| Application Example 6 | 720 | 0.3 |
| Application Example 7 | 680 | 0.5 |
| Application Example 8 | 900 | 0.7 |
| Application Example 9 | 1100 | 0.4 |
| Application Example 10 | 1160 | 0.4 |
| Application Example 11 | 600 | 0.8 |
| Application Example 12 | 650 | 1.6 |
| Application Example 13 | 800 | 1.2 |
| Application Example 14 | 900 | 0.5 |
| Application Example 15 | 950 | 0.6 |
| Application Example 16 | 850 | 0.4 |
| Comparative Example | 820 | 0.38 |

The photoconductors obtained in Application Example 1 and Comparative Example were each measured for the electrostatic fatigue characteristics thereof using EPA-8100 manufactured by Kawaguchi Electro Works Co., Ltd. in accordance with a dynamic mode (rotational speed: 1000 rpm). Thus, each photoconductor was repeatedly subjected to negative charging at −6 kV and irradiation with white light for 60 minutes while maintaining the current and potential at 5.6 $\mu A$ and −800V, respectively. The photoconductor obtained in Example 20 was also subjected to the electrostatic fatigue characteristics. The change of the surface potential $V_0$ [V] is shown in Table 17.

Figure 17:
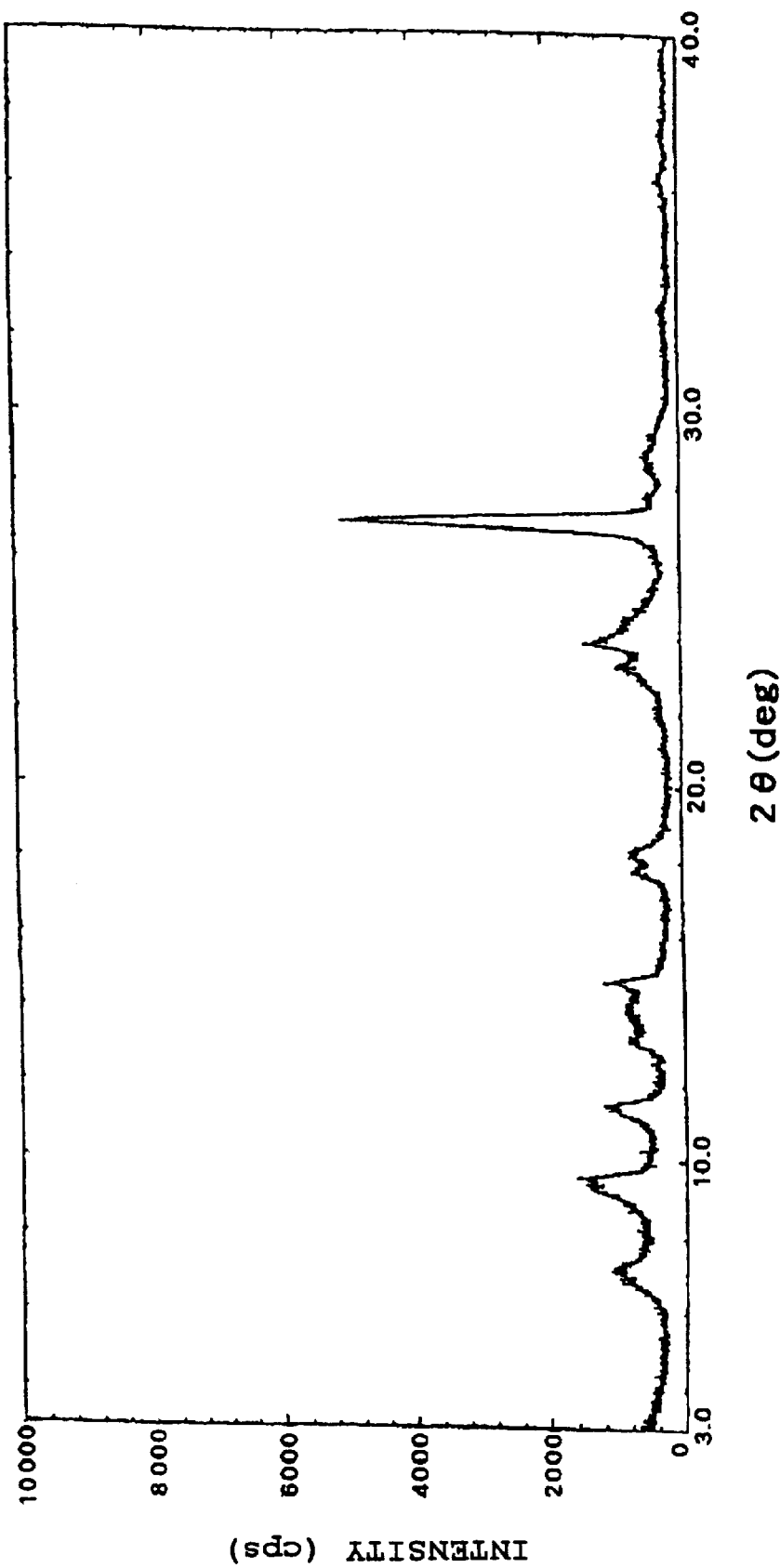
FIG. 17 is an X-ray diffraction spectrum of a reaction product obtained in Example 26.
Figure 18:
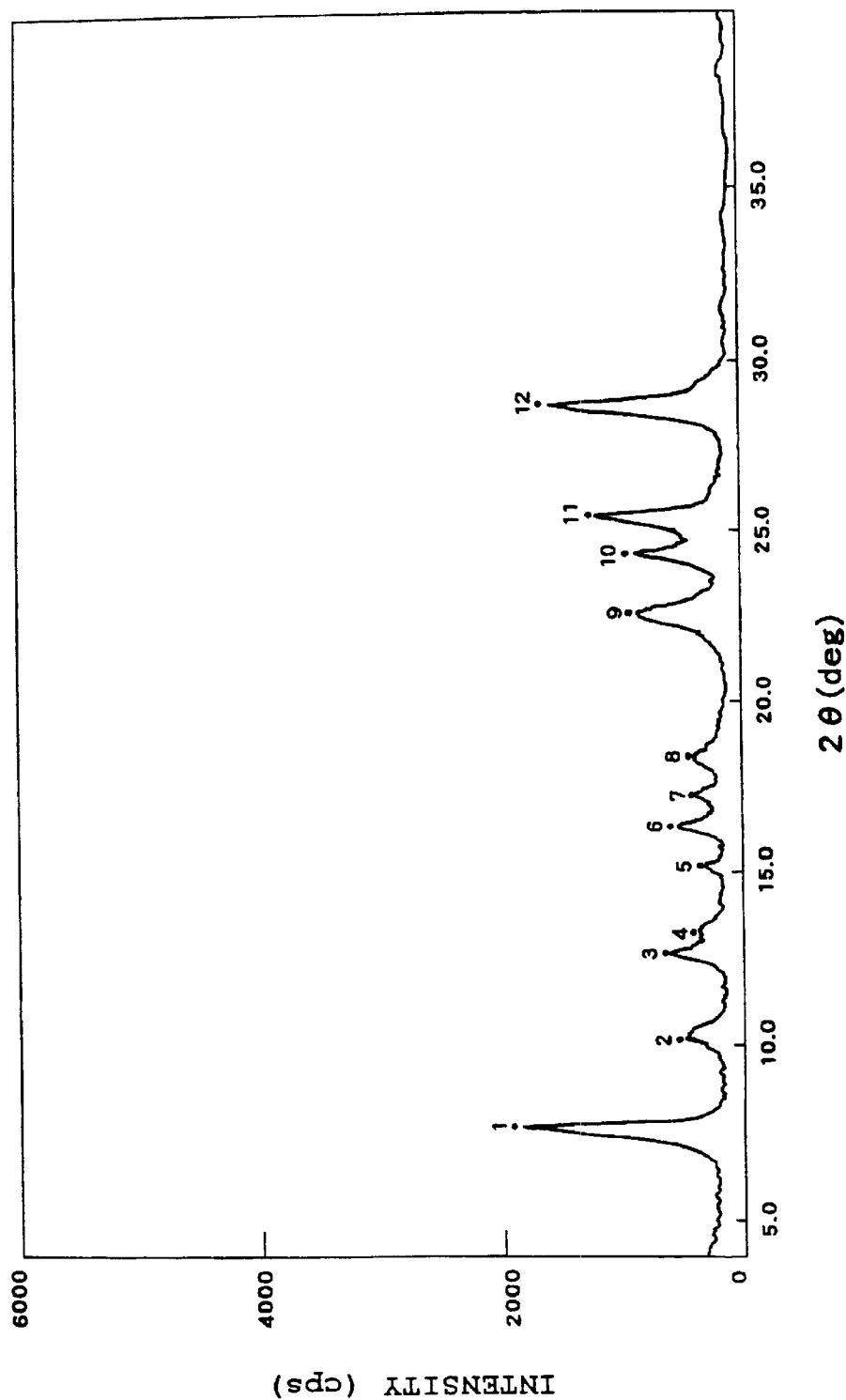
FIG. 18 is an X-ray diffraction spectrum of a reaction product obtained in Example 27.
Figure 19:
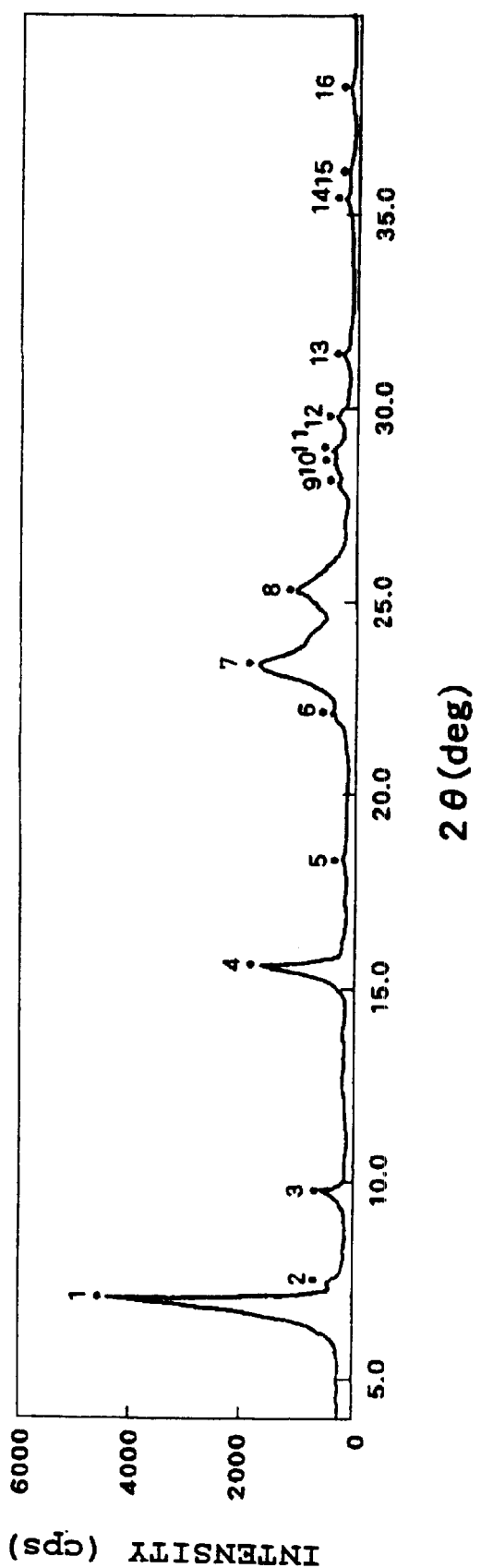
FIG. 19 is an X-ray diffraction spectrum of a reaction product obtained in Example 28.
Figure 20:
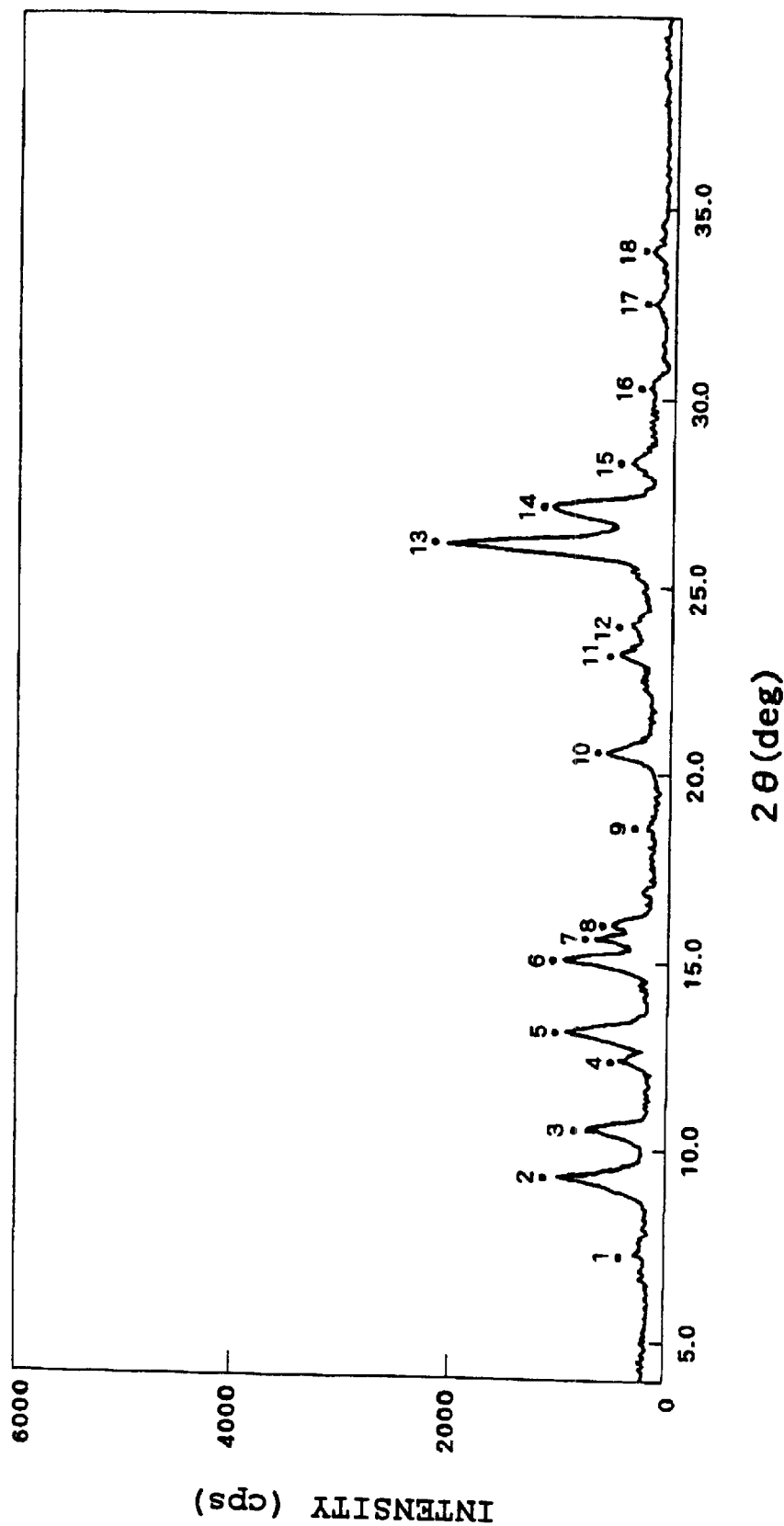
FIG. 20 is an X-ray diffraction spectrum of a reaction product obtained in Example 29.
Figure 21:
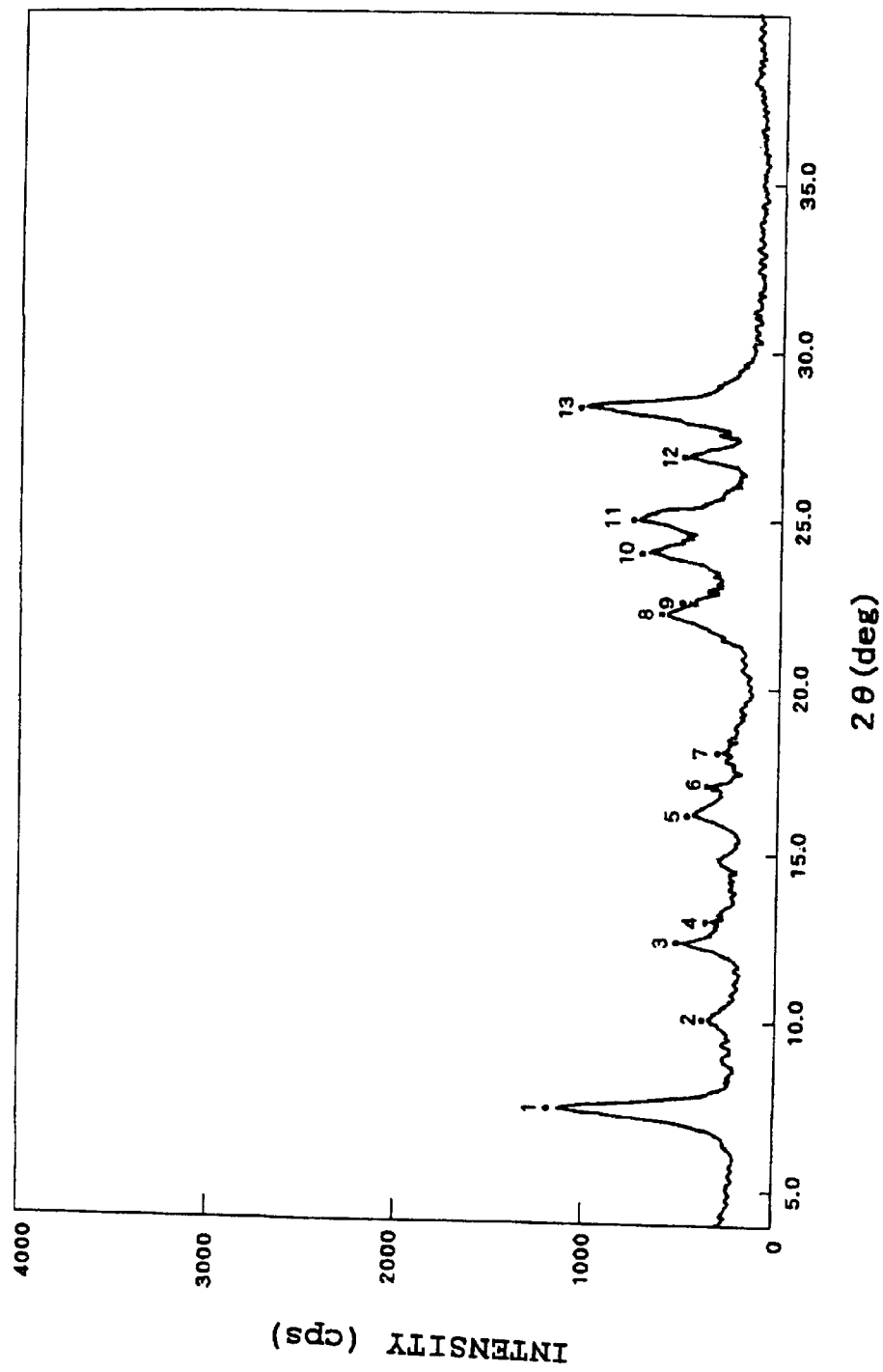
FIG. 21 is an X-ray diffraction spectrum of a reaction product obtained in Example 30.
Figure 22:
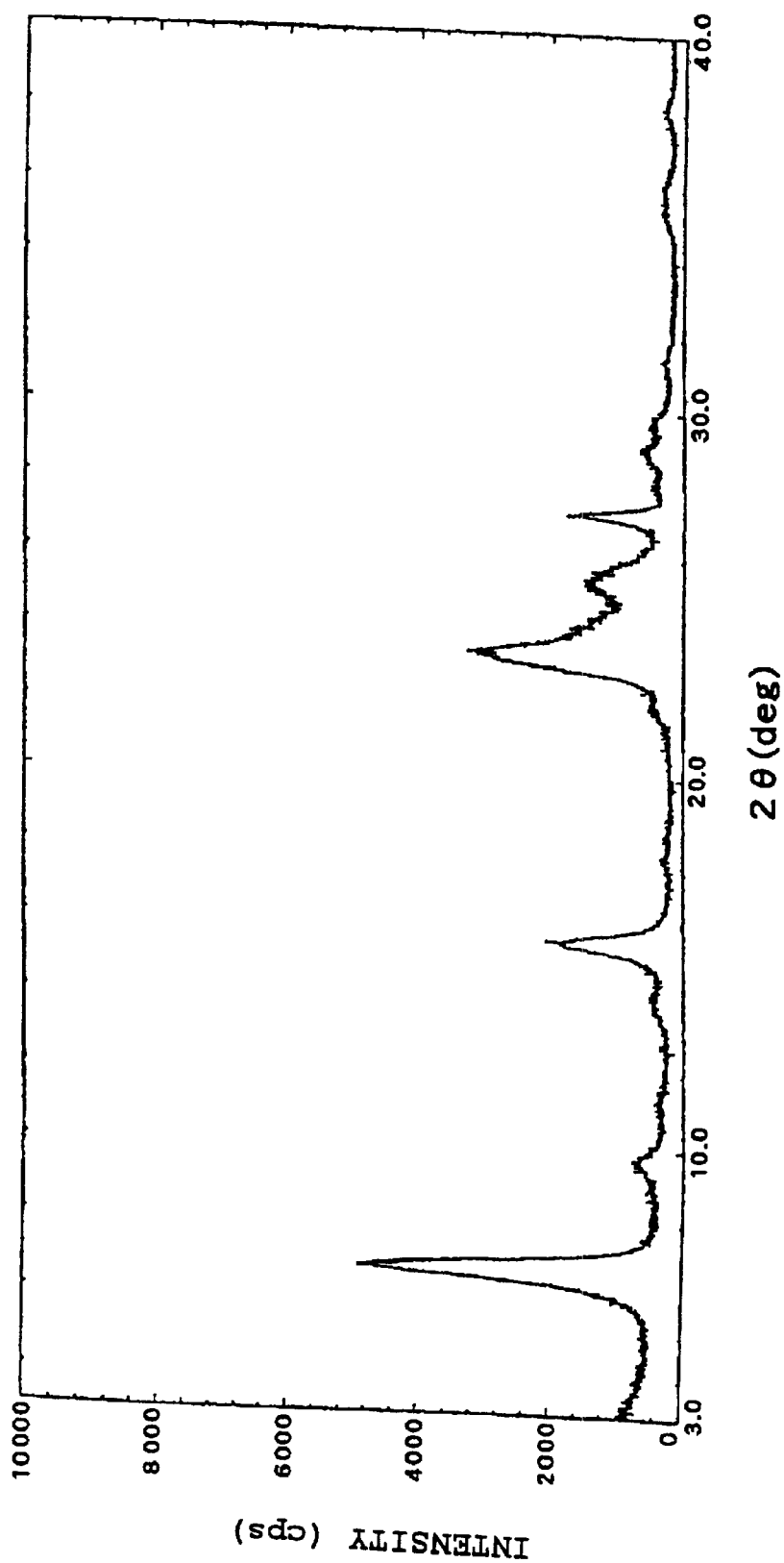
FIG. 22 is an X-ray diffraction spectrum of a reaction product obtained in Example 31.
Figure 23:
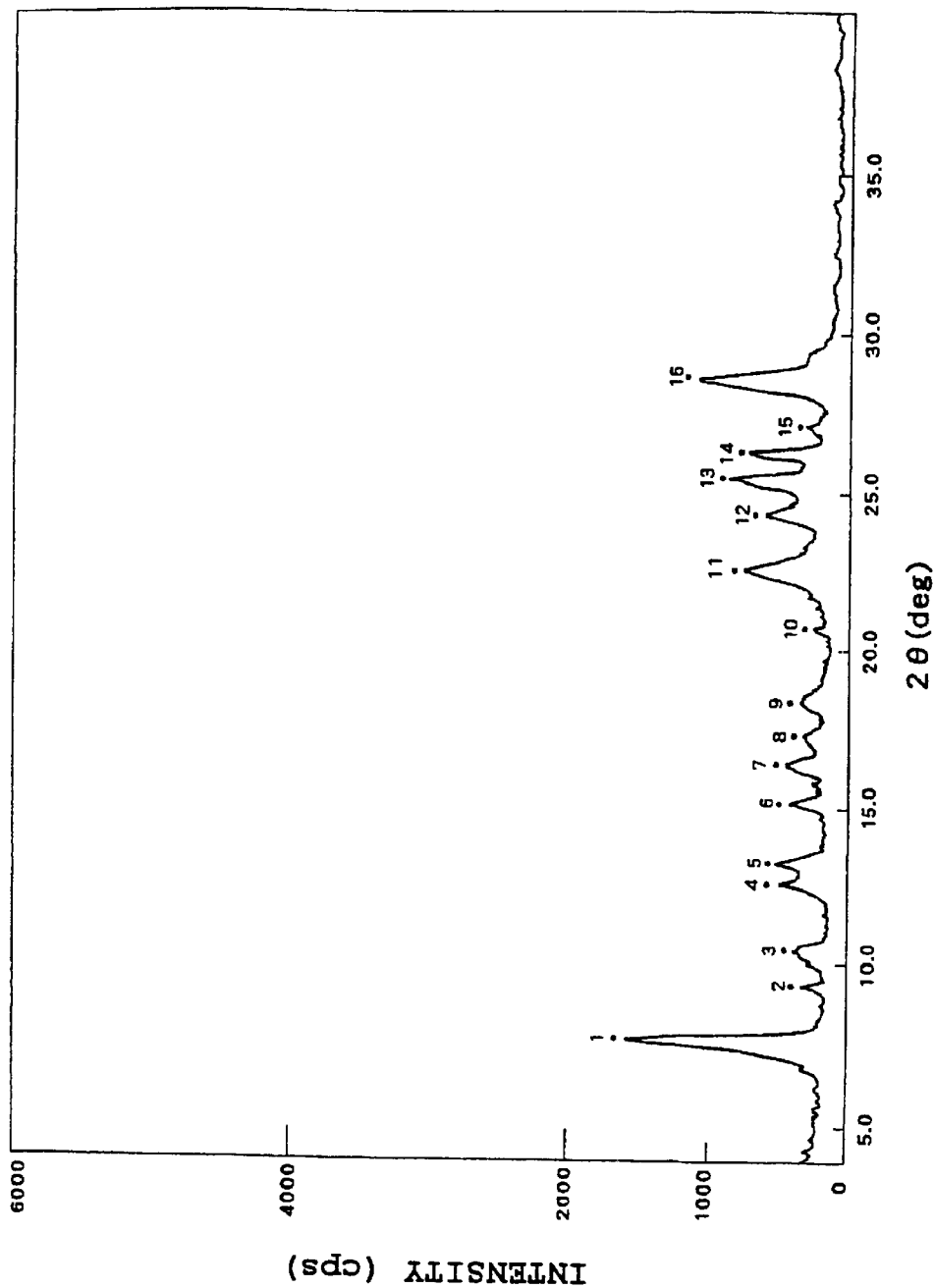
FIG. 23 is an X-ray diffraction spectrum of a reaction product obtained in Example 32.
Figure 24:
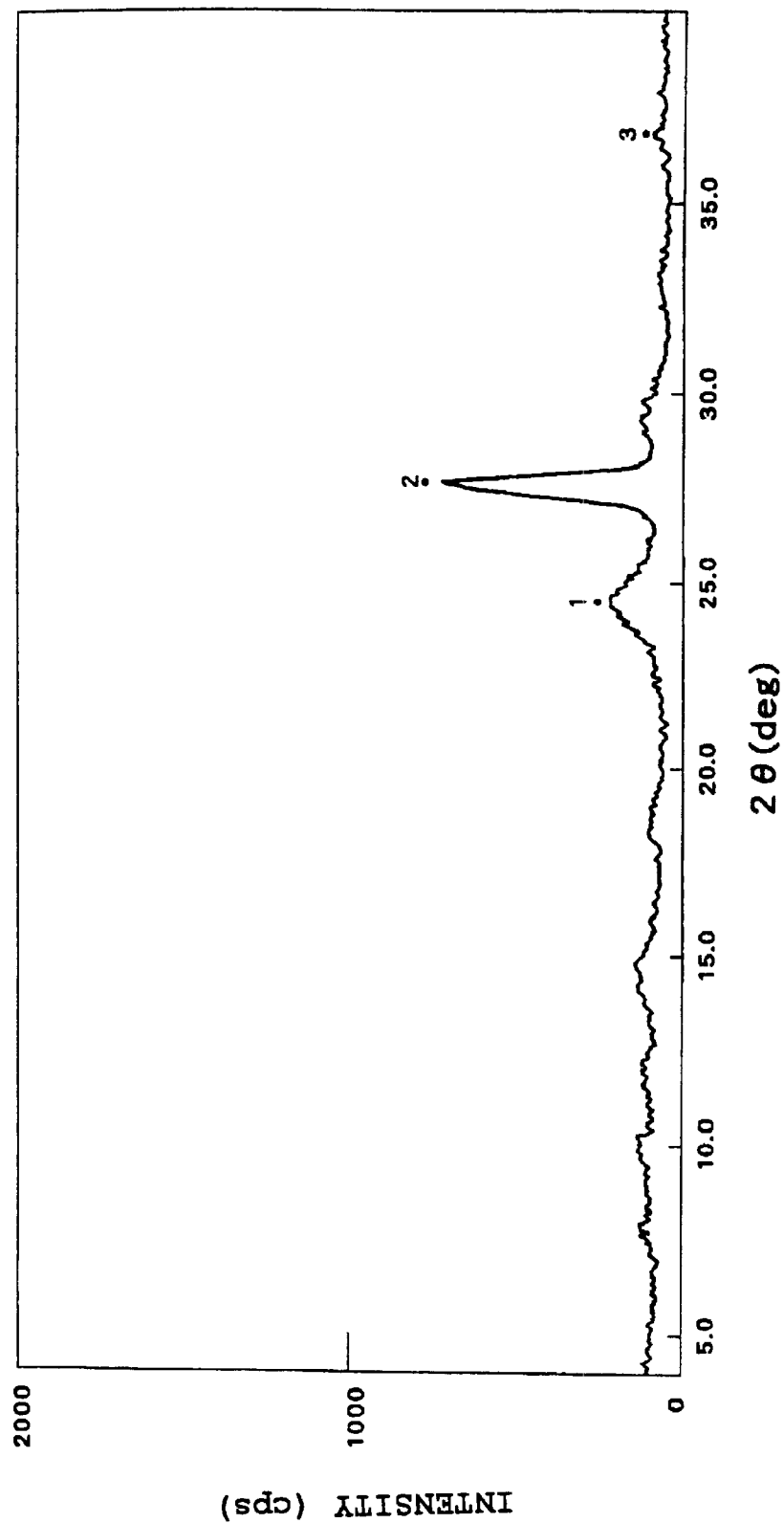
FIG. 24 is an X-ray diffraction spectrum of a reaction product obtained in Example 33.

From FIG. 17, it is seen that the photoconductor of Application Example 1 is more stable in repeated electrostatic fatigue characteristics than photoconductor of Comparative Example. The use of the reaction product according to the present invention is effective for the stability in repeated electrostatic fatigue characteristics.

TABLE 17

|  | $V_0$ [−V] |
| --- | --- |
| Application Example 1 | 820 |
| Comparative Example | 450 |

Application Example 17

A charge generation layer was formed on an aluminum-deposited PET base in the same manner as that of Application Example 1. A coating liquid, which was a solution obtained by dissolving 8 parts by weight of an electron transporting material of the formula (28) shown below, 11 parts by weight of a polycarbonate resin (Polycarbonate Z manufactured by Teijin Chemicals, Ltd.) and 0.02 part by weight of a silicone oil (KF50 manufactured by Shin-Etsu Chemical Co., Ltd.) in 91 parts by weight of tetrahydrofuran, was then applied to the above charge generation layer with a doctor blade and dried to form thereon a charge transport layer having a thickness of 20 $\mu m$, thereby obtaining an electrophotographic photoconductor of Application Example 17.

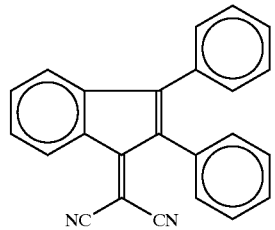

(28)

Application Example 18

Application Example 17 was repeated in the same manner as described except that an electron transporting material of the formula (29) shown below was used in lieu of the charge transporting material of Application Example 17, thereby obtaining a photoconductor of Application Example 18.

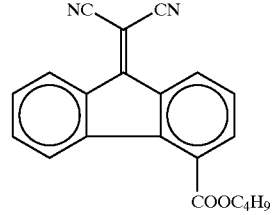

(29)

The photoconductors obtained in Application Examples 17 and 18 were each measured for its photoconductive characteristics in the same manner as that in Application Example 1 except that the impression voltage was changed to +6 KV. The results are shown in Table 18.

TABLE 18

|  | $V_0$ [+V] | $Em_{1/2}$ [$\mu J/cm^2$] |
| --- | --- | --- |
| Application Example 17 | 1100 | 2.50 |
| Application Example 18 | 1200 | 2.35 |

Application Example 19

The reaction product obtained in Example 24 (0.5 g) was milled with a ball mill together with 9 g of tetrahydrofuran and 10 g of Polycarbonate Z (manufactured by Teijin Chemicals, Ltd.; a 10% by weight solution in tetrahydrofuran), to which 10% by weight solution of Polycarbonate Z was blended and sufficiently stirred to obtain a coating liquid containing 2% by weight of the reaction product, 50% by weight of PC-Z and 28% by weight of the charge transporting material of the formula (33). The coating liquid was then applied onto a Al-deposited polyester film with a doctor blade and dried to form a single layer photoconductive layer having a thickness of 15 $\mu m$, thereby obtaining a single layer-type photoconductor of Application Example 19. The photoconductor of Application Example 19 was measured for its photoconductive characteristics in the same manner as that in Application Example 1. The results are shown in Table 19.

TABLE 19

|  | $V_o$ [-V] | $Em_{1/2}$ [$\mu J/cm^2$] |
| --- | --- | --- |
| Application Example 19 | 1150 | 0.6 |

Application Example 20

Figure 32:
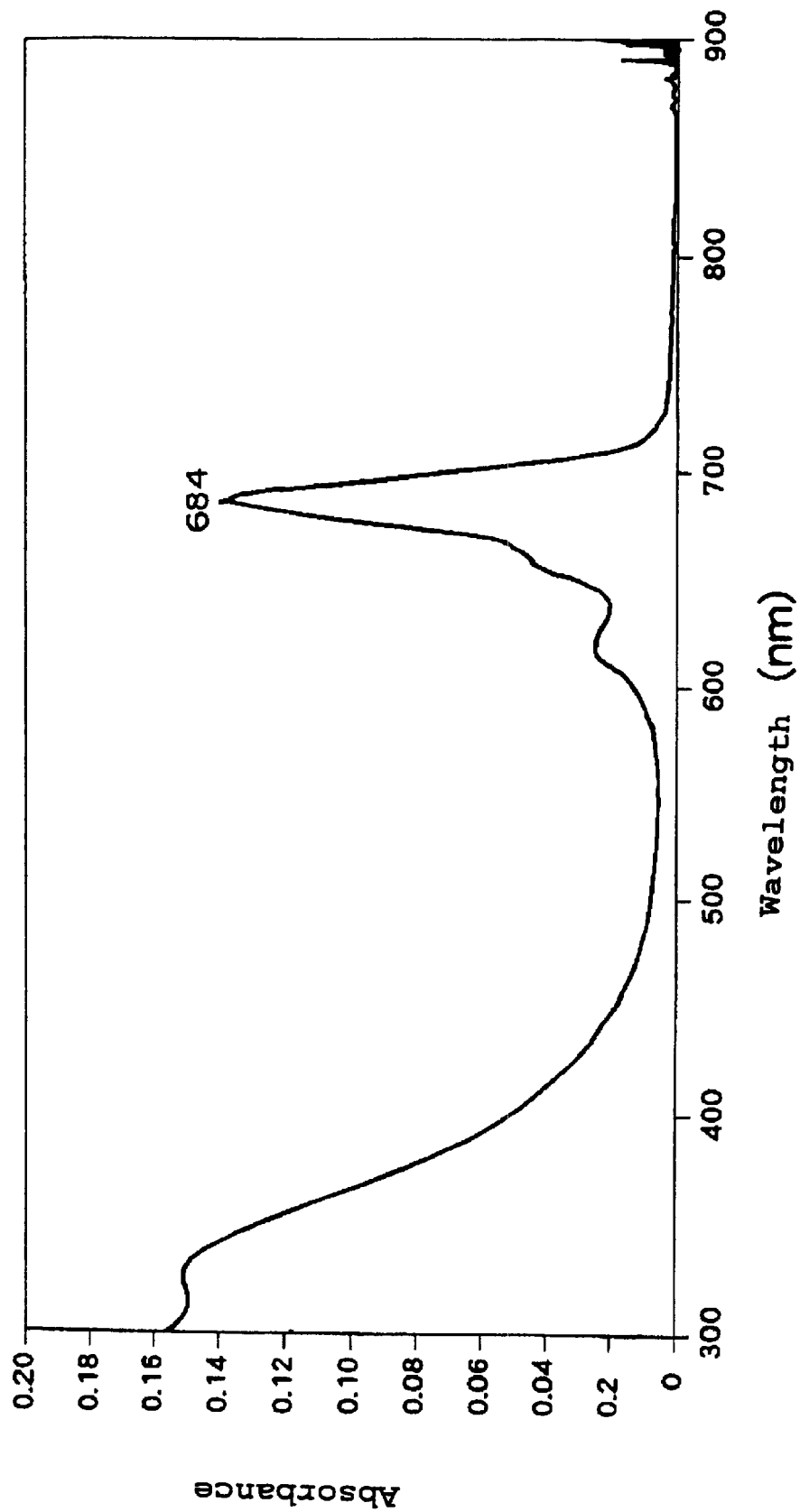
FIG. 32 is a light absorption spectrum of a solution.

FIG. 32 is a solution spectrum of the reaction product obtained in Example 24 (solvent: N,N-dimethylformamide). λmax was 684 nm.

Figure 31:
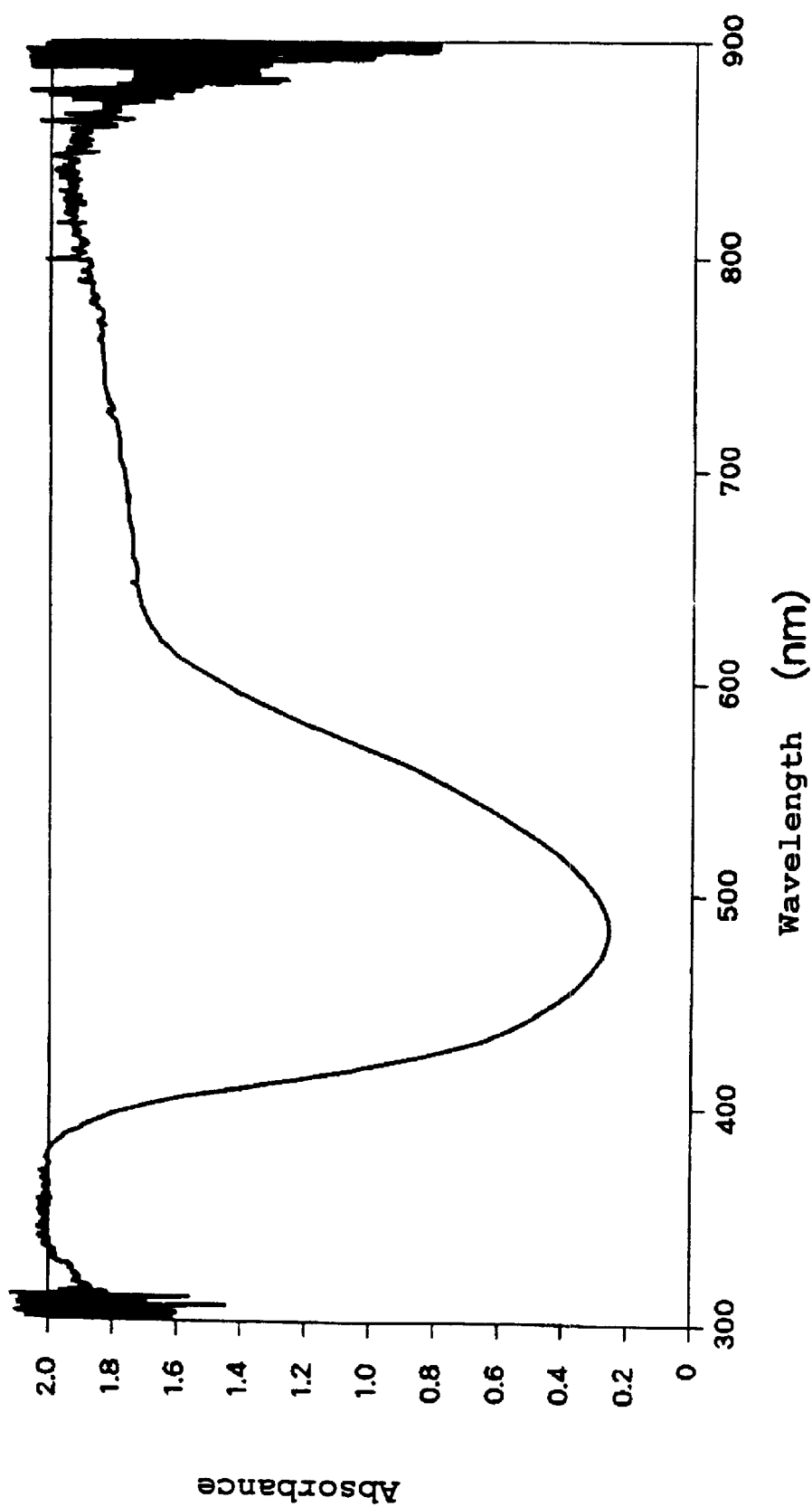
FIG. 31 is a light absorption spectrum.

A dispersion containing 3 parts of the product obtained in Example 24, 1 part of a polyvinyl butyral resin (BM-S manufactured by Sekisui Chemical Co., Ltd.) and 80 parts of methyl ethyl ketone was placed in a ball mill pot and milled for 3 hours using PSZ balls with a diameter of 2 mm to obtain a coating liquid for forming a charge generation layer. This was applied to a polyethylene terephthalate sheet with a thickness of 100 □m and then dried at 100° C. for 20 minutes to obtain a sample for measuring a light absorption spectrum. The light absorption spectrum is shown in FIG. 31. There is an absorption in the wavelength of 500–700 nm.

Application Example 21

The electrophotographic photoconductor fabricated in Application Example 1 was mounted on an electrophotographic device. It was found that the device produced clear images.

Effect of the Invention

The reaction product according to the present invention has charge generating properties and good chargeability and sensitivity and can provide excellent electrophotographic photoconductor. The electrophotographic photoconductor according to the present invention permits the application thereof for an electrophotographic device.

What is claimed is:

1. A pigment comprising a reaction product having charge generating properties which is prepared by reacting a nitrile derivative of formula (1) with a phthalonitrile derivative of formula (2):

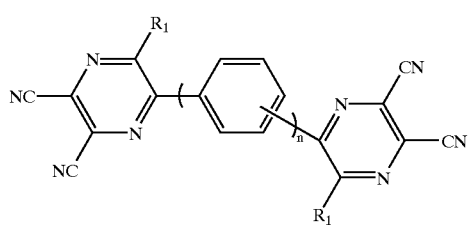

(1)

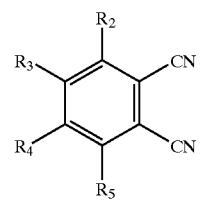

(2)

wherein $R_1$–$R_5$ independently represent a hydrogen atom, a halogen atom, an aliphatic hydrocarbyl group, a substituted hydrocarbyl group, an aromatic group, a substituted aromatic group, a hydrocarbyloxy group, a substituted hydrocarbyloxy group, a nitro group or a cyano group and n is an integer of 1 or 2, or any two of $R_2$–$R_5$ define a ring fused to the aromatic ring of formula (2).

2. An electrophotographic photoconductor comprising an electroconductive support and a photoconductive layer provided thereon, wherein said photoconductive layer comprises a pigment as recited in claim 1.

3. An electrophotographic photoconductor as claimed in claim 2, wherein said photoconductive layer comprises a charge generation layer comprising a charge generating substance and a charge transport layer comprising a charge transporting substance and said charge generation layer comprises said pigment.

4. An electrophotographic photoconductor as claimed in claim 3, wherein said charge transporting substance is a positive hole transport substance and said charge generation layer and said charge transport layer are disposed on said support in this order, and said electrophotographic photoconductor is a negatively charged electrophotographic photoconductor.

5. An electrophotographic photoconductor as claimed in claim 4, wherein said positive hole transport substance is a stilbene compound represented by the following formula (4):

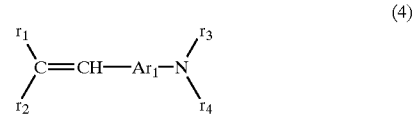

(4)

wherein $r_1$ and $r_2$ represent, independently from each other, a substituted or unsubstituted alkyl group or a substituted or unsubstituted aryl group, $r_3$ and $r_4$ represent, independently from each other, a hydrogen atom, a substituted or unsubstituted alkyl group, a substituted or unsubstituted aryl group, or a heterocyclic group, with the proviso that $r_1$ and $r_2$ may together form a ring, and $Ar_1$ represents a substituted or unsubstituted aryl group or a heterocyclic group.

6. An electrophotographic photoconductor as claimed in claim 3, wherein said charge generation layer and said charge transport layer are disposed on said support in this order, and said electrophotographic photoconductor is a positively charged electrophotographic photoconductor.

7. An electrophotographic photoconductor as claimed in claim 6, wherein said charge transporting substance is a 2,3-diphenylindene compound represented by the following formula (5):

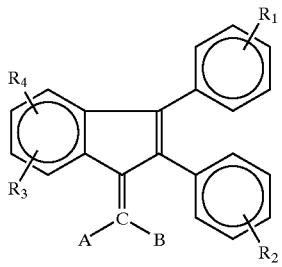

wherein $R_1$–$R_4$ represent, independently from each other, for a hydrogen atom, a halogen atom, a substituted or unsubstituted alkyl group, a cyano group or a nitro group, and A and B represent, independently from each other, a hydrogen atom, a halogen atom, a substituted or unsubstituted aryl group, a cyano group, an alkoxycarbonyl group or an aryloxycarbonyl group.

8. An electrophotographic photoconductor as claimed in claim 2, wherein said photoconductive layer is formed into a single layer.

9. An electrophotographic machine comprising charging means, exposing means, developing means, transfer means, cleaning means, charge removing means and the electrophotographic photoconductor according to claim 2.

10. A process cartridge for an electrophotographic machine comprising charging means and the electrophotographic photoconductor according to claim 2.

11. A pigment having charge generating properties comprising the reaction product obtained by reacting a nitrile derivative of formula (1) with a phthalonitrile derivative of formula (2) and a metal or metal compound:

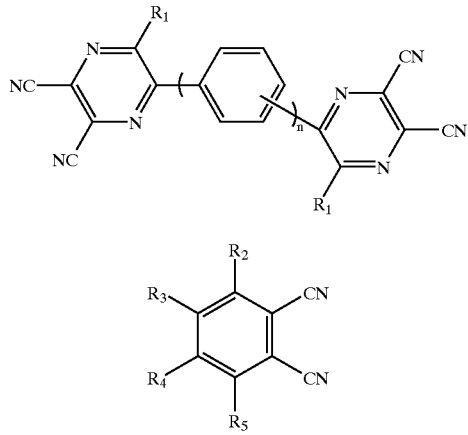

wherein $R_1$–$R_5$ independently represent a hydrogen atom, a halogen atom, an aliphatic hydrocarbyl group, a substituted hydrocarbyl group, an aromatic group, a substituted aromatic group, a hydrocarbyloxy group, a substituted hydrocarbyloxy group, a nitro group or a cyano group and n is an integer of 1 or 2, or any two of $R_2$–$R_5$ define a ring fused to the aromatic ring of formula (2).

12. An electrophotographic photoconductor comprising an electroconductive support and a photoconductive layer provided thereon, wherein said photoconductive layer contains the pigment recited in claim 11.

13. The electrophotographic photoconductor as claimed in claim 12, wherein said photoconductive layer comprises a charge generation layer comprising a charge generating substance and a charge transport layer comprising a charge transporting substance and said charge generation layer comprises said pigment.

14. The electrophotographic photoconductor as claimed in claim 13, wherein said charge transporting substance is a positive hole transport substance and said charge generation layer and said charge transport layer are disposed on said support in this order, and wherein said electrophotographic photoconductor is a negatively charged electrophotographic photoconductor.

15. The electrophotographic photoconductor as claimed in claim 14, wherein said positive hole transport substance is a stilbene compound represented by the following formula (4):

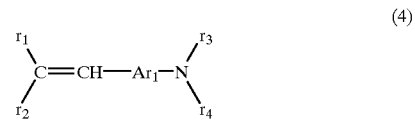

wherein $r_1$ and $r_2$ represent, independently from each other, a substituted or unsubstituted alkyl group or a substituted or unsubstituted aryl group, $r_3$ and $r_4$ represent, independently from each other, a hydrogen atom, a substituted or unsubstituted alkyl group, a substituted or unsubstituted aryl group, or a heterocyclic group, with the proviso that $r_1$ and $r_2$ may together form a ring, and $Ar_1$ represents a substituted or unsubstituted aryl group or a heterocyclic group.

16. The electrophotographic photoconductor as claimed in claim 13, wherein said charge generation layer and said charge transport layer are disposed on said support in this order, and said electrophotographic photoconductor is a positively charged electrophotographic photoconductor.

17. The electrophotographic photoconductor as claimed in claim 16, wherein said charge transporting substance is a 2,3-diphenylindene compound represented by the following formula (5):

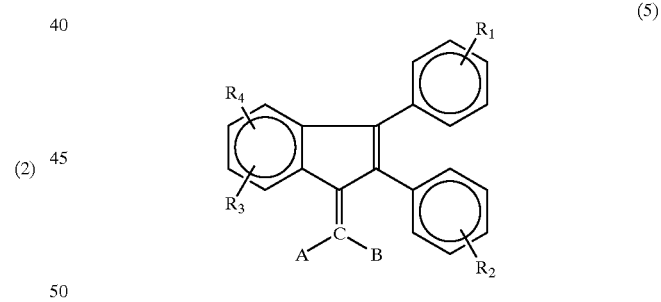

wherein $R_1$–$R_4$ represent, independently from each other, for a hydrogen atom, a halogen atom, a substituted or unsubstituted alkyl group, a cyano group or a nitro group, and A and B represent, independently from each other, for a hydrogen atom, a halogen atom, a substituted or unsubstituted aryl group, a cyano group, an alkoxycarbonyl group or an aryloxycarbonyl group.

18. The electrophotographic photoconductor as claimed in claim 13, wherein said photoconductive layer is formed into a single layer.

19. An electrophotographic machine comprising charging means, exposing means, developing means, transfer means, cleaning means, charge removing means and the electrophotographic photoconductor according to claim 13.

20. A process cartridge for an electrophotographic machine comprising charging means and the electrophotographic photoconductor according to claim 13.

21. A pigment having charge generating properties comprising the reaction product obtained by reacting a nitrile derivative of formula (1) with a 1,3-diiminoisoindoline derivative of formula (3):

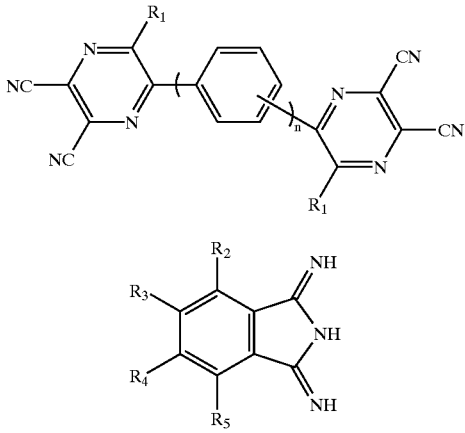

wherein $R_1$–$R_5$ are independently a hydrogen atom, a halogen atom, an aliphatic hydrocarbyl group, a substituted hydrocarbyl group, an aromatic group, a substituted aromatic group, a hydrocarbyloxy group, a substituted hydrocarbyloxy group, a nitro group or a cyano group and n is an integer of 1 or 2, or any two of $R_2$–$R_5$ define a ring fused to the aromatic ring of formula (3), wherein said reaction product.

22. An electrophotographic photoconductor comprising an electroconductive support and a photoconductive layer provided thereon, wherein said photoconductive layer contains the pigment recited in claim 21.

23. The electrophotographic photoconductor as claimed in claim 22, wherein said photoconductive layer comprises a charge generation layer comprising a charge generating substance and a charge transport layer comprising a charge transporting substance and said charge generation layer comprises said pigment.

24. The electrophotographic photoconductor as claimed in claim 23, wherein said charge transporting substance is a positive hole transport substance and said charge generation layer and said charge transport layer are disposed on said support in this order, and wherein said electrophotographic photoconductor is a negatively charged electrophotographic photoconductor.

25. The electrophotographic photoconductor as claimed in claim 24, wherein said positive hole transport substance is a stilbene compound represented by the following formula (4):

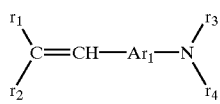

wherein $r_1$ and $r_2$ represent, independently from each other, a substituted or unsubstituted alkyl group or a substituted or unsubstituted aryl group, $r_3$ and $r_4$ represent, independently from each other, a hydrogen atom, a substituted or unsubstituted alkyl group, a substituted or unsubstituted aryl group, or a heterocyclic group, with the proviso that $r_1$ and $r_2$ may together form a ring, and $Ar_1$ represents a substituted or unsubstituted aryl group or a heterocyclic group.

26. The electrophotographic photoconductor as claimed in claim 23, wherein said charge generation layer and said charge transport layer are disposed on said support in this order, and said electrophotographic photoconductor is a positively charged electrophotographic photoconductor.

27. The electrophotographic photoconductor as claimed in claim 26, wherein said charge transporting substance is a 2,3-diphenylindene compound represented by the following formula (5):

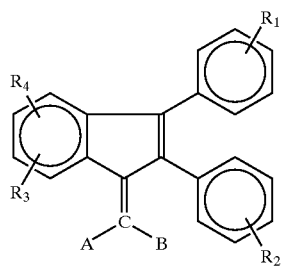

wherein $R_1$–$R_4$ represent, independently from each other, for a hydrogen atom, a halogen atom, a substituted or unsubstituted alkyl group, a cyano group or a nitro group, and A and B represent, independently from each other, for a hydrogen atom, a halogen atom, a substituted or unsubstituted aryl group, a cyano group, an alkoxycarbonyl group or an aryloxycarbonyl group.

28. The electrophotographic photoconductor as claimed in claim 23, wherein said photoconductive layer is formed into a single layer.

29. An electrophotographic machine comprising charging means, exposing means, developing means, transfer means, cleaning means, charge removing means and the electrophotographic photoconductor according to claim 23.

30. A process cartridge for an electrophotographic machine comprising charging means and the electrophotographic photoconductor according to claim 23.

31. A pigment having charge generating properties comprising a reaction product obtained by reacting a nitrile derivative of formula (1) with a 1,3-diiminoisoindoline derivative of formula (3) and a metal or a metal compound:

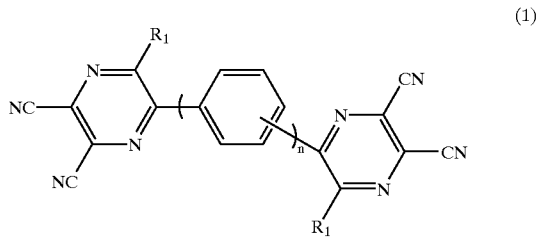

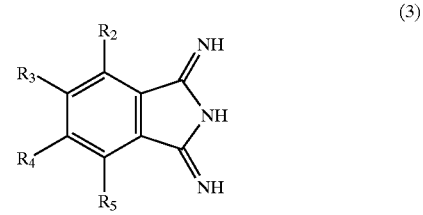

wherein $R_1$–$R_5$ independently represent a hydrogen atom, a halogen atom, an aliphatic hydrocarbyl group, a substituted hydrocarbyl group, an aromatic group, a substituted aromatic group, a hydrocarbyloxy group, a substituted hydrocarbyloxy group, a nitro group or a cyano group and n is an integer of 1 or 2, or any two of $R_2$–$R_5$ define a ring fused to the aromatic ring of formula (3).

32. An electrophotographic photoconductor comprising an electroconductive support and a photoconductive layer provided thereon, wherein said photoconductive layer contains the pigment recited in claim 31.

33. The electrophotographic photoconductor as claimed in claim 32, wherein said photoconductive layer comprises a charge generation layer comprising a charge generating substance and a charge transport layer comprising a charge transporting substance and said charge generation layer comprises said pigment.

34. The electrophotographic photoconductor as claimed in claim 33, wherein said charge transporting substance is a positive hole transport substance and said charge generation layer and said charge transport layer are disposed on said support in this order, and wherein said electrophotographic photoconductor is a negatively charged electrophotographic photoconductor.

35. The electrophotographic photoconductor as claimed in claim 34, wherein said positive hole transport substance is a stilbene compound represented by the following formula (4):

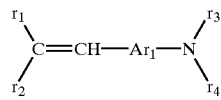

(4)

wherein $r_1$ and $r_2$ represent, independently from each other, a substituted or unsubstituted alkyl group or a substituted or unsubstituted aryl group, $r_3$ and $r_4$ represent, independently from each other, a hydrogen atom, a substituted or unsubstituted alkyl group, a substituted or unsubstituted aryl group, or a heterocyclic group, with the proviso that $r_1$ and $r_2$ may together form a ring, and $Ar_1$ represents a substituted or unsubstituted aryl group or a heterocyclic group.

36. The electrophotographic photoconductor as claimed in claim 33, wherein said charge generation layer and said charge transport layer are disposed on said support in this order, and said electrophotographic photoconductor is a positively charged electrophotographic photoconductor.

37. The electrophotographic photoconductor as claimed in claim 36, wherein said charge transporting substance is a 2,3-diphenylindene compound represented by the following formula (5):

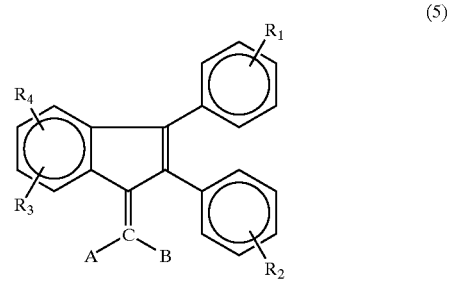

(5)

wherein $R_1$–$R_4$ represent, independently from each other, for a hydrogen atom, a halogen atom, a substituted or unsubstituted alkyl group, a cyano group or a nitro group, and A and B represent, independently from each other, for a hydrogen atom, a halogen atom, a substituted or unsubstituted aryl group, a cyano group, an alkoxycarbonyl group or an aryloxycarbonyl group.

38. The electrophotographic photoconductor as claimed in claim 33, wherein said photoconductive layer is formed into a single layer.

39. An electrophotographic machine comprising charging means, exposing means, developing means, transfer means, cleaning means, charge removing means and the electrophotographic photoconductor according to claim 33.

40. A process cartridge for an electrophotographic machine comprising charging means and the electrophotographic photoconductor according to claim 33.

* * * * *